United States Patent
Angel et al.

(10) Patent No.: US 11,692,203 B2
(45) Date of Patent: *Jul. 4, 2023

(54) METHODS AND PRODUCTS FOR TRANSFECTING CELLS

(71) Applicant: Factor Bioscience Inc., Cambridge, MA (US)

(72) Inventors: Matthew Angel, Cambridge, MA (US); Christopher Rohde, Cambridge, MA (US)

(73) Assignee: Factor Bioscience Inc., Cambridge, MA (US)

( * ) Notice: Subject to any disclaimer, the term of this patent is extended or adjusted under 35 U.S.C. 154(b) by 464 days.

This patent is subject to a terminal disclaimer.

(21) Appl. No.: 16/913,306

(22) Filed: Jun. 26, 2020

(65) Prior Publication Data

US 2020/0325447 A1    Oct. 15, 2020

Related U.S. Application Data

(63) Continuation of application No. 16/857,894, filed on Apr. 24, 2020, now Pat. No. 10,829,738, which is a continuation of application No. 16/776,765, filed on Jan. 30, 2020, now Pat. No. 10,662,410, which is a continuation of application No. 16/567,059, filed on Sep. 11, 2019, now Pat. No. 11,466,293, which is a continuation of application No. 16/402,175, filed on May 2, 2019, now Pat. No. 10,472,611, which is a continuation of application No. 15/429,795, filed on Feb. 10, 2017, now abandoned, which is a continuation of application No. 15/222,453, filed on Jul. 28, 2016, now Pat. No. 9,605,278, which is a continuation of application No. 14/296,220, filed on Jun. 4, 2014, now Pat. No. 9,422,577, which is a continuation of application No. PCT/US2012/067966, filed on Dec. 5, 2012.

(60) Provisional application No. 61/664,494, filed on Jun. 26, 2012, provisional application No. 61/637,570, filed on Apr. 24, 2012, provisional application No.
(Continued)

(51) Int. Cl.
| | |
|---|---|
| *C12N 15/85* | (2006.01) |
| *C12N 15/87* | (2006.01) |
| *C08K 5/5399* | (2006.01) |
| *C12N 5/074* | (2010.01) |
| *H01L 31/048* | (2014.01) |
| *C12P 21/00* | (2006.01) |
| *C12N 9/16* | (2006.01) |
| *C12N 5/0789* | (2010.01) |
| *C12N 5/077* | (2010.01) |
| *C12N 15/90* | (2006.01) |
| *C12N 9/22* | (2006.01) |
| *A61K 35/28* | (2015.01) |
| *C08G 77/08* | (2006.01) |
| *A61K 35/12* | (2015.01) |

(52) U.S. Cl.
CPC .............. *C12N 15/87* (2013.01); *A61K 35/28* (2013.01); *C08K 5/5399* (2013.01); *C12N 5/0647* (2013.01); *C12N 5/0657* (2013.01); *C12N 5/0696* (2013.01); *C12N 9/16* (2013.01); *C12N 9/22* (2013.01); *C12N 15/907* (2013.01); *C12P 21/00* (2013.01); *C12Y 301/21* (2013.01); *H01L 31/048* (2013.01); *A61K 2035/124* (2013.01); *C08G 77/08* (2013.01); *C12N 2500/25* (2013.01); *C12N 2500/44* (2013.01); *C12N 2501/115* (2013.01); *C12N 2501/155* (2013.01); *C12N 2501/165* (2013.01); *C12N 2501/2303* (2013.01); *C12N 2501/26* (2013.01); *C12N 2501/91* (2013.01); *C12N 2501/998* (2013.01); *C12N 2506/09* (2013.01); *C12N 2800/80* (2013.01); *Y02E 10/50* (2013.01)

(58) Field of Classification Search
None
See application file for complete search history.

(56) References Cited

U.S. PATENT DOCUMENTS

| | | |
|---|---|---|
| 2,705,230 A | 3/1955 | Reid |
| 3,539,465 A | 11/1970 | Jensen et al. |
| 5,843,780 A | 12/1998 | Thomson |
| | (Continued) | |

FOREIGN PATENT DOCUMENTS

| | | |
|---|---|---|
| CN | 101432031 A | 5/2009 |
| EP | 2241572 | 10/2010 |
| | (Continued) | |

OTHER PUBLICATIONS

Ludwig et al., "Derivation of human embryonic stem cells in defined conditions," Nat. Biotechnol. 24, pp. 185-187 (Feb. 2006).
(Continued)

*Primary Examiner* — Marcia S Noble
(74) *Attorney, Agent, or Firm* — Wilson Sonsini Goodrich & Rosati

(57) ABSTRACT

The present invention relates in part to nucleic acids encoding proteins, nucleic acids containing non-canonical nucleotides, therapeutics comprising nucleic acids, methods, kits, and devices for inducing cells to express proteins, methods, kits, and devices for transfecting, gene editing, and reprogramming cells, and cells, organisms, and therapeutics produced using these methods, kits, and devices. Methods for inducing cells to express proteins and for reprogramming and gene-editing cells using RNA are disclosed. Methods for producing cells from patient samples, cells produced using these methods, and therapeutics comprising cells produced using these methods are also disclosed.

32 Claims, 11 Drawing Sheets

Specification includes a Sequence Listing.

Related U.S. Application Data

61/569,595, filed on Dec. 12, 2011, provisional application No. 61/566,948, filed on Dec. 5, 2011.

(56) References Cited

U.S. PATENT DOCUMENTS

| | | |
|---|---|---|
| 7,276,489 B2 | 10/2007 | Agrawal et al. |
| 7,442,548 B2 | 10/2008 | Thomson et al. |
| 7,449,334 B2 | 11/2008 | Thomson et al. |
| 7,621,606 B2 | 11/2009 | Page et al. |
| 7,682,828 B2 | 3/2010 | Jaenisch et al. |
| 7,687,266 B2 | 3/2010 | Chambers et al. |
| 7,812,000 B2 | 10/2010 | Agrawal et al. |
| 8,048,675 B1 | 11/2011 | Irion |
| 8,048,999 B2 | 11/2011 | Yamanaka et al. |
| 8,058,065 B2 | 11/2011 | Yamanaka et al. |
| 8,071,369 B2 | 12/2011 | Jaenisch et al. |
| 8,129,187 B2 | 3/2012 | Yamanaka et al. |
| 8,202,850 B2 | 6/2012 | Agrawal et al. |
| 8,278,036 B2 | 10/2012 | Kariko et al. |
| 8,420,782 B2 | 4/2013 | Bonas et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,470,973 B2 | 6/2013 | Bonas et al. |
| 8,586,526 B2 | 11/2013 | Gregory et al. |
| 8,691,966 B2 | 4/2014 | Kariko et al. |
| 8,709,492 B2 | 4/2014 | Teschner et al. |
| 8,710,200 B2 | 4/2014 | Schrum et al. |
| 8,716,465 B2 | 5/2014 | Rossi et al. |
| 8,748,089 B2 | 6/2014 | Kariko et al. |
| 8,802,438 B2 | 8/2014 | Rossi et al. |
| 8,822,663 B2 | 9/2014 | Schrum et al. |
| 8,835,108 B2 | 9/2014 | Kariko et al. |
| 8,883,506 B2 | 11/2014 | Rossi et al. |
| 10,662,410 B1 | 5/2020 | Angel et al. |
| 10,829,738 B2 | 11/2020 | Angel et al. |
| 10,982,229 B2 | 4/2021 | Angel et al. |
| 2003/0083272 A1 | 5/2003 | Wiederholt et al. |
| 2005/0053588 A1 | 3/2005 | Yin |
| 2005/0130144 A1 | 6/2005 | Nakatsuji et al. |
| 2007/0134796 A1 | 6/2007 | Holmes et al. |
| 2008/0233610 A1 | 9/2008 | Thomson et al. |
| 2008/0260706 A1 | 10/2008 | Rabinovich et al. |
| 2009/0029465 A1 | 1/2009 | Thomson et al. |
| 2009/0093433 A1 | 4/2009 | Woolf et al. |
| 2009/0275128 A1 | 11/2009 | Thomson et al. |
| 2009/0286852 A1 | 11/2009 | Kariko et al. |
| 2010/0003757 A1 | 1/2010 | Mack et al. |
| 2010/0047261 A1 | 2/2010 | Hoerr et al. |
| 2010/0075421 A1 | 3/2010 | Yamanka et al. |
| 2010/0076057 A1 | 3/2010 | Sontheimer et al. |
| 2010/0120079 A1 | 5/2010 | Page et al. |
| 2010/0144031 A1 | 6/2010 | Jaenisch et al. |
| 2010/0167286 A1 | 7/2010 | Reijo Pera et al. |
| 2010/0168000 A1 | 7/2010 | Kiessling et al. |
| 2010/0172882 A1 | 7/2010 | Glazer et al. |
| 2010/0184033 A1 | 7/2010 | West et al. |
| 2010/0184227 A1 | 7/2010 | Thomson et al. |
| 2010/0221829 A1 | 9/2010 | Amit et al. |
| 2010/0233804 A1 | 9/2010 | Zhou et al. |
| 2010/0267141 A1 | 10/2010 | Shi et al. |
| 2010/0272695 A1 | 10/2010 | Agulnick et al. |
| 2010/0273220 A1 | 10/2010 | Yanik et al. |
| 2010/0304481 A1 | 12/2010 | Thomson et al. |
| 2010/0311171 A1 | 12/2010 | Nakanishi et al. |
| 2010/0317104 A1 | 12/2010 | Elefanty et al. |
| 2011/0045001 A1 | 2/2011 | Klosel et al. |
| 2011/0065103 A1 | 3/2011 | Sahin et al. |
| 2011/0076678 A1 | 3/2011 | Jaenisch et al. |
| 2011/0104125 A1 | 5/2011 | Yu |
| 2011/0105360 A1 | 5/2011 | Derda et al. |
| 2011/0110899 A1 | 5/2011 | Shi et al. |
| 2011/0143397 A1 | 6/2011 | Kariko et al. |
| 2011/0143436 A1 | 6/2011 | Dahl et al. |
| 2011/0145940 A1 | 6/2011 | Voytas et al. |
| 2011/0151557 A1 | 6/2011 | Reh et al. |
| 2011/0165133 A1 | 7/2011 | Rabinovich et al. |
| 2011/0171185 A1 | 7/2011 | Klimanskaya et al. |
| 2011/0189137 A1 | 8/2011 | Rana et al. |
| 2011/0236978 A1 | 9/2011 | Stolzing et al. |
| 2011/0239315 A1 | 9/2011 | Bonas et al. |
| 2011/0244566 A1 | 10/2011 | Wu et al. |
| 2011/0263015 A1 | 10/2011 | D'Costa et al. |
| 2011/0301073 A1 | 12/2011 | Gregory et al. |
| 2012/0046346 A1 | 2/2012 | Rossi et al. |
| 2012/0064620 A1 | 3/2012 | Bonas et al. |
| 2012/0195936 A1 | 8/2012 | Rudolph et al. |
| 2012/0208278 A1 | 8/2012 | Yanik et al. |
| 2012/0237975 A1 | 9/2012 | Schrum et al. |
| 2012/0301455 A1 | 11/2012 | Hunt |
| 2013/0040302 A1 | 2/2013 | Burke et al. |
| 2013/0102034 A1 | 4/2013 | Schrum et al. |
| 2013/0115272 A1 | 5/2013 | de Fougerolles et al. |
| 2013/0122581 A1 | 5/2013 | Voytas et al. |
| 2013/0123481 A1 | 5/2013 | de Fougerolles et al. |
| 2013/0156849 A1 | 6/2013 | de Fougerolles et al. |
| 2013/0165504 A1 | 6/2013 | Bancel et al. |
| 2013/0189741 A1 | 7/2013 | Meis et al. |
| 2013/0203115 A1 | 8/2013 | Schrum et al. |
| 2013/0217119 A1 | 8/2013 | Bonas et al. |
| 2013/0244282 A1 | 9/2013 | Schrum et al. |
| 2013/0245103 A1 | 9/2013 | de Fougerolles et al. |
| 2013/0302295 A1 | 11/2013 | Wang et al. |
| 2014/0073053 A1 | 3/2014 | Yanik et al. |
| 2014/0073687 A1 | 3/2014 | Chien et al. |
| 2014/0127814 A1 | 5/2014 | Chandrasegaran et al. |
| 2014/0242154 A1 | 8/2014 | Ramunas et al. |
| 2014/0242155 A1 | 8/2014 | Ramunas et al. |
| 2014/0315988 A1 | 10/2014 | Dahl et al. |
| 2014/0349401 A1 | 11/2014 | Wang et al. |
| 2023/0033888 A1 | 2/2023 | Angel et al. |

FOREIGN PATENT DOCUMENTS

| | | |
|---|---|---|
| FR | 2322871 A1 | 4/1977 |
| JP | 2001500867 A | 1/2001 |
| JP | 2005536452 A | 12/2005 |
| JP | 2009502124 A | 1/2009 |
| JP | 2010529851 A | 9/2010 |
| JP | 2010246551 A | 11/2010 |
| JP | 2011160661 A | 8/2011 |
| WO | 1998030679 | 7/1998 |
| WO | WO-0044772 A2 | 8/2000 |
| WO | 2002026757 | 4/2002 |
| WO | WO-03066681 A1 | 8/2003 |
| WO | WO-2007012009 A1 | 1/2007 |
| WO | 2007024708 | 3/2007 |
| WO | 2008065381 | 6/2008 |
| WO | WO-2009007852 A2 | 1/2009 |
| WO | WO-2009077134 A2 | 6/2009 |
| WO | 2009127230 | 10/2009 |
| WO | WO-2009123349 A1 | 10/2009 |
| WO | 2009147400 | 12/2009 |
| WO | 2010093655 | 8/2010 |
| WO | 2010123501 | 10/2010 |
| WO | WO-2011011767 A1 | 1/2011 |
| WO | WO-2011058558 A2 | 5/2011 |
| WO | 2011071931 | 6/2011 |
| WO | 2011071936 | 6/2011 |
| WO | WO-2011072246 A2 | 6/2011 |
| WO | 2011110886 | 9/2011 |
| WO | 2011114237 | 9/2011 |
| WO | 2011012316 | 10/2011 |
| WO | 2011130624 | 10/2011 |
| WO | WO-2011132799 A1 | 10/2011 |
| WO | 2011140397 | 11/2011 |
| WO | 2011141820 | 11/2011 |
| WO | WO-2011134210 A1 | 11/2011 |
| WO | WO-2011139336 A1 | 11/2011 |
| WO | WO-2011146121 A1 | 11/2011 |
| WO | 2011154393 | 12/2011 |
| WO | 2012019122 | 2/2012 |
| WO | 2012019168 | 2/2012 |
| WO | 2012036299 | 3/2012 |

(56) References Cited

FOREIGN PATENT DOCUMENTS

| WO | 2012048213 | 4/2012 |
|---|---|---|
| WO | 2012060473 | 5/2012 |
| WO | 2012122318 | 9/2012 |
| WO | 2012138453 | 10/2012 |
| WO | 2013003475 | 1/2013 |
| WO | 2013102203 | 7/2013 |
| WO | 2013151671 | 10/2013 |
| WO | 2013163296 | 10/2013 |
| WO | 2013173248 | 11/2013 |
| WO | 2014190361 | 11/2014 |

OTHER PUBLICATIONS

Ludwig et al., "Feeder-independent culture of human embryonic stem cells," Nat. Methods 3, pp. 637-646 (Aug. 2006).

Mahfouz et al., "De novo-engineered transcription activator-like effector (TALE) hybrid nuclease witgh novel DNA binding specificity creates double-strand breaks," PNAS vol. 108, No. 6, pp. 2623-2628 (Feb. 8, 2011).

Miller et al., "A TALE nuclease architecture for efficient genome editing," Nature Biotechnology, vol. 29, No. 2, pp. 143-148 (Feb. 2011).

Miller et al., "An improved zinc-finger nuclease architecture for highly specific genome editing," Nat. Biotechnol.; vol. 25, No. 7, pp. 778-785 (Jul. 2007).

MIT Thesis Record, "Reprogramming human somatic cells to pluripotency using RNA," (Matthew Angel, author) (May 15, 2012).

Moscou et al., "A Simple Cipher Governs DNA Recognition by TAL Effectors," Science, vol. 326, p. 1501 (Dec. 11, 2009).

Ng et al., "A protocol describing the use of a recombinant protein-based, animal product-free medium (APEL) for human embryonic stem cell differentiation as spin embryoid bodies," Nat. Protoc. 3, pp. 768-776 (Apr. 10, 2008).

Okita et al., "Generation of germline-competent induced pluripotent stem cells," Nature, vol. 448, pp. 313-317 (Jul. 19, 2007).

Plews et al., "Activation of pluripotency genes in human fibroblast cells by a novel mRNA based approach," PLoS One 5:e14397, pp. 1-10 (Dec. 2010).

Porteus et al., "Gene targeting using zinc finger nucleases," Nat. Biotechnol., vol. 23, No. 8,, pp. 967-973 (2005).

Rossi et al., "Anti-inflammatory cyclopentenone prostaglandins are direct inhibitors of IκB kinase," Nature, vol. 403, pp. 103-108 (Jan. 6, 2000).

Sander et al., "Targeted gene disruption in somatic zebrafish cells using engineered TALENs," Author Manuscript, available in PMC on Feb. 5, 2012. Published in final edited form as: Nat Biotechnol.; 29(8): 697-698. doi:10.1038/nbt.1934.

Sanjana et al., "A transcription activator-like effector toolbox for genome engineering," Nature Protocols, vol. 7, No. 1, pp. 171-192 (2012).

Scheider et al., "An effective method for defatting albumin using resin columns," Biochim. Biophys. Acta, 221; 376-378 (1970).

Schwartz et al., "Embryonic stem cell trials for macular degeneration: a preliminary report," Lancet, pp. 1-8 (Jan. 23, 2012).

Shimizu et al., "Transformation by Wnt Family Proteins Correlates with Regulation of β-Catenin," Cell Growth & Differentiation, vol. 8, pp. 1349-1358 (Dec. 1997).

Soldner et al., "Generation of isogenic pluripotent stem cells differing exclusively at two early onset Parkinson point mutations," Author Manuscript, available in PMC on Jul. 22, 2012. Published in final edited form as: Cell. Jul. 22, 2011; 146(2): 318-331. doi:10.1016/j.cell.2011.06.019.

Takahashi et al., "Induction of pluripotent stem cells from adult human fibroblasts by defined factors," Cell 131, pp. 1-12 (Nov. 30, 2007).

Takahashi, et al., "Induction of pluripotent stem cells from mouse embryonic and adult fibroblast cultures by defined factors," Cell 126, pp. 1-14 (Aug. 25, 2006).

Tesson et al., "Knockout rats generated by embryo microinjection of TALENs," Nature Biotechnology, vol. 29, No. 8, pp. 695-696 (Aug. 2011).

Warren et al., "Highly efficient reprogramming to pluripotency and directed differentiation of human cells with synthetic modified mRNA," Cell. Stem Cell 7, pp. 1-13 (Nov. 5, 2010).

Watanabe et al., "A ROCK inhibitor permits survival of dissociated human embryonic stem cells," Nature Biotechnology, vol. 25, No. 6, pp. 681-686 (Jun. 2007).

Wernig et al., "In vitro reprogramming of fibroblasts into a pluripotent ES-cell-like state," Nature, vol. 448, pp. 317-324 (Jul. 19, 2007).

Wood et al., "Targeted Genome Editing Across Species Using ZFNs and TALENs," Science, vol. 333, p. 307 (Jul. 15, 2011).

"Xeno-Free System for hESC & hiPSC. Facilitating the Shift from Stem Cell Research to Clincal Applications." 12 pages. Biological Industries Catalog (Stem Cell Products) (2011).

Xie et al., "Newly expressed proteins of mouse embryonic fibroblasts irradiated to be inactive," Biochem. Biophys. Res. Commun. 315, pp. 581-588 (2004).

Yakubov et al., "Reprogramming of human fibroblasts to pluripotent stem cells using mRNA of four transcription factors," Biochem. Biophys. Res. Commun. 394, pp. 189-193 (2010).

You et al., "Wnt signaling promotes oncogenic transformation by inhibiting c-Myc-induced apoptosis," The Journal of Cell Biology, vol. 157, No. 3, pp. 429-440 (Apr. 29, 2002).

Young et al., "Background Mutations in Parental Cells Account for Most of the Genetic Heterogeneity of Induced Pluripotent Stem Cells," Cell Stem Cell 10, pp. 570-582 (May 4, 2012).

Yu et al., "Induced pluripotent stem cell lines derived from human somatic cells," Science 318, pp. 1917-1920 (Dec. 21, 2007).

Zhou et al., "Generation of Induced Pluripotent Stem Cells Using Recombinant Proteins," Cell Stem Cell 4, pp. 1-4 (May 8, 2009).

Niu et al., (2008) Engineering Variants of teh I-Scel Homing Endonuclease with Strand-specific and Site-specific DNA-nicking Activity, Journal of Molecular Biology, vol. 382, pp. 188-202.

Mar. 11, 2022 Non-Final Office Action U.S. Appl. No. 16/567,059.

Bogdanove AJ, et al., "TAL Effectors: Customizable Proteins for DNA Targeting", Science, 2011, vol. 333, No. 6051, pp. 1843-1846.

Brazilian Patent Application No. 12 2021 023330-6 Office Action dated Dec. 21, 2021.

Canadian Patent Application No. 2,858,148Office Action dated Aug. 2, 2021.

Cermak, T. et al., "Efficient design and assembly of custom TALEN and other TAL effectorbased constructs for DNA targeting", Nucleic Acids Research, 2011, vol. 39, No. 12, e82, pp. 1-11.

Chen et al., "Role of MEF Feeder Cells in Direct Reprogramming of Mouse tail-tip Fibroblasts", Cell Biology, 2009, vol. 33, No. 12, pp. 1268-1273.

Christian, et al. Targeting DNA double-strand breaks with TAL effector nucleases. Genetics.186 (2010): 757-761.

EP Application No. 20211670 Search Report dated May 17, 2021.

Fusaki et al., Efficient induction of transgene-free human pluripotent stem cells using a vector based on Sendai virus, an RNA virus that does not integrate into the host genome. Proc Jpn Acad Ser B Phys Biol Sci 85(8):348-362 (2009).

Greenberg J.R., "High Stability of Messenger RNA in Growing Cultured Cells", Nature, 1972, Nov. 10, vol. 240:102-104.

Hockmeyer, D, et al., "Genetic engineering of human pluripotent cells using TALE nucleases", Nat Biotechnol, Jul. 7, 2011, vol. 29, No. 8, pp. :731-734.

Holt et al., Human hematopoietic stem/progenitor cells modified by zinc-finger nucleases targeted to CCR5 control HIV-1 in vivo. Nature Biotechnology 28(8): 839-847 (2010).

Holt, N., et al., "Zinc finger nuclease-mediated CCR5 knockout hematopoietic stem cell transplantation controls HIV-1 in vivo", Nat Biotechnol., Aug. 2010; 28(8):839-47, doi:10.1038/nbt.1663.

Kormann, D. et al., "Expression of therapeutic proteins after delivery of chemically modified mRNA in mice", Nature Biotechnology, 2011, vol. 29, No. 2, pp. 154-157.

Mussolino, C, et al., "A novel TALE nuclease scaffold enables high genome editing activity in combination with low toxicity", Nucleic Acids Research, 2011, vol. 39, No. 1, pp. 9283-9293.

(56) References Cited

OTHER PUBLICATIONS

No Author, Autologous T-Cells Genetically Modified at the CCR5 Gene by Zinc Finger Nucleases SB-728 for HIV (Zinc-Finger), View of NCT00842634 on Feb. 11, 2009, ClinicalTrials.gov archive (Feb. 12, 2009) https://clinicaltrials.gov/ct2/show/NCT00842634, 10 pages.

No Author, "mMessage mMachine Kit (Cat#AM1340, AM1344, AM1348)", Instruction Manual, Jan. 2007. 4, pp. 1-34.

PCT/US2012/067966 International Search Report, 5 pages (dated Apr. 11, 2013).

Sharova, L.V, et al., "Database for mRNA Half-Life of 19 977 Genes Obtained by DNA Microarray Analysis of Pluripotent and Differentiating Mouse Embryonic Stem Cells", DNA Research, Feb. 2009; 16(I):45-58.

Sugii, S. et al., "Human and Mouse Adipose-Derived Cells Support Feeder-Independent Induction of Pluripotent Stem Cells", PNAS, 2010, vol. 107, No. 8, pp. 3558-3563.

Takahashi, et al. Induction of pluripotent stem cells from adult human fibroblasts by defined factors. Cell. Nov. 30, 2007;131(5):861-72.

Tesson, L, et al., "Knockout rats generated by embryo microinjection of TALENs",. Nat Biotechnol, Aug. 2011, vol. 29, No. 8, pp. 695-696.

Urnov, F.D., et al., "Genome editing with engineered zinc finger nucleases" Nature Reviews Genetics, Sep. 2010, vol. 11, pp. 636-646.

Van De Parre TJ, et al., "mRNA but not plasmid DNA is efficiently transfected in murine J774A.1 macrophages", Biochem Biophys Res Commun., 2005, 327(I):356-60.

Van Tendeloo VF, et al., "Highly efficient gene delivery by mRNA electroporation in human hematopoietic cells: superiority to lipofection and passive pulsing of mRNA and to electroporation of plasmid cDNA for tumor antigen loading of dendritic cells", Blood, Jul. 1, 2001; 98(I):49-56.

Warren et al., Highly efficient reprogramming to pluripotency and directed differentiation of human cells with synthetic modified mRNA. Cell Stem Cell 7(5):618-630 (2010).

Wiehe, JM, et al., "mRNA-mediated gene delivery into human progenitor cells promotes highly efficient protein expression", J Cell Mol Med., 2007, vol. 3, pp. 521-530.

PCT/US2012/067966 International Preliminary Report on Patentability, 7 pages (dated Jun. 10, 2014).

Albumax I product insert, Invitrogen Corporation (Jun. 2001).

Anderson et al., "Incorporation of pseudouridine into mRNA enhances translation by diminishing PKR activation," Nucl. Acids Res. 38(17), pp. 1-9 (2010).

Anderson et al., "Nucleofection induces transient eiF2a phosphorylation by GCN2 and PERK," Gene Ther., pp. 1-7 (Feb. 2, 2012).

Anderson et al., "Nucleoside modifications in RNA limit activation of 2'-5'-oligoadenylate synthetase and increase resistance to cleavage by RNase L," Nucl. Acids Res. 39(21), pp. 9329-9338 (2011).

Angel et al., "Innate Immune Suppression Enables Frequent Transfection with RNA Encoding Reprogramming Proteins," PLoS ONE, vol. 5(7), e11756, pp. 1-7 (Jul. 2010).

Angel, "Extended Transient Transfection by Repeated Delivery of an In Vitro-Transcribed RNA," Master of Science in Electrical Engineering and Computer Science, 56 pages (Massachusetts Institute of Technology, Cambridge, Massachusetts) (Sep. 2008).

Angel, "Reprogramming Human Somatic Cells to Pluripotency Using RNA", pp. 1-89 (Ph.D. diss., Massachusetts Institute of Technology) (Feb. 2012).

Angel, "Reprogramming human somatic cells to pluripotency using RNA," Doctor of Philosophy in Electrical Engineering and Computer Science, 55 pages (Massachusetts Institute of Technology, Cambridge, Massachusetts) Oct. 11, 2011).

Arnold et al., "Reprogramming of Human Huntington Fibroblasts Using mRNA," ISRN Cell Biology 2012:Article ID 124878, pp. 1-12 (2012).

Barker et al., "A method for the deionization of bovine serum albumin," Tissue Culture Association, pp. 111-112 (1975).

Berg, "Proposed structure for the zinc-binding domains from transcription factor IIIA and related proteins," Proc. Natl. Acad. Sci USA, vol. 85, pp. 99-102 (Jan. 1988).

Boch et al., "Breaking the Code of DNA Binding Specificity of TAL-Type III Effectors," Science, vol. 3126, pp. 1509-1512 (Dec. 11, 2009).

Bolli et al., "Cardiac stem cells in patients with ischaemic cardiomyopathy (SCIPIO): initial results of a randomised phase 1 trial," Lancet, pp. 1-11 (Nov. 14, 2011).

Braam et al., "Recombinant vitronectin is a functionally defined substrate that supports human embryonic stem cell self-renewal via $\alpha \upsilon \beta 5$ integrin," Stem Cells 26, pp. 2257-2265 (2008).

Carroll, "Progress and prospects: Zinc-finger nucleases as gene therapy agents," Gene Therapy, vol. 15, pp. 1463-1468 (2008).

Chen et al., "Chemically defined conditions for human iPSC derivation and culture," Nat. Methods 8, pp. 424-429 (May 2011).

Chen et al., "Rational optimization of reprogramming culture conditions for the generation of induced pluripotent stem cells with ultra high efficiency and fast kinetics," Cell Research 21, pp. 884-894 (2011).

Christian et al., "Targeting DNA Double-Strand Breaks with TAL Effector Nucleases," Genetics, vol. 186, pp. 757-761 (Oct. 2010).

Cui et al., "Targeted integration in rat and mouse embryos with zinc-finger nucleases," Nat. Biotech., vol. 29, No. 1, pp. 64-67 (Jan. 2011).

Davis, "Stabilization of RNA stacking by pseudouriding," Nucleic Acids Research, vol. 23, No. 24, pp. 5020-5026 (1995).

Droge et al., "A comparative study of some physico-chemical properties of human serum albumin samples from different sources—I. Some physico-chemical properties of isoionic human serum albumin solutions," Biochem. Pharmacal. 31, pp. 3775-3779 (1982).

Efe et al., "Conversion of mouse fibroblasts into cardiomyocytes using a direct reprogramming strategy," Nat. Cell Biol. 13, pp. 215-222 (Mar. 2011).

Garcia-Gonzalo et al., "Albumin-associated lipids regulate human embryonic stem cell self-renewal," PLoS One 3: e1384, pp. 1-10 (Jan. 2008).

Geurts et al., "Knockout Rats via Embryo Microinjection of Zine-Finger Nucleases," Science, vol. 325, p. 433 (Jul. 24, 2009).

Goldberg et al., "The incorporation of 5-ribosyluracil triphosphate into RNA in nuclear extracts of mammalian cells," Biochem. Biophys. Res. Commun. 6, pp. 394-398 (1961).

Goldberg et al., "The enzymic synthesis of pseudouridine triphosphate," Biochim. Biophys. Acta, vol. 54, pp. 202-204 (1961).

Goldberg, "Ribonucleic acid synthesis in nuclear extracts of mammalian cells grown in suspension culture; effect of ionic strength and surface-active agents," Biochim. Biophys. Acta, vol. 51, pp. 201-204 (1961).

Gurung et al., "β-Catenin Is a Mediator of the Response of Fibroblasts to Irradiation," The American Journal of Pathology, vol. 174, No. 1, pp. 248-255 (Jan. 2009).

Hamanaka et al., "Generation of Germline-Component Rat Induced Pluripotent Stem Cells," PlosOne, vol. 6, Issue 7, pp. 1-9 (Jul. 2011).

Hockemeyer et al., "Efficient targeting of expressed and silent genes in human ESCs and iPSCs using zinc-finger nucleases," Nature Biotechnology, vol. 27, No. 9, pp. 851-857 (Sep. 2009).

Hockemeyer et al., "Genetic engineering of human ES and iPS cells using TALE nucleases," Author Manuscript, available in PMC Feb. 1, 2012. Published in final edited form as: Nat Biotechnol.; 29(8): 731-734. doi:10.1038/nbt.1927.

International Search Report, PCT/US2012/067966, 5 pages (dated Apr. 11, 2013).

Kahan et al., "The Role of Deoxyribonucleic Acid in Ribonucleic Acid Synthesis," The Journal of Biological Chemistry, vol. 237, No. 12, pp. 3778-3785 (Dec. 1962).

Kariko et al., "Generating the optimal mRNA for therapy: HPLC purification eliminates immune activation and mproves translation of nucleoside-modified, protein-encoding mRNA," Nucl. Acids Res, pp. 1-10 (Sep. 2, 2011).

Kariko et al., "In vivo protein expression from mRNA delivered into adult rat brain," J. Neurosci. Methods 105, pp. 77-86 (2001).

(56) References Cited

OTHER PUBLICATIONS

Kariko et al., "Incorporation of pseudouridine into mRNA yields superior nonimmunogenic vector with increased translational capacity and biological stability," Mol. Ther. 16, pp. 1833-1840 (2008).
Kariko et al., "Increased Erythropoiesis in Mice Injected With Submicrogram Quantities of Pseudouridine-containing mRNA Encoding Erythropoietin," Mol. Ther. 20, pp. 948-953 (May 2012).
Kariko et al., "mRNA is an endogenous ligand for Toll-like receptor 3," J. Biol. Chem. 279, pp. 12542-12550 (2004).
Kariko et al., "Naturally occurring nucleoside modifications suppress the immunostimulatory activity of RNA: implication for therapeutic RNA development," Drug Discovery & Development, vol. 10, No. 5, pp. 523-532 (2007).
Kariko et al., "Suppression of RNA recognition by Toll-like receptors: the impact of nucleoside modification and the evolutionary origin of RNA," Immunity 23, pp. 165-175 (2005).
Kawamata et al., "Generation of genetically modified rats from embryonic stem cells," PNAS, vol. 107, No. 32, pp. 14223-14228 (Aug. 10, 2010).
Kim et al., "Direct reprogramming of human neural stem cells by OCT4," Nature 461, pp. 649-653 (Oct. 2009).
Kim et al., "Generation of Human Induced Pluripotent Stem Cells by Direct Delivery of Reprogramming Proteins," Cell Stem Cell 4, pp. 472-476 (Jun. 5, 2009).
Kim et al., "Hybrid restriction enzymes: Zinc finger fusions to Fok I cleavage domain," Proc. Natl. Acad. Sci. USA, vol. 93, pp. 1156-1160 (Feb. 1996).
Kim et al., "Oct4-induced pluripotency in adult neural stem cells," Cell 136, pp. 411-419 (Feb. 6, 2009).
Kim et al., "Pluripotent stem cells induced from adult neural stem cells by reprogramming with two factors," Nature 454, pp. 1-6 (2008).
Lee et al., "Activation of Innate Immunity Is Required for Efficient Nuclear Reprogramming," Cell 151, pp. 547-558 (Oct. 26, 2012).
Lin et al., "A chemical platform for improved induction of human iPSCs," Nature Methods, vol. 6, No. 11, pp. 805-808 (Nov. 2009).
Liu et al., "A Small-Molecule Agonist of the Wnt Signaling Pathway," Angew. Chem. Int. Ed. 44, pp. 1987-1990 (2005).
Lu et al., "Defined culture conditions of human embryonic stem cells," PNAS 2006, vol. 103, pp. 5688-5693 (Apr. 11, 2006).
Anderson, B.R.: Nucleoside modifications suppress RNA activation of cytoplasmic RNA sensors. Publicly Accessible Penn Dissertations. (Fall 2010).
Jasin et al.: Democratization of gene editing: Insights from site-specific cleavage and double-strand break repair. DNA Report (Amst) 44:6-16 (Aug. 2016).
Li et al.: An apolipoprotein E-mimetic stimulates axonal regeneration and remyelination after peripheral nerve injury. J. Pharm. & Experimental Therapeutics. 334(1):106-115 (Jul. 2010).
Life Technologies Corp. mMessage mMachine Kit (rev. F. Nov. 2011).
Lonza: General protocol for nucleofection of adherent cell lines. (2008).
Simões et al.: Human serum albumin enhances DNA transfection by lipoplexes and confers resistance to inhibition by serum. Biochim Biophys Acta.1463:459-469 (2000).
U.S. Appl. No. 90/019,127 Order Granting Request for Ex Parte Reexamination dated Jan. 31, 2023.
U.S. Appl. No. 90/019,127 Request for Ex Parte Examination of U.S. Pat. No. 10,662,410 dated Nov. 16, 2022.
U.S. Appl. No. 90/019,128 Order Granting Request for Ex Parte Reexamination dated Jan. 31, 2023.
U.S. Appl. No. 90/019,128 Request for Ex Parte Examination of U.S. Pat. No. 10,829,738 dated Nov. 16, 2022.
U.S. Appl. No. 90/019,129 Order Granting Request for Ex Parte Reexamination dated Jan. 31, 2023.
U.S. Appl. No. 90/019,129 Request for Ex Parte Examination of U.S. Pat. No. 10,982,229 dated Nov. 16, 2022.
U.S. Appl. No. 16/913,315 Office Action dated Nov. 25, 2022.

FIG. 3A
FIG. 3B
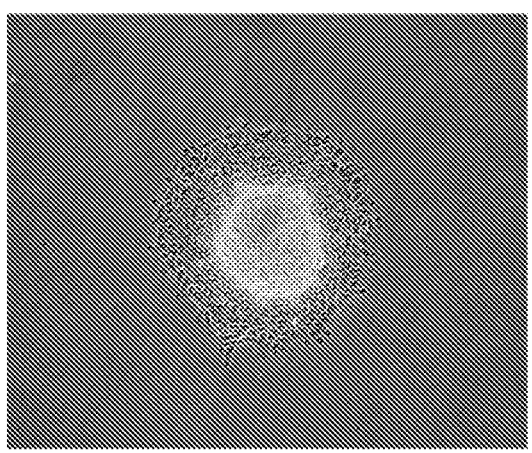
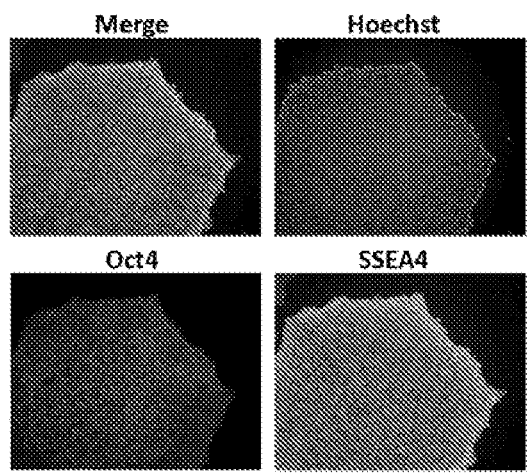
FIG. 3C
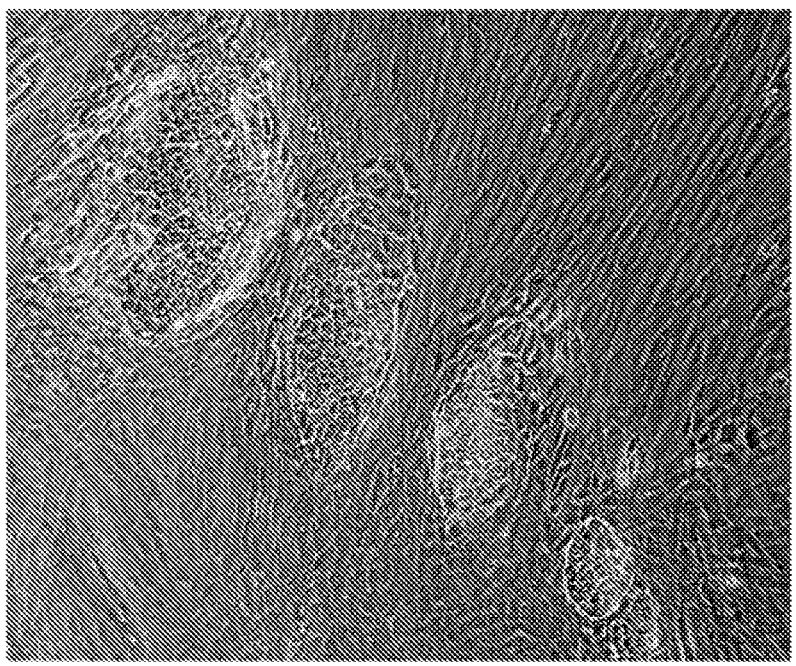

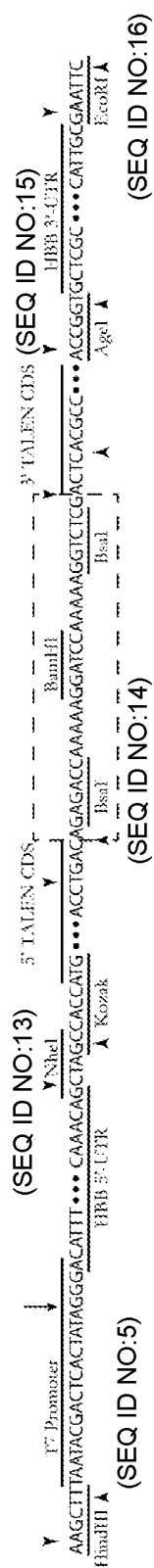
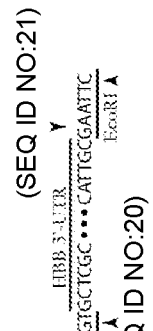
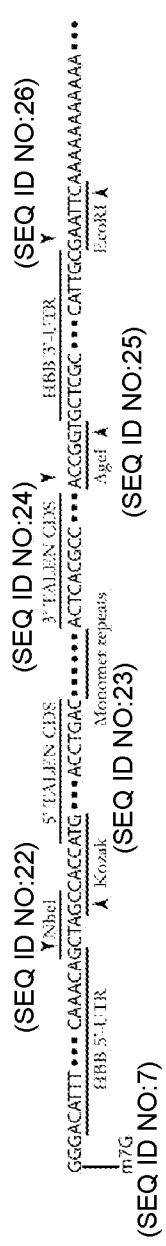
FIG. 6A
FIG. 6B
FIG. 6C

FIG. 7

```
TAATACGACTCACTATAGGGACATTTGCTTCTGACACAACTGTGTTCACTAGCAACCTCAAACAGCTAGC
CACCATGGACTATAAGGACCACGACGGAGACTACAAGGATCATGATATTGATTACAAAGACGATGACGAT
AAGATGGCCCCAAAGAAGAAGCGGAAGGTCGGTATCCACGGAGTCCCAGCAGCCGTAGATTTGAGAACTT
TGGGATATTCACAGCAGCAGCAGGAAAAGATCAAGCCCAAAGTGAGGTCGACAGTCGCGCAGCATCACGA
AGCGCTGGTGGGTCATGGGTTTACACATGCCCACATCGTAGCCTTGTCGCAGCACCCTGCAGCCCTTGGC
ACGGTCGCCGTCAAGTACCAGGACATGATTGCGGCGTTGCCGGAAGCCACACATGAGGCGATCGTCGGTG
TGGGGAAACAGTGGAGCGGAGCCCGAGCGCTTGAGGCCCTGTTGACGGTCGCGGGAGAGCTGAGAGGGCC
TCCCCTTCAGCTGGACACGGGCCAGTTGCTGAAGATCGCGAAGCGGGGAGGAGTCACGGCGGTCGAGGCG
GTGCACGCGTGGCGCAATGCGCTCACGGGAGCACCCCTCAACCTGACCCCAGAGCAGGTCGTGGCAATTG
CGAGCX(02)XGGGGGAAAGCAGGCACTCGAAACCGTCCAGAGGTTGCTGCCTGTGCTGTGCCAAGCGCA
CGGACTTACGCCAGAGCAGGTCGTGGCAATTGCGAGCX(03)XGGGGGAAAGCAGGCACTCGAAACCGTC
CAGAGGTTGCTGCCTGTGCTGTGCCAAGCGCACGGACTAACCCCAGAGCAGGTCGTGGCAATTGCGAGCX
(04)XGGGGGAAAGCAGGCACTCGAAACCGTCCAGAGGTTGCTGCCTGTGCTGTGCCAAGCGCACGGGTT
GACCCCAGAGCAGGTCGTGGCAATTGCGAGCX(05)XGGGGGAAAGCAGGCACTCGAAACCGTCCAGAGG
TTGCTGCCTGTGCTGTGCCAAGCGCACGGCCTGACCCCAGAGCAGGTCGTGGCAATTGCGAGCX(06)XG
GGGGAAAGCAGGCACTCGAAACCGTCCAGAGGTTGCTGCCTGTGCTGTGCCAAGCGCACGGACTGACACC
AGAGCAGGTCGTGGCAATTGCGAGCX(07)XGGGGGAAAGCAGGCACTCGAAACCGTCCAGAGGTTGCTG
CCTGTGCTGTGCCAAGCGCACGGACTTACACCCGAACAAGTCGTGGCAATTGCGAGCX(08)XGGGGGAA
AGCAGGCACTCGAAACCGTCCAGAGGTTGCTGCCTGTGCTGTGCCAAGCGCACGGACTTACGCCAGAGCA
GGTCGTGGCAATTGCGAGCX(09)XGGGGGAAAGCAGGCACTCGAAACCGTCCAGAGGTTGCTGCCTGTG
CTGTGCCAAGCGCACGGACTAACCCCAGAGCAGGTCGTGGCAATTGCGAGCX(10)XGGGGGAAAGCAGG
CACTCGAAACCGTCCAGAGGTTGCTGCCTGTGCTGTGCCAAGCGCACGGGTTGACCCCAGAGCAGGTCGT
GGCAATTGCGAGCX(11)XGGGGGAAAGCAGGCACTCGAAACCGTCCAGAGGTTGCTGCCTGTGCTGTGC
CAAGCGCACGGCCTGACCCCAGAGCAGGTCGTGGCAATTGCGAGCX(12)XGGGGGAAAGCAGGCACTCG
AAACCGTCCAGAGGTTGCTGCCTGTGCTGTGCCAAGCGCACGGACTGACACCAGAGCAGGTCGTGGCAAT
TGCGAGCX(13)XGGGGGAAAGCAGGCACTCGAAACCGTCCAGAGGTTGCTGCCTGTGCTGTGCCAAGCG
CACGGCCTCACCCCAGAGCAGGTCGTGGCAATTGCGAGCX(14)XGGGGGAAAGCAGGCACTCGAAACCG
TCCAGAGGTTGCTGCCTGTGCTGTGCCAAGCGCACGGACTTACGCCAGAGCAGGTCGTGGCAATTGCGAG
CX(15)XGGGGGAAAGCAGGCACTCGAAACCGTCCAGAGGTTGCTGCCTGTGCTGTGCCAAGCGCACGGA
CTAACCCCAGAGCAGGTCGTGGCAATTGCGAGCX(16)XGGGGGAAAGCAGGCACTCGAAACCGTCCAGA
GGTTGCTGCCTGTGCTGTGCCAAGCGCACGGGTTGACCCCAGAGCAGGTCGTGGCAATTGCGAGCX(17)
XGGGGGAAAGCAGGCACTCGAAACCGTCCAGAGGTTGCTGCCTGTGCTGTGCCAAGCGCACGGCCTGACC
CCAGAGCAGGTCGTGGCAATTGCGAGCX(18)XGGGGGAAAGCAGGCACTCGAAACCGTCCAGAGGTTGC
TGCCTGTGCTGTGCCAAGCGCACGGACTGACACCAGAGCAGGTCGTGGCAATTGCGAGCX(19)XGGGGG
AAAGCAGGCACTCGAAACCGTCCAGAGGTTGCTGCCTGTGCTGTGCCAAGCGCACGGACTCACGCCTGA
CAGGTAGTGGCTATTGCATCCX(20)XGGGGGCAGACCCGCACTGGAGTCAATCGTGGCCCAGCTTTCGA
GGCCGGACCCCGCGCTGGCCGCACTCACTAATGATCATCTTGTAGCGCTGGCCTGCCTCGGCGGACGACC
CGCCTTGGATGCGGTGAAGAAGGGGCTCCCGCACGCGCCTGCATTGATTAAGCGGACCAACAGAAGGATT
CCCGAGAGGACATCACATCGAGTGGCAGGTTCCCAACTCGTGAAGAGTGAACTTGAGGAGAAAAGTCGG
AGCTGCGGCACAAATTGAAATACGTACCGCATGAATACATCGAACTTATCGAAATTGCTAGGAACTCGAC
TCAAGACAGAATCCTTGAGATGAAGGTAATGGAGTTCTTTATGAAGGTTTATGGATACCGAGGGAAGCAT
CTCGGTGGATCACGAAAACCCGACGGAGCAATCTATACGGTGGGGAGCCCGATTGATTACGGAGTGATCG
TCGACACGAAAGCCTACAGCGGTGGGTACAATCTTCCCATCGGGCAGGCAGATGAGATGCAACGTTATGT
CGAAGAAAATCAGACCAGGAACAAACACATCAATCCAAATGAGTGGTGGAAAGTGTATCCTTCATCAGTG
ACCGAGTTTAAGTTTTTGTTTGTCTCTGGGCATTTCAAAGGCAACTATAAGGCCCAGCTCACACGGTTGA
ATCACATTACGAACTGCAATGGTGCGGTTTTGTCCGTAGAGGAACTGCTCATTGGTGGAGAAATGATCAA
AGCGGGAACTCTGACACTGGAAGAAGTCAGACGCAAGTTTAACAATGGCGAGATCAATTTCCGCTCATAA
ACCGGTGCTCGCTTTCTTGCTGTCCAATTTCTATTAAAGGTTCCTTTGTTCCCTAAGTCCAACTACTAAA
CTGGGGGATATTATGAAGGGCCTTGAGCATCTGGATTCTGCCTAATAAAAAACATTTATTTTCATTGC
```

```
Where X(02)X -> X(20)X are one of
AACATC    (RVD NI, matches A)
AACGGA    (RVD NG, matches T)
CATGAC    (RVD HD, matches C)
AACAAC    (RVD NN, matches G or A)
```

METHODS AND PRODUCTS FOR TRANSFECTING CELLS

CROSS REFERENCE TO RELATED APPLICATIONS

The present application is a continuation of U.S. patent application Ser. No. 16/857,894, filed Apr. 24, 2020, which is a continuation of U.S. patent application Ser. No. 16/776,765, filed Jan. 30, 2020 (now U.S. Pat. No. 10,662,410), which is a continuation of U.S. patent application Ser. No. 16/567,059, filed Sep. 11, 2019, which is a continuation of U.S. patent application Ser. No. 16/402,175, filed May 2, 2019 (now U.S. Pat. No. 10,472,611), which is a continuation of U.S. patent application Ser. No. 15/429,795, filed Feb. 10, 2017, which is a continuation of U.S. patent application Ser. No. 15/222,453, filed Jul. 28, 2016 (now U.S. Pat. No. 9,605,278), which is a continuation of U.S. patent application Ser. No. 14/296,220, filed Jun. 4, 2014 (now U.S. Pat. No. 9,422,577), which is a continuation of International Patent Application No. PCT/US2012/067966, filed on Dec. 5, 2012, which claims priority to U.S. Provisional Application No. 61/566,948, filed on Dec. 5, 2011, U.S. Provisional Application No. 61/569,595, filed on Dec. 12, 2011, U.S. Provisional Application No. 61/637,570, filed on Apr. 24, 2012, and U.S. Provisional Application No. 61/664,494, filed on Jun. 26, 2012, which are all hereby incorporated by reference in their entireties.

FIELD OF THE INVENTION

The present invention relates in part to nucleic acids encoding proteins, nucleic acids containing non-canonical nucleotides, therapeutics comprising nucleic acids, methods, kits, and devices for inducing cells to express proteins, methods, kits, and devices for transfecting, gene editing, and reprogramming cells, and cells, organisms, and therapeutics produced using these methods, kits, and devices.

DESCRIPTION OF THE TEXT FILE SUBMITTED ELECTRONICALLY

This application contains a Sequence Listing in ASCII format submitted electronically herewith via EFS-Web. Said ASCII copy, created on Jun. 17, 2020, is named FAB-001C12_ST25.txt and is 26,783 bytes in size. The Sequence Listing is incorporated herein by reference in its entirety.

BACKGROUND

Nucleic-Acid Transfection

Nucleic acids can be delivered to cells both in vitro and in vivo by pre-complexing the nucleic acids with charged lipids, lipidoids, peptides, polymers or mixtures thereof. Such transfection reagents are commercially available, and are widely used for delivering nucleic acids to cells in culture. Cells exposed to transfection reagent-nucleic acid complexes may internalize these complexes by endocytosis or other means. Once inside a cell, the nucleic acid can carry out its intended biological function. In the case of protein-encoding RNA, for example, the RNA can be translated into protein by the ribosomes of the cell.

Serum-Free Cell Culture

Animal sera such as fetal bovine serum (FBS) are commonly used as a supplement in cell-culture media to promote the growth of many types of cells. However, the undefined nature of serum makes cells that are contacted with this component undesirable for both research and therapeutic applications. As a result, serum-free cell-culture media have been developed to eliminate the batch-to-batch variability and the risk of contamination with toxic and/or pathogenic substances that are associated with serum.

The most abundant protein in serum is serum albumin. Serum albumin binds to a wide variety of molecules both in vitro and in vivo, including hormones, fatty acids, calcium and metal ions, and small-molecule drugs, and can transport these molecules to cells, both in vitro and in vivo. Serum albumin (most often either bovine serum albumin (BSA) or human serum albumin (HSA)) is a common ingredient in serum-free cell-culture media, where it is typically used at a concentration of 1-10 g/L. Serum albumin is traditionally prepared from blood plasma by ethanol fractionation (the "Cohn" process). The fraction containing serum albumin ("Cohn Fraction V" or simply "Fraction V") is isolated, and is typically used without further treatment. Thus, standard preparations of serum albumin comprise a protein part (the serum albumin polypeptide) and an associated-molecule part (including salts, fatty acids, etc. that are bound to the serum albumin polypeptide). The composition of the associated-molecule component of serum albumin is, in general, complex and unknown.

Serum albumin can be treated for use in certain specialized applications (See Barker A method for the deionization of bovine serum albumin. Tissue Culture Association. 1975; Droge et al. Biochem Pharmacol. 1982; 31:3775-9; Ng et al. Nat Protoc. 2008; 3:768-76; US Patent Appl. Pub. No. US 2010/0168000, the contents of which are hereby incorporated by reference). These treatment processes are most commonly used to remove globulins and contaminating viruses from solutions of serum albumin, and often include stabilization of the serum albumin polypeptide by addition of the short-chain fatty acid, octanoic acid, followed by heat-inactivation/precipitation of the contaminants. For highly specialized stem-cell-culture applications, using an ion-exchange resin to remove excess salt from solutions of BSA has been shown to increase cell viability (See Ng et al. Nat Protoc. 2008; 3:768-76; US Patent Appl. Pub. No. US 2010/0168000, the contents of which are hereby incorporated by reference). However, recombinant serum albumin does not benefit from such treatment, even in the same sensitive stem-cell-culture applications (See Ng et al. Nat Protoc. 2008; 3:768-76; US Patent Appl. Pub. No. US 2010/0168000, the contents of which are hereby incorporated by reference), demonstrating that the effect of deionization in these applications is to remove excess salt from the albumin solution, and not to alter the associated-molecule component of the albumin. In addition, the effect of such treatment on other cell types such as human fibroblasts, and the effect of such treatment on transfection efficiency and transfection-associated toxicity have not been previously explored. Furthermore, albumin-associated lipids have been shown to be critical for human pluripotent stem-cell culture, and removing these from albumin has been shown to result in spontaneous differentiation of human pluripotent stem cells, even when lipids are added separately to the cell-culture medium (See Garcia-Gonzalo et al. PLoS One. 2008; 3:e1384, the contents of which are hereby incorporated by reference). Thus, a cell-culture medium containing albumin with an unmodified associated-molecule component is thought to be critical for the culture of human pluripotent stem cells. Importantly, the relationship between the associated-molecule component of lipid carriers such as albumin and transfection efficiency and transfection-associated toxicity has not been previously explored.

Cell Reprogramming

Cells can be reprogrammed by exposing them to specific extracellular cues and/or by ectopic expression of specific proteins, microRNAs, etc. While several reprogramming methods have been previously described, most that rely on ectopic expression require the introduction of exogenous DNA, which can carry mutation risks. DNA-free reprogramming methods based on direct delivery of reprogramming proteins have been reported, however these methods are too inefficient and unreliable for commercial use. In addition, RNA-based reprogramming methods have been described, however, existing RNA-based reprogramming methods are slow, unreliable, and inefficient when performed on adult cells, require many transfections (resulting in significant expense and opportunity for error), can reprogram only a limited number of cell types, can reprogram cells to only a limited number of cell types, require the use of immunosuppressants, and require the use of multiple human-derived components, including blood-derived HSA and human fibroblast feeders. The many drawbacks of previously disclosed cell-reprogramming methods make them undesirable for both research and therapeutic use.

Gene Editing

Several naturally occurring proteins contain DNA-binding domains that can recognize specific DNA sequences, for example, zinc fingers (ZFs) and transcription activator-like effectors (TALEs). Fusion proteins containing one or more DNA-binding domains and the catalytic domain of a nuclease can be used to create a double-strand break in a desired region of DNA in a cell. When combined with a DNA template containing one or more regions of homology to the DNA of the cell, gene-editing proteins can be used to insert a DNA sequence or to otherwise alter the sequence of the DNA of the cell in a controlled manner. However, most current methods for gene editing cells use DNA-based vectors to express gene-editing proteins. As a result, these gene-editing methods are inefficient, and carry a risk of uncontrolled mutagenesis, making them undesirable for both research and therapeutic use. Methods for DNA-free gene editing of somatic cells have not been previously explored, nor have methods for simultaneous or sequential gene editing and reprogramming of somatic cells. Finally, the use of gene editing in an anti-bacterial, anti-viral, or anti-cancer treatment has not been previously explored.

Model Organisms

Knockout rats have been generated by embryo microinjection of nucleic acids encoding zinc-finger nucleases and TALE-nucleases (TALENs). Gene editing to introduce sequence-specific mutations (a.k.a. "knockins") has also been reported in mice and rats by injecting nucleic acids encoding zinc-finger nucleases into embryos. Geneticallymodified rats have been generated using embryonic stem cells, and germline-competent rat pluripotent stem cells have been generated by somatic-cell reprogramming. However, the use of gene-edited reprogrammed cells to generate genetically modified organisms, including mice and rats has not been previously explored.

There is a need in the field for improved methods and products for transfecting cells.

SUMMARY OF THE INVENTION

Accordingly, the present invention provides reagents, protocols, kits, and devices for inducing cells to express proteins and for transfecting, reprogramming, and geneediting cells. Unlike previously reported methods, certain embodiments of the present invention do not involve exposing the cells to exogenous DNA or to allogeneic or animalderived materials.

In one aspect, the invention provides a synthetic RNA molecule comprising three or more non-canonical nucleotides that each include one or more substitutions from the following: pyrimidine position 2C, pyrimidine position 4C, pyrimidine position 5C, purine position 6C, purine position 7N, and purine position 8C. In some embodiments, the synthetic RNA molecule is produced by in vitro transcription. In other embodiments, the synthetic RNA molecule further comprises at least one of: a 5'-cap, a 5'-Cap 1 structure, and a 3'-poly(A) tail. In other embodiments, at least two of the non-canonical nucleotides are pyrimidines. In still other embodiments, the non-canonical nucleotides include at least one of pseudouridine, 2-thiouridine, 4-thiouridine, 5-azauridine, 5-hydroxyuridine, 5-aminouridine, 5-methyluridine, 2-thiopseudouridine, 4-thiopseudouridine, 5-hydroxypseudouridine, 5-methylpseudouridine, 5-aminopseudouridine, pseudoisocytidine, 5-methylcytidine, N4-methylcytidine, 2-thiocytidine, 5-azacytidine, 5-hydroxycytidine, 5-aminocytidine, N4-methylpseudoisocytidine, 2-thiopseudoisocytidine, 5-hydroxypseudoisocytidine, 5-aminopseudoisocytidine, 5-methylpseudoisocytidine, N6-methyladenosine, 7-deazaadenosine, 6-thioguanosine, 7-deazaguanosine, 8-azaguanosine, 6-thio-7-deazaguanosine, 6-thio-8-azaguanosine, 7-deaza-8-azaguanosine, and 6-thio-7-deaza-8-azaguanosine. In other embodiments, at least two of the non-canonical nucleotides each comprise less than 20% of the synthetic RNA molecule. In still other embodiments, the non-canonical nucleotides include at least one of: pseudouridine, 2-thiouridine, 4-thiouridine, 5-azauridine, 5-hydroxyuridine, 5-aminouridine, 5-methyluridine, 2-thiopseudouridine, 4-thiopseudouridine, 5-hydroxypseudouridine, 5-methylpseudouridine, and 5-aminopseudouridine, and at least one of: pseudoisocytidine, 5-methylcytidine, N4-methylcytidine, 2-thiocytidine, 5-azacytidine, 5-hydroxycytidine, 5-aminocytidine, N4-methylpseudoisocytidine, 2-thiopseudoisocytidine, 5-hydroxypseudoisocytidine, 5-aminopseudoisocytidine, and 5-methylpseudoisocytidine. In a further embodiment, the non-canonical nucleotides further include at least one of: N6-methyladenosine, 7-deazaadenosine, 6-thioguanosine, 7-deazaguanosine, 8-azaguanosine, 6-thio-7-deazaguanosine, 6-thio-8-azaguanosine, 7-deaza-8-azaguanosine, and 6-thio-7-deaza-8-azaguanosine.

In another aspect, the invention provides a synthetic RNA molecule that comprises a non-canonical nucleotide, and encodes a gene-editing protein.

In another embodiment, the invention provides a therapeutic composition comprising the synthetic RNA molecule described herein.

In another aspect, the invention provides a therapeutic composition comprising a synthetic RNA molecule that encodes a gene-editing protein and a transfection reagent.

In another embodiment, the invention provides a method for transfecting a cell with a nucleic acid comprising contacting the cell with the synthetic RNA molecule described herein.

In another embodiment, the invention provides a method for inducing a mammalian cell to express a protein of interest comprising contacting the cell with the synthetic RNA molecules described herein. In another embodiment, the invention provides a method for reprogramming a cell comprising contacting the cell with the synthetic RNA molecules described herein. In another embodiment, the invention provides a method for gene-editing a cell comprising contacting the cell with the synthetic RNA molecules described herein.

In another aspect, the invention provides a method for transfecting a cell with a nucleic acid comprising: contacting the cell with a medium containing hydrocortisone and/or albumin, wherein the albumin is treated with an ion-exchange resin or charcoal, and contacting the cell with the nucleic acid. In one embodiment, the albumin is treated with a short-chain fatty acid, and/or brought to a temperature of at least 40° C. In other embodiments, the method further comprises contacting the cell with a transfection reagent. In other embodiments, the cell is a mammalian cell, and the mammalian cell is induced to express a protein of interest. In other embodiments, the method further comprises contacting the cell with the nucleic acid at least twice during 5 consecutive days. In some embodiments, the nucleic acid encodes a reprogramming protein. In other embodiments, the cell is reprogrammed. In yet another embodiment, the cell is a skin cell, and further comprising culturing the skin cell under conditions that support the growth of at least one of: skin cells, pluripotent stem cells, glucose-responsive insulin-producing cells, hematopoietic cells, cardiac cells, and retinal cells, and wherein the skin cell is reprogrammed to a cell selected from: a skin cell, a pluripotent stem cell, a glucose-responsive insulin-producing cell, a hematopoietic cell, a cardiac cell, and a retinal cell. In yet another embodiment, the nucleic acid encodes Oct4 protein. In yet another embodiment, the method further comprises contacting the cell with a nucleic acid that encodes at least one of: Sox2 protein, Klf4 protein, and c-Myc protein. In yet another embodiment, the method further comprises contacting the cell with one or more nucleic acids that encode Sox2 protein, Klf4 protein, and c-Myc protein. In still other embodiments, the nucleic acid encodes a gene-editing protein. In still other embodiments, the nucleic acid encodes a protein that, acting alone or in combination with one or more other molecules, creates a single-strand or double-strand break in a DNA molecule. In various embodiments, the cell is gene-edited. In some embodiments, the single-strand or double-strand break is within about 5,000,000 bases of the transcription start site of a gene selected from: CCR5, CXCR4, GAD1, GAD2, CFTR, HBA1, HBA2, HBB, HBD, FANCA, XPA, XPB, XPC, ERCC2, POLH, HTT, DMD, SOD1, APOE, APP, LRRK2, PRNP, BRCA1, and BRCA2 or an analogue, variant or family-member thereof. In some embodiments, the method further comprises contacting the cell with at least one of: poly-L-lysine, poly-L-ornithine, RGD peptide, fibronectin, vitronectin, collagen, and laminin, or a biologically active fragment, functional variant or family-member thereof. In still other embodiments, the nucleic acid is a synthetic RNA molecule, which may contain at least one of: pseudouridine, 5-methylpseudouridine, and 5-methylcytidine. In some embodiments, the method provides for contacting the cell with a differentiation factor and/or harvesting the cell from a patient and/or delivering the cell to a patient.

In another aspect, the invention provides a medium comprising albumin, wherein the albumin is recombinant, and treated with an ion-exchange resin or charcoal. In another embodiment, the medium further comprises a buffered salt solution and amino acids and/or one or more of insulin, transferrin, and selenium and/or cholesterol and/or a steroid (such as, for example, hydrocortisone) and/or an immunosuppressant (such as, for example, B18R).

In another aspect, the invention provides a kit comprising hydrocortisone and/or albumin, wherein the albumin is treated with an ion-exchange resin or charcoal, and a synthetic RNA molecule. In one embodiment, the synthetic RNA molecule encodes at least one of: Oct4 protein, Sox2 protein, Klf4 protein, c-Myc protein, Nanog protein, Lin28 protein, and Utf1 protein. In another embodiment, the kit further comprises a transfection reagent and/or the synthetic RNA molecules described herein. In another embodiment, the kit is a reprogramming kit and/or a gene-editing kit.

In another aspect, the invention provides a nucleic acid transfection-reagent complex comprising a nucleic acid and a transfection reagent, wherein the nucleic acid transfection-reagent complex is solidified by cooling. In some embodiments, the nucleic acid transfection-reagent complex is solidified by contacting the nucleic acid transfection-reagent complex with liquid nitrogen in the liquid and/or vapor phase.

In another aspect, the invention provides a method for transfecting a cell comprising contacting the cell with the nucleic acid transfection-reagent complex described herein.

In another aspect, the invention provides a system for transfecting cells comprising a means for contacting cells with a transfection medium and a means for contacting the cells with nucleic acid transfection-reagent complexes. In some embodiments, the atmosphere around the cells contains approximately 5% carbon dioxide and/or approximately 5% oxygen.

In some embodiments, the invention provides a cell and/or an organism and/or a therapeutic composition and/or a therapeutic composition comprising a cell produced by the methods described herein.

In some aspects, synthetic RNA molecules with low toxicity and high translation efficiency are provided. In other aspects, methods, kits, and devices for producing and delivering synthetic RNA molecules to cells are provided. In still other aspects, a cell-culture medium for high-efficiency transfection, reprogramming, and gene editing of cells is provided. Other aspects relate to therapeutics comprising synthetic RNA molecules, including for the treatment of type 1 diabetes, heart disease, including ischemic and dilated cardiomyopathy, macular degeneration, Parkinson's disease, cystic fibrosis, sickle-cell anemia, thalassemia, Fanconi anemia, severe combined immunodeficiency, hereditary sensory neuropathy, xeroderma pigmentosum, Huntington's disease, muscular dystrophy, amyotrophic lateral sclerosis, Alzheimer's disease, cancer, and infectious diseases including hepatitis and HIV/AIDS. Further aspects relate to therapeutics comprising cells, including for the treatment of type 1 diabetes, heart disease, including ischemic and dilated cardiomyopathy, macular degeneration, Parkinson's disease, cystic fibrosis, sickle-cell anemia, thalassemia, Fanconi anemia, severe combined immunodeficiency, hereditary sensory neuropathy, xeroderma pigmentosum, Huntington's disease, muscular dystrophy, amyotrophic lateral sclerosis, Alzheimer's disease, cancer, and infectious diseases including hepatitis and HIV/AIDS.

DETAILED DESCRIPTION OF THE FIGURES

The present invention is illustrated by way of example, and not by way of limitation, in the figures of the accompanying drawings and in which:

FIG. 1 depicts RNA encoding the indicated proteins, resolved on a denaturing formaldehyde-agarose gel.

FIG. 2A depicts primary human fibroblasts, transfected with synthetic RNA encoding Oct4 and comprising the indicated nucleotides. "A" refers to adenosine, "G" refers to guanosine, "U" refers to uridine, "C" refers to cytidine, "psU" refers to pseudouridine, "5mC" refers to 5-methylcytidine, "N4mC" refers to N4-methylcytidine, "7dG" refers to 7-deazaguanosine, and "psisoC" refers to pseudoisocytidine. Numbers preceding nucleotides indicate the fraction of the corresponding nucleotide-5'-triphosphate in the in vitro-transcription reaction. For example, 0.5 N4mC refers to RNA synthesized in an in vitro-transcription reaction containing equal amounts of N4-methylcytidine-5'-triphosphate and cytidine-5'-triphosphate. Cells were fixed and stained for Oct4 protein 20 h after transfection.

FIG. 2B depicts Oct4 expression and cell density of cultures of primary human fibroblasts, transfected with synthetic RNA encoding Oct4 and comprising the indicated nucleotides. Nucleotides are abbreviated as in FIG. 2A, except that "7dA" refers to 7-deazaadenosine, and "piC" refers to pseudoisocytidine. Cell density is shown normalized to untransfected cells. Oct4 expression is shown normalized to synthetic RNA containing only canonical nucleotides. Error bars indicate the standard error (n=3).

FIG. 3A depicts a reprogrammed cell line, generated by transfecting primary human fibroblasts with RNA encoding the proteins Oct4, Sox2, Klf4, c-Myc-2 (T58A), and Lin28, one day after colonies were picked and plated on a basement membrane extract-coated plate.

FIG. 3B depicts a reprogrammed cell line, generated as in FIG. 3A, stained for the pluripotent stem-cell markers Oct4 and SSEA4. The panel labeled "Hoechst" shows the nuclei, and the panel labeled "Merge" shows the merged signals from the three channels.

FIG. 3C depicts primary human fibroblasts, transfected and cultured as in FIG. 3A. A total of 5 transfections were performed. Pictures were taken on day 7. Several colonies of cells with a reprogrammed morphology are visible.

Figure 4A:
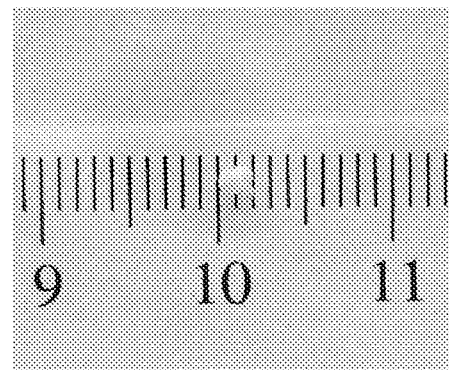

FIG. 4A depicts a 1.5 mm-diameter dermal punch biopsy tissue sample.

Figure 4B:
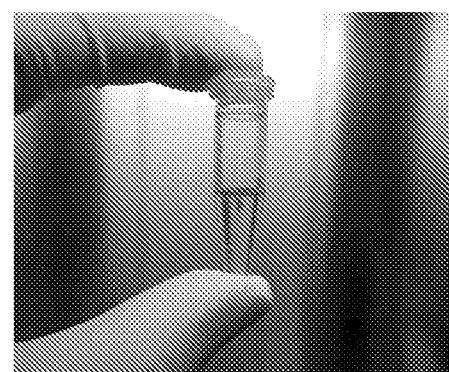

FIG. 4B depicts a tissue sample, harvested as in FIG. 4A, and suspended at the air-liquid interface of a solution containing an enzyme.

Figure 4C:
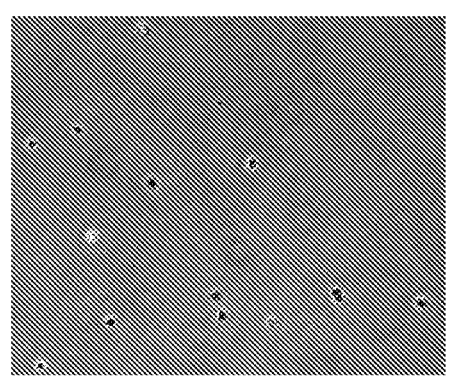

FIG. 4C depicts primary human fibroblasts, harvested as in FIG. 4A, dissociated as in FIG. 4B, and plated in a well of a 96-well plate.

Figure 5A:
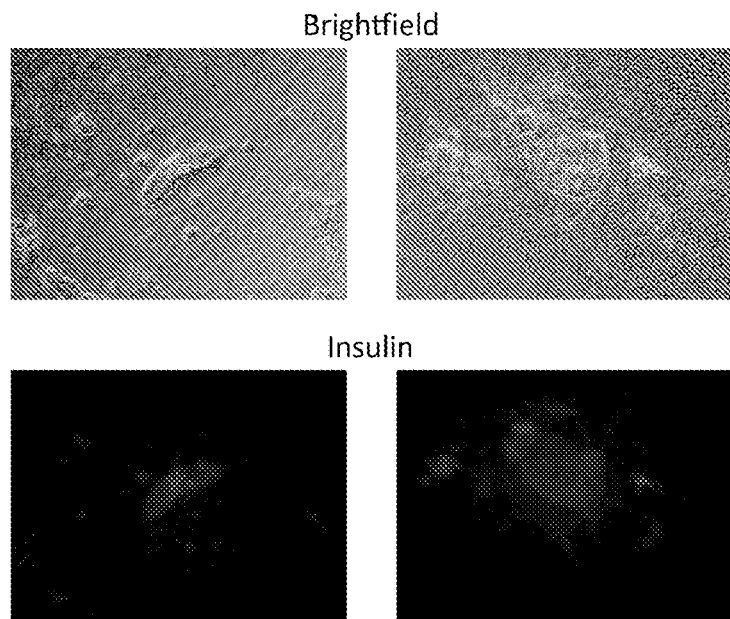

FIG. 5A depicts primary human fibroblasts, reprogrammed to insulin-producing cells. Cells were fixed and stained for insulin.

Figure 5B:
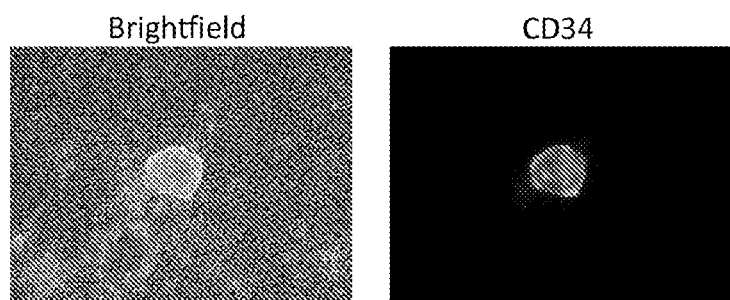

FIG. 5B depicts primary human fibroblasts, reprogrammed to hematopoietic cells. Cells were fixed and stained for CD34.

Figure 5C:
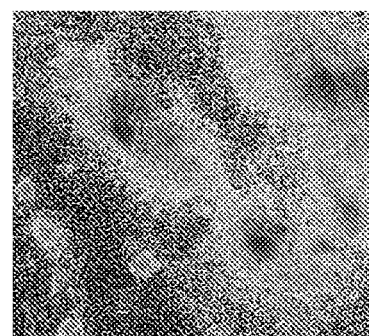

FIG. 5C depicts primary human fibroblasts, reprogrammed to beating cardiac cells.

FIG. 6A depicts the forward strand of an in vitro-transcription template for producing an RNA TALEN™ backbone.

FIG. 6B depicts the template of FIG. 6A after a Golden-Gate cloning reaction to incorporate a series of monomer repeats, forming a complete RNA TALEN™ template.

FIG. 6C depicts a 5'-capped, 3'-poly(A)-tailed RNA TALEN™ produced from the template of FIG. 6B.

FIG. 7 depicts the sequence of the template of FIG. 6B, wherein the RNA TALEN™ is designed to bind to a 20 bp region of DNA, and wherein the regions labeled "X(02)X", "X(03)X", and so forth, represent the repeat variable domains (RVDs) that can be selected to target a specific DNA sequence. This template encodes an RNA TALEN™, wherein the first residue bound by the RNA TALEN™ is a thymidine residue, irrespective of the RVDs, and thus the first RVD is labeled "X(02)X" instead of "X(01)X".

Figure 8:
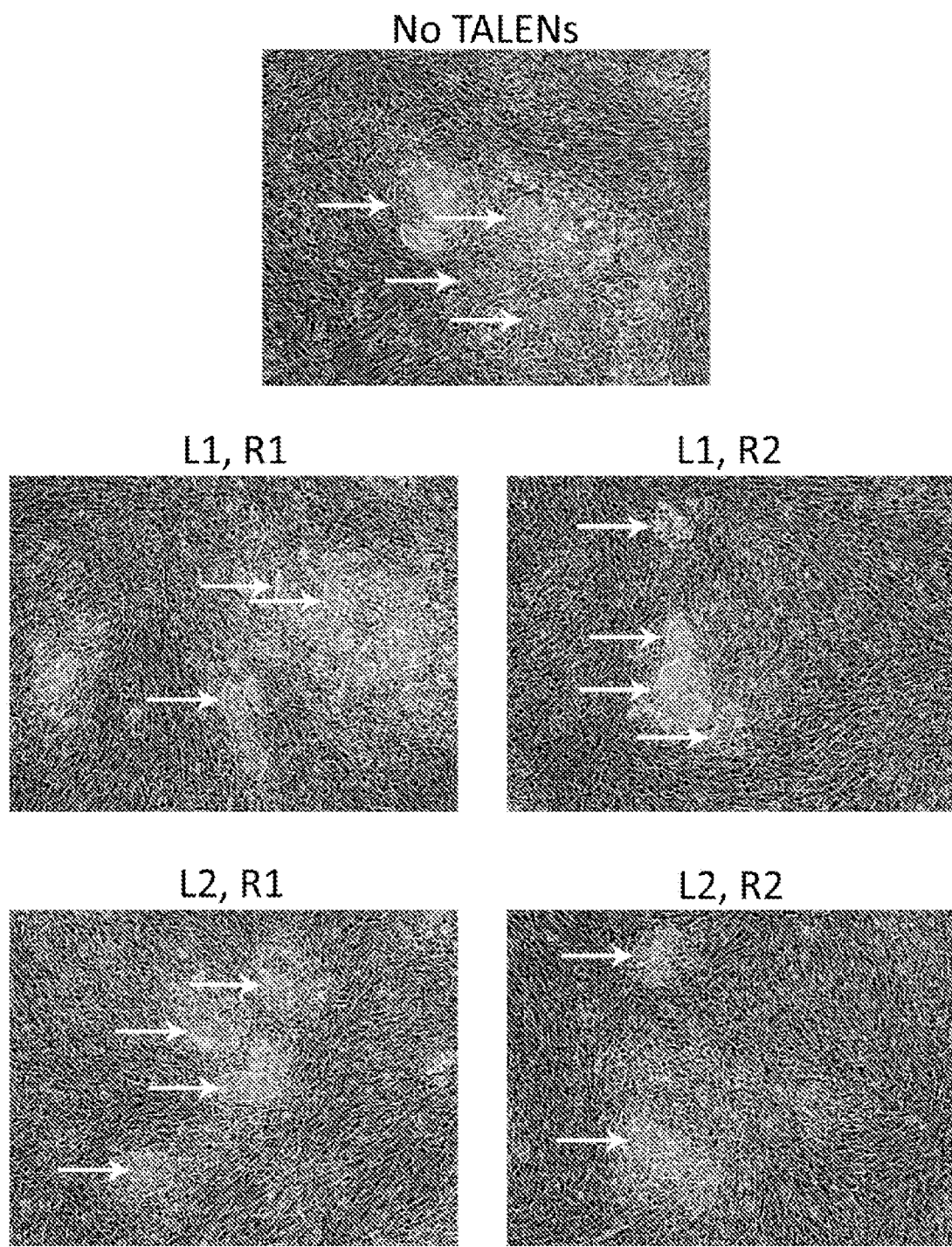

FIG. 8 depicts primary human fibroblasts, gene-edited and reprogrammed. Arrows indicate colonies of cells with a reprogrammed morphology.

Figure 9A:
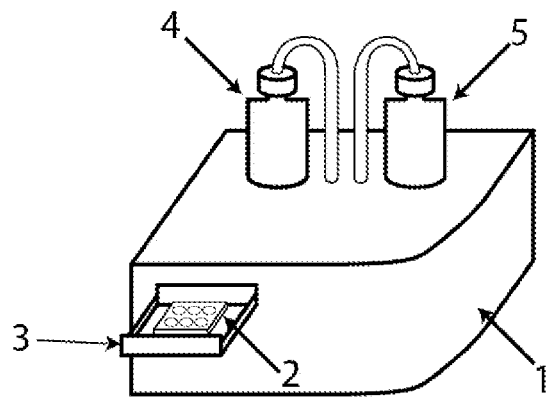

FIG. 9A depicts the front view of a system that can transfect and/or reprogram cells in an automated or semi-automated manner.

Figure 9B:
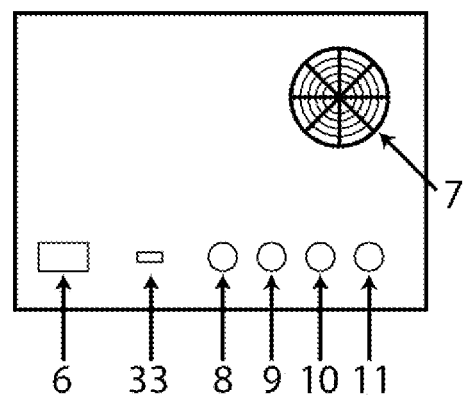

FIG. 9B depicts the back panel of the system of FIG. 9A.

Figure 9C:
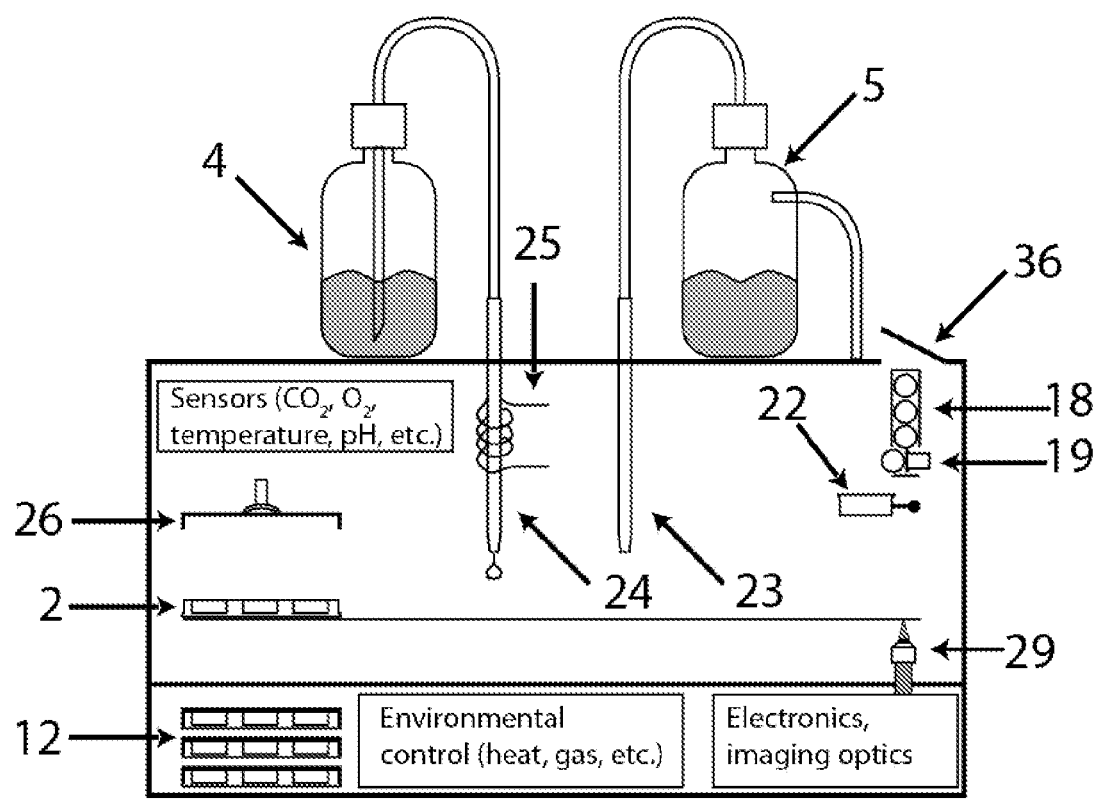

FIG. 9C depicts major components of the system of FIG. 9A.

Figure 10A:
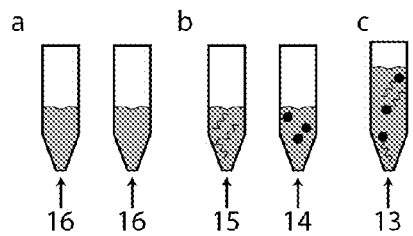

FIG. 10A depicts the complexation of RNA and a transfection reagent within a complexation medium.

Figure 10B:
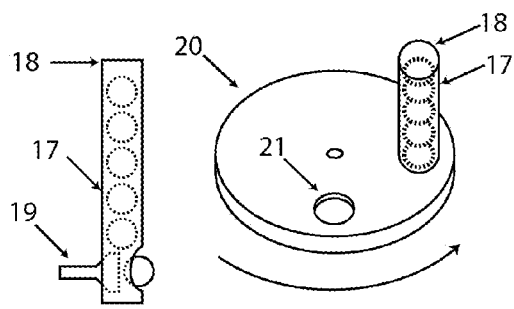

FIG. 10B depicts two methods for dispensing pre-complexed pellets containing nucleic acids.

Figure 10C:
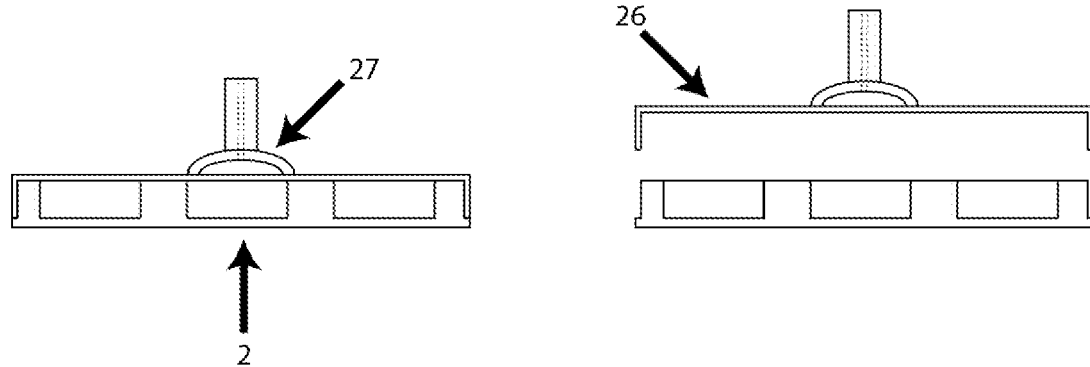

FIG. 10C depicts a method for removing the lid from a well plate using suction.

Figure 10D:
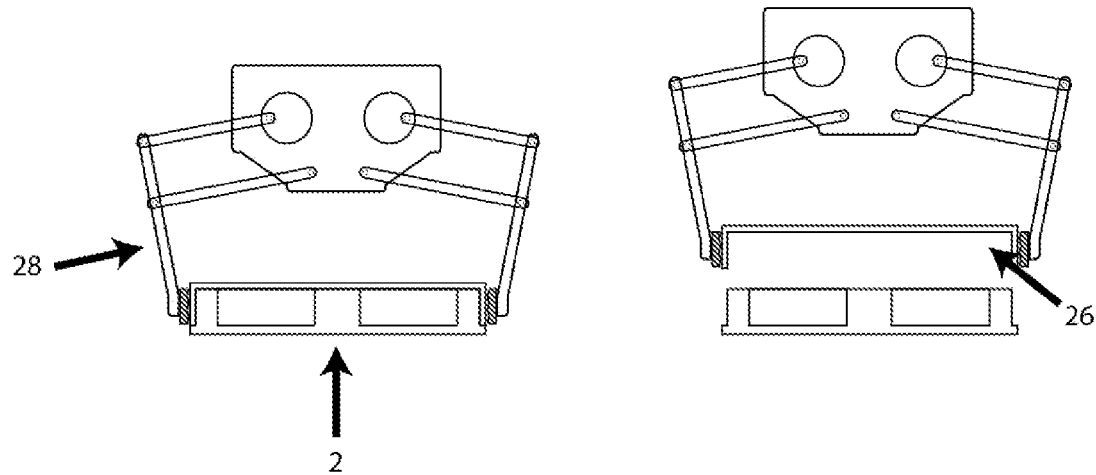

FIG. 10D depicts a method for removing the lid from a well plate using a gripper.

Figure 11:
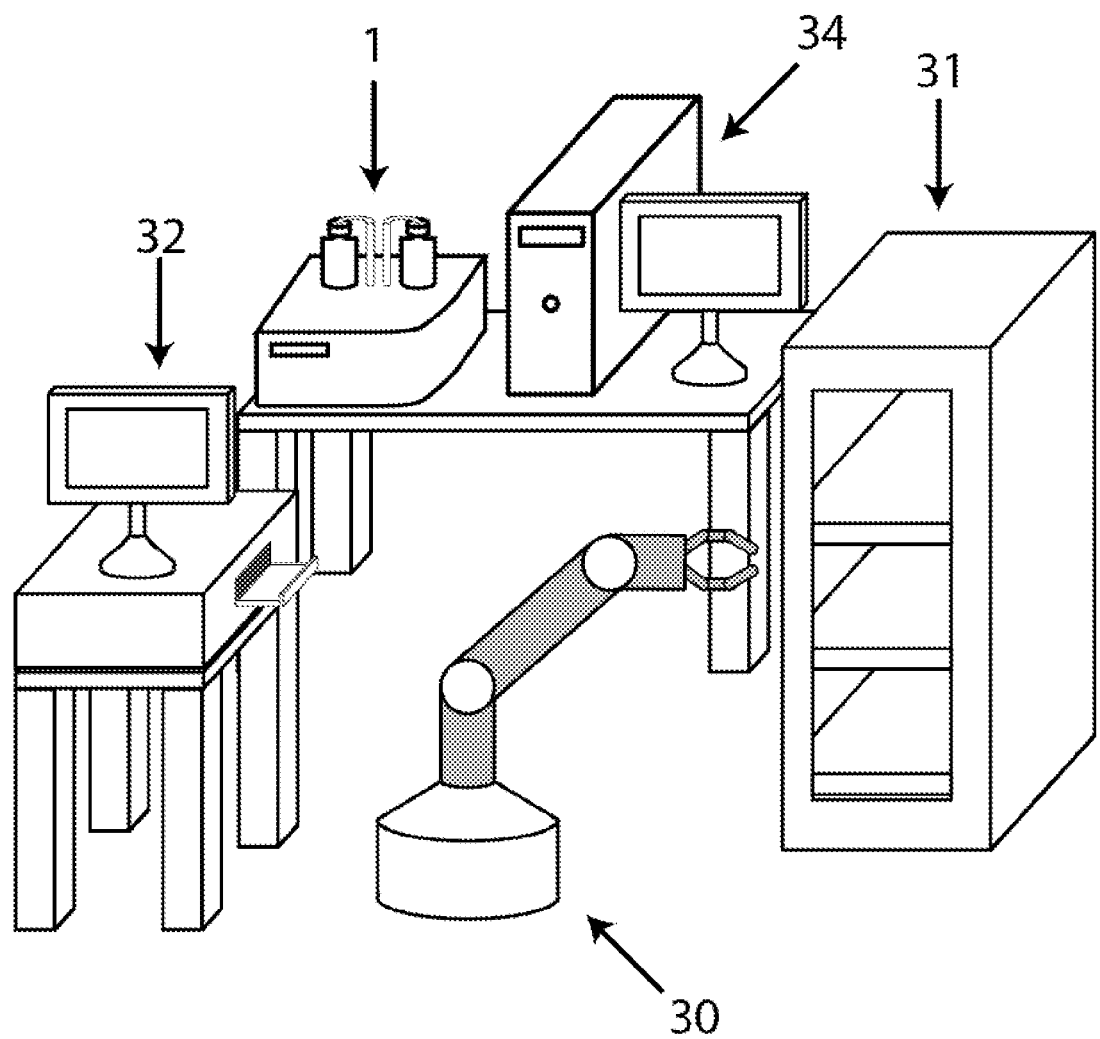

FIG. 11 depicts a system that can transfect and/or reprogram cells in an automated or semi-automated manner in operable combination with equipment for imaging, incubating, and otherwise manipulating the cells.

DEFINITIONS

By "molecule" is meant a molecular entity (molecule, ion, complex, etc.).

By "protein" is meant a polypeptide.

By "RNA molecule" is meant a molecule that comprises RNA.

By "synthetic RNA molecule" is meant an RNA molecule that is produced outside of a cell or that is produced inside of a cell using bioengineering, for example, an RNA molecule that is produced in an in vitro-transcription reaction, an RNA molecule that is produced by direct chemical synthesis or an RNA molecule that is produced in a genetically-engineered E. coli cell.

By "nucleotide" is meant a nucleotide or a fragment or derivative thereof, for example, a nucleobase, a nucleoside, a nucleotide-triphosphate, etc.

By "nucleoside" is meant a nucleotide.

By "transfection" is meant contacting a cell with a molecule, wherein the molecule is internalized by the cell.

By "upon transfection" is meant during or after transfection.

By "transfection reagent" is meant a substance or mixture of substances that associates with a molecule and facilitates the delivery of the molecule to and/or internalization of the molecule by a cell, for example, a cationic lipid, a charged polymer or a cell-penetrating peptide.

By "reagent-based transfection" is meant transfection using a transfection reagent.

By "cell-culture medium" is meant a medium that can be used for cell culture, for example, Dulbecco's Modified Eagle's Medium (DMEM) or DMEM+10% fetal bovine serum (FBS).

By "complexation medium" is meant a medium to which a transfection reagent and a molecule to be transfected are added and in which the transfection reagent associates with the molecule to be transfected.

By "transfection medium" is meant a medium that can be used for transfection, for example, Dulbecco's Modified Eagle's Medium (DMEM) or DMEM/F12.

By "recombinant protein" is meant a protein or peptide that is not produced in animals or humans. Non-limiting examples include human transferrin that is produced in bacteria, human fibronectin that is produced in an in vitro culture of mouse cells, and human serum albumin that is produced in a rice plant.

By "lipid carrier" is meant a substance that can increase the solubility of a lipid or lipid-soluble molecule in an aqueous solution, for example, human serum albumin or methyl-beta-cyclodextrin.

By "Oct4 protein" is meant a protein that is encoded by the POU5F1 gene, or a natural or engineered variant, family-member, orthologue, fragment or fusion construct thereof, for example, human Oct4 protein (SEQ ID NO:1), mouse Oct4 protein, Oct1 protein, a protein encoded by POU5F1 pseudogene 2, a DNA-binding domain of Oct4 protein or an Oct4-GFP fusion protein. In some embodiments the Oct4 protein comprises an amino acid sequence that has at least 70% identity with SEQ ID NO:1, or in other embodiments, at least 75%, 80%, 85%, 90%, or 95% identity with SEQ ID NO:1. In some embodiments, the Oct4 protein comprises an amino acid sequence having from 1 to 20 amino acid insertions, deletions, or substitutions (collectively) with respect to SEQ ID NO:1. In other embodiments, the Oct4 protein comprises an amino acid sequence having from 1 to 15 or from 1 to 10 amino acid insertions, deletions, or substitutions (collectively) with respect to SEQ ID NO:1.

By "Sox2 protein" is meant a protein that is encoded by the SOX2 gene, or a natural or engineered variant, family-member, orthologue, fragment or fusion construct thereof, for example, human Sox2 protein (SEQ ID NO:2), mouse Sox2 protein, a DNA-binding domain of Sox2 protein or a Sox2-GFP fusion protein. In some embodiments the Sox2 protein comprises an amino acid sequence that has at least 70% identity with SEQ ID NO:2, or in other embodiments, at least 75%, 80%, 85%, 90%, or 95% identity with SEQ ID NO:2. In some embodiments, the Sox2 protein comprises an amino acid sequence having from 1 to 20 amino acid insertions, deletions, or substitutions (collectively) with respect to SEQ ID NO:2. In other embodiments, the Sox2 protein comprises an amino acid sequence having from 1 to 15 or from 1 to 10 amino acid insertions, deletions, or substitutions (collectively) with respect to SEQ ID NO:2.

By "Klf4 protein" is meant a protein that is encoded by the KLF4 gene, or a natural or engineered variant, family-member, orthologue, fragment or fusion construct thereof, for example, human Klf4 protein (SEQ ID NO:3), mouse Klf4 protein, a DNA-binding domain of Klf4 protein or a Klf4-GFP fusion protein. In some embodiments the Klf4 protein comprises an amino acid sequence that has at least 70% identity with SEQ ID NO:3, or in other embodiments, at least 75%, 80%, 85%, 90%, or 95% identity with SEQ ID NO:3. In some embodiments, the Klf4 protein comprises an amino acid sequence having from 1 to 20 amino acid insertions, deletions, or substitutions (collectively) with respect to SEQ ID NO:3. In other embodiments, the Klf4 protein comprises an amino acid sequence having from 1 to 15 or from 1 to 10 amino acid insertions, deletions, or substitutions (collectively) with respect to SEQ ID NO:3.

By "c-Myc protein" is meant a protein that is encoded by the MYC gene, or a natural or engineered variant, family-member, orthologue, fragment or fusion construct thereof, for example, human c-Myc protein (SEQ ID NO:4), mouse c-Myc protein, 1-Myc protein, c-Myc (T58A) protein, a DNA-binding domain of c-Myc protein or a c-Myc-GFP fusion protein. In some embodiments the c-Myc protein comprises an amino acid sequence that has at least 70% identity with SEQ ID NO:4, or in other embodiments, at least 75%, 80%, 85%, 90%, or 95% identity with SEQ ID NO:4. In some embodiments, the c-Myc protein comprises an amino acid having from 1 to 20 amino acid insertions, deletions, or substitutions (collectively) with respect to SEQ ID NO:4. In other embodiments, the c-Myc protein comprises an amino acid sequence having from 1 to 15 or from 1 to 10 amino acid insertions, deletions, or substitutions (collectively) with respect to SEQ ID NO:4.

By "reprogramming" is meant causing a change in the phenotype of a cell, for example, causing a β-cell progenitor to differentiate into a mature β-cell, causing a fibroblast to dedifferentiate into a pluripotent stem cell, causing a keratinocyte to transdifferentiate into a cardiac stem cell or causing the axon of a neuron to grow.

By "reprogramming factor" is meant a molecule that, when a cell is contacted with the molecule and/or the cell expresses the molecule, can, either alone or in combination with other molecules, cause reprogramming, for example, Oct4 protein.

By "feeder" is meant a cell that can be used to condition medium or to otherwise support the growth of other cells in culture.

By "conditioning" is meant contacting one or more feeders with a medium.

By "fatty acid" is meant a molecule that comprises an aliphatic chain of at least two carbon atoms, for example, linoleic acid, α-linolenic acid, octanoic acid, a leukotriene, a prostaglandin, cholesterol, a glucocorticoid, a resolvin, a protectin, a thromboxane, a lipoxin, a maresin, a sphingolipid, tryptophan, N-acetyl tryptophan or a salt, methyl ester or derivative thereof.

By "short-chain fatty acid" is meant a fatty acid that comprises an aliphatic chain of between two and 30 carbon atoms.

By "albumin" is meant a protein that is highly soluble in water, for example, human serum albumin.

By "associated molecule" is meant a molecule that is non-covalently bound to another molecule.

By "associated-molecule-component of albumin" is meant one or more molecules that are bound to an albumin polypeptide, for example, lipids, hormones, cholesterol, calcium ions, etc. that are bound to an albumin polypeptide.

By "treated albumin" is meant albumin that is treated to reduce, remove, replace or otherwise inactivate the associated-molecule-component of the albumin, for example, human serum albumin that is incubated at an elevated temperature, human serum albumin that is contacted with sodium octanoate or human serum albumin that is contacted with a porous material.

By "ion-exchange resin" is meant a material that, when contacted with a solution containing ions, can replace one or more of the ions with one or more different ions, for example, a material that can replace one or more calcium ions with one or more sodium ions.

By "germ cell" is meant a sperm cell or an egg cell.

By "pluripotent stem cell" is meant a cell that can differentiate into cells of all three germ layers (endoderm, mesoderm, and ectoderm) in vivo.

By "somatic cell" is meant a cell that is not a pluripotent stem cell or a germ cell, for example, a skin cell.

By "glucose-responsive insulin-producing cell" is meant a cell that, when exposed to a certain concentration of glucose, can produce and/or secrete an amount of insulin that is different from (either less than or more than) the amount of insulin that the cell produces and/or secretes when the cell is exposed to a different concentration of glucose, for example, a β-cell.

By "hematopoietic cell" is meant a blood cell or a cell that can differentiate into a blood cell, for example, a hematopoietic stem cell or a white blood cell.

By "cardiac cell" is meant a heart cell or a cell that can differentiate into a heart cell, for example, a cardiac stem cell or a cardiomyocyte.

By "retinal cell" is meant a cell of the retina or a cell that can differentiate into a cell of the retina, for example, a retinal pigmented epithelial cell.

By "skin cell" is meant a cell that is normally found in the skin, for example, a fibroblast, a keratinocyte, a melanocyte, an adipocyte, a mesenchymal stem cell, an adipose stem cell or a blood cell.

By "Wnt signaling agonist" is meant a molecule that can perform one or more of the biological functions of one or more members of the Wnt family of proteins, for example, Wnt1, Wnt2, Wnt3, Wnt3a or 2-amino-4-[3,4-(methylenedioxy)benzylamino]-6-(3-methoxyphenyl)pyrimidine.

By "IL-6 signaling agonist" is meant a molecule that can perform one or more of the biological functions of IL-6 protein, for example, IL-6 protein or IL-6 receptor (also known as soluble IL-6 receptor, IL-6R, IL-6R alpha, etc.).

By "TGF-β signaling agonist" is meant a molecule that can perform one or more of the biological functions of one or more members of the TGF-β superfamily of proteins, for example, TGF-β1, TGF-β3, Activin A, BMP-4 or Nodal.

By "immunosuppressant" is meant a substance that can suppress one or more aspects of an immune system, and that is not normally present in a mammal, for example, B18R or dexamethasone.

By "gene editing" is meant altering the DNA sequence of a cell.

By "gene-editing protein" is meant a protein that can, either alone or in combination with another molecule, alter the DNA sequence of a cell, for example, a nuclease, a transcription activator-like effector nuclease (TALEN), a zinc-finger nuclease, a meganuclease, a nickase or a natural or engineered variant, family-member, orthologue, fragment or fusion construct thereof.

By "single-strand break" is meant a region of single-stranded or double-stranded DNA in which one or more of the covalent bonds linking the nucleotides has been broken in one of the one or two strands.

By "double-strand break" is meant a region of double-stranded DNA in which one or more of the covalent bonds linking the nucleotides has been broken in each of the two strands.

Serum albumin is a common component of serum-free cell-culture media. It has now been discovered that serum albumin can inhibit transfection, and that including untreated serum albumin in a transfection medium at concentrations normally used in serum-free cell-culture media can result in low transfection efficiency and/or low cell viability upon transfection. The serum albumin polypeptide can bind to a wide variety of molecules, including lipids, ions, cholesterol, etc., both in vitro and in vivo, and as a result, both serum albumin that is isolated from blood and recombinant serum albumin comprise a polypeptide component and an associated-molecule component. It has now been discovered that the low transfection efficiency and low cell viability upon transfection caused by serum albumin can be caused in part by the associated-molecule component of the serum albumin. It has been further discovered that transfection efficiency can be increased and transfection-associated toxicity can be reduced by partially or completely reducing, removing, replacing or otherwise inactivating the associated-molecule component of serum albumin. Certain embodiments of the invention are therefore directed to a method for treating a protein to partially or completely reduce, remove, replace or otherwise inactivate the associated-molecule component of the protein. Other embodiments are directed to a protein that is treated to partially or completely reduce, remove, replace or otherwise inactivate the associated-molecule component of the protein.

Certain embodiments are directed to a method for treating a protein by contacting the protein with one or more molecules that reduce the low transfection efficiency and/or low cell viability upon transfection caused by the protein. Contacting serum albumin with the short-chain fatty acid, sodium octanoate (also known as "octanoic acid", "octanoate", "caprylate" or "caprylic acid") was found to reduce the low transfection efficiency and low cell viability upon transfection caused by serum albumin in certain situations. Other substances that can be used to treat a protein include: capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, alpha-linolenic acid, arachidonic acid, eicosapentaenoic acid, erucic acid, docosahexaenoic acid, tryptophan, N-acetyl tryptophan, cholesterol, other fatty acids, and salts, mixtures, fragments, and derivatives thereof. Substances for treating a protein can be pure substances, well-defined mixtures or complex or undefined mixtures such as animal-based or plant-based oils, for example, cod-liver oil. In certain embodiments, a protein is treated after the protein is purified. In other embodiments, a protein is treated before the protein is purified. In still other embodiments, a protein is treated at the same time that the protein is purified. In still other embodiments, a protein is treated, and the protein is not purified.

Incubating a protein at an elevated temperature can cause partial or complete denaturation of the polypeptide component of the protein, which can reduce or eliminate binding sites that may be critical to maintaining the associated-molecule component of the protein. Certain embodiments are therefore directed to a method for treating a protein by incubating the protein at an elevated temperature. In one embodiment, the protein is incubated at a temperature of at least about 40° C. for at least about 10 minutes. In another embodiment, the protein is incubated at a temperature of at least about 50° C. for at least about 10 minutes. In another embodiment, the protein is incubated at a temperature of at least about 55° C. for at least about 30 minutes. In one embodiment, the protein is contacted with sodium octanoate, and then incubated at about 60° C. for several hours, such as between about 1 hour and about 24 hours, or between about 2 hours and about 6 hours. In another embodiment, the concentration of sodium octanoate is between about 5 mM and about 50 mM, or between about 10 mM and about 40 mM. In certain embodiments, the sodium octanoate is replaced with or used in combination with at least one element of capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, alpha-linolenic acid, arachidonic acid, eicosapentaenoic acid, erucic acid, docosahexaenoic acid, tryptophan, N-acetyl tryptophan, and cholesterol or a salt, mixture, fragment, and derivative thereof.

Glycation and glycosylation are processes by which one or more sugar molecules are bound to a protein. Glycation and glycosylation can impact the binding properties of a protein, and serum albumin contains several potential glycation sites. Certain embodiments are therefore directed to a method for treating a protein by glycating or glycosylating the protein.

Ion-exchange resins, including anion-exchange, cation-exchange, and mixed-bed resins, are routinely used to deionize solutions. The associated-molecule component of proteins such as serum albumin can comprise ions. Certain embodiments are therefore directed to a method for treating a protein by contacting the protein with one or more ion-exchange resins. In one embodiment, the one or more ion-exchange resins includes a mixed-bed resin containing functional groups with proton (H+) and hydroxyl (OH—) forms. In another embodiment, the one or more ion-exchange resins includes an indicator that changes color as the resin becomes saturated with ions. In addition to contacting with one or more ion-exchange resins, other methods can be used to reduce, remove, replace or otherwise inactivate the associated-molecule component of a protein, including contacting the protein with charcoal, which may be activated and/or treated with a chemical such as dextran sulfate, dialysis (including dilution resulting in de-association of the associated-molecule component, whether or not the de-associated molecules are subsequently removed from the solution), crystallization, chromatography, electrophoresis, heat treatment, low-temperature treatment, high-pH treatment, low-pH treatment, organic-solvent precipitation, and affinity purification.

Certain methods for treating a protein may preferentially reduce, remove, replace or otherwise inactivate specific types of molecules. In certain situations, it can therefore be beneficial to combine two or more methods for treating a protein to reduce the low transfection efficiency and/or low cell viability upon transfection caused by the protein. Certain embodiments are therefore directed to a method for treating a protein using two or more methods to reduce, remove, replace or otherwise inactivate the associated-molecule component of the protein. In one embodiment, a protein is contacted with one or more ion-exchange resins and activated charcoal. In another embodiment, a protein is contacted with sodium octanoate, incubated at an elevated temperature, contacted with one or more ion-exchange resins, and contacted with activated charcoal. In another embodiment, the protein is serum albumin, and the elevated temperature is at least about 50° C.

Certain elements of the associated-molecule component of a protein can be beneficial to cells in culture, and/or to transfection, for example, certain resolvins, protectins, lipoxins, maresins, eicosanoids, prostacyclins, thromboxanes, leukotrienes, cyclopentenone prostaglandins, and glucocorticoids. Certain embodiments are therefore directed to a method for treating a protein to reduce, remove, replace or otherwise inactivate the associated-molecule component of the protein without reducing, removing, replacing or otherwise inactivating one or more beneficial elements of the associated-molecule component of the protein. Other embodiments are directed to a method for treating a protein to reduce, remove, replace or otherwise inactivate the associated-molecule component of the protein, and further contacting the protein with one or more molecules comprising one or more beneficial elements of the associated-molecule component of the protein.

Still other embodiments are directed to a method for treating a protein to reduce the low transfection efficiency and/or low cell viability upon transfection caused by the protein by contacting the protein with one or more molecules comprising one or more beneficial elements of the associated-molecule component of the protein. Still other embodiments are directed to a method for increasing transfection efficiency and/or increasing cell viability upon transfection by contacting a cell with one or more molecules comprising one or more beneficial elements of the associated-molecule component of a protein. In one embodiment, the protein is contacted with one or more ion-exchange resins or charcoal, and is further contacted with a glucocorticoid, such as hydrocortisone, prednisone, prednisolone, methylprednisolone, dexamethasone or betamethasone. In another embodiment, the cell is contacted with a glucocorticoid, such as hydrocortisone, prednisone, prednisolone, methylprednisolone, dexamethasone or betamethasone. It has been further discovered that in certain situations, including one or more steroids and/or one or more antioxidants in the transfection medium can increase transfection efficiency, reprogramming efficiency, and gene-editing efficiency. Certain embodiments are therefore directed to a method for inducing a cell to express a protein of interest by culturing the cell in a medium containing a steroid and contacting the cell with one or more synthetic RNA molecules. In one embodiment, the steroid is hydrocortisone. In another embodiment, the hydrocortisone is present in the medium at a concentration of between about 0.1 uM and about 10 uM, or about 1 uM. Other embodiments are directed to a method for inducing a cell to express a protein of interest by culturing the cell in a medium containing an antioxidant and contacting the cell with one or more synthetic RNA molecules. In one embodiment, the antioxidant is ascorbic acid or ascorbic-acid-2-phosphate. In another embodiment, the ascorbic acid or ascorbic-acid-2-phosphate is present in the medium at a concentration of between about 0.5 mg/L and about 500 mg/L, including about 50 mg/L. Still other embodiments are directed to a method for reprogramming and/or gene-editing a cell by culturing the cell in a medium containing a steroid and/or an antioxidant and contacting the cell with one or more synthetic RNA molecules, wherein the one or more synthetic RNA molecules encodes one or more reprogramming and/or gene-editing proteins. In certain embodiments, the cell is present in an organism, and the steroid and/or antioxidant are delivered to the organism.

Adding transferrin to the complexation medium has been reported to increase the efficiency of plasmid transfection in certain situations. It has now been discovered that adding transferrin to the complexation medium can also increase the efficiency of transfection with synthetic RNA molecules. Certain embodiments are therefore directed to a method for inducing a cell to express a protein of interest by adding one or more synthetic RNA molecules and a transfection reagent to a solution containing transferrin. In one embodiment, the transferrin is present in the solution at a concentration of between about 1 mg/L and about 100 mg/L, such as about 5 mg/L. In another embodiment, the transferrin is recombinant.

Other embodiments are directed to a medium containing a protein that is treated according to one or more of the methods of the present invention. In certain embodiments, the protein is treated before being mixed with one or more of the other ingredients of the medium. In one embodiment, the medium is a transfection medium. In another embodiment, the medium also supports efficient transfection and high cell viability. In certain embodiments, the protein and one or more molecules that reduce the low transfection efficiency and/or low cell viability upon transfection caused by the protein are added independently to the medium. In one embodiment, the protein is treated before being mixed with one or more of the other ingredients of the medium. In another embodiment, the medium is prepared by first treating a concentrated solution of serum albumin by contacting the concentrated solution of serum albumin with one or more ion-exchange resins, then removing the one or more ion-exchange resins from the concentrated solution of serum albumin, and then adding the treated concentrated solution of serum albumin to the other components of the medium. In another embodiment, the concentrated solution of serum albumin is further contacted with charcoal before adding the concentrated solution of serum albumin to the other components of the medium. In still another embodiment, the concentrated solution of serum albumin is first contacted with sodium octanoate, then raised to a temperature of at least about 50° C. for at least about 10 minutes, then contacted with one or more ion-exchange resins, then contacted with activated charcoal, and then added to the other components of the medium.

It has now been discovered that transfecting cells using a medium containing a buffered salt solution, amino acids, cholesterol, hydrocortisone, and serum albumin can result in efficient transfection, and that transfecting cells using a medium consisting essentially of a buffered salt solution, amino acids, insulin, transferrin, cholesterol, hydrocortisone, serum albumin, and a fibroblast growth factor can result in efficient transfection and efficient reprogramming. Certain embodiments are therefore directed to a transfection medium containing: a buffered salt solution, amino acids, cholesterol, hydrocortisone, and serum albumin. Other embodiments are directed to a transfection medium consisting essentially of and/or comprising: a buffered salt solution, amino acids, insulin, transferrin, cholesterol, hydrocortisone, serum albumin, and a fibroblast growth factor. Still other embodiments are directed to a reprogramming medium consisting essentially of and/or comprising: a buffered salt solution, amino acids, insulin, transferrin, cholesterol, hydrocortisone, serum albumin, and a fibroblast growth factor. In one embodiment, the medium also includes polyoxyethylenesorbitan monooleate and/or D-alpha-tocopherol acetate. In another embodiment, the medium also includes ascorbic acid or ascorbic-acid-2-phosphate, for example, at a concentration of between about 1 mg/L and about 100 mg/L. In one embodiment, the hydrocortisone is present at a concentration of about 1 uM. In another embodiment, the fibroblast growth factor is basic fibroblast growth factor, and the basic fibroblast growth factor is present at a concentration of between about 1 ng/mL and about 200 ng/mL, such as between about 4 ng/mL and about 100 ng/mL, or between about 10 ng/mL and about 50 ng/mL, or about 20 ng/mL. In one embodiment, the serum albumin is human serum albumin, and the human serum albumin is present at a concentration of between about 0.05% and about 2%, including between about 0.1% and about 1%, such as about 0.5%. In another embodiment, the human serum albumin is recombinant. In yet another embodiment, the cholesterol is present at a concentration of about 4.5 mg/L. In one embodiment, the medium does not contain any animal-derived components. In another embodiment, the medium does not contain any undefined components, for example, cod liver-oil fatty acids or serum. In one embodiment, the medium contains a TGF-β inhibitor, for example, A83-01 or SB431542. In one embodiment, the TGF-β inhibitor is present at a concentration of between about 0.1 uM and about 10 uM. In one embodiment, the medium contains a Wnt signaling agonist, such as Wnt3a. In another embodiment, the Wnt signaling agonist is present at a concentration of between about 10 ng/mL and about 500 ng/mL, including between about 50 ng/mL and about 200 ng/mL. In one embodiment, the medium contains a source of selenium, such as sodium selenite.

In certain situations, it may be desirable to replace animal-derived components with non-animal-derived and/or recombinant components, in part because non-animal-derived and/or recombinant components can be produced with a higher degree of consistency than animal-derived components, and in part because non-animal-derived and/or recombinant components carry less risk of contamination with toxic and/or pathogenic substances than do animal-derived components. Certain embodiments are therefore directed to a protein that is non-animal-derived and/or recombinant. Other embodiments are directed to a medium, wherein some or all of the components of the medium are non-animal-derived and/or recombinant. In one embodiment, the protein is recombinant serum albumin. In another embodiment, the protein is recombinant human serum albumin. In yet another embodiment, the protein is recombinant serum albumin and all of the components of the medium are non-animal-derived and/or recombinant.

The N-terminus of serum albumin can contain a nickel- and copper-binding domain, which may be an important antigenic determinant. Deleting the aspartic acid residue from the N-terminus of serum albumin can eliminate the nickel- and copper-binding activity of serum albumin, and can result in a hypoallergenic variant of the protein. Certain embodiments are therefore directed to a protein that has modified binding characteristics and/or other desirable characteristics such as hypoallergenicity. In one embodiment, the protein is serum albumin, and the serum albumin lacks an N-terminal aspartic acid.

Other embodiments are directed to a method for transfecting a cell. In one embodiment, a cell is transfected with one or more nucleic acids, and the transfection is performed using a transfection reagent, such as a lipid-based transfection reagent. In one embodiment, the one or more nucleic acids includes at least one RNA molecule. In another embodiment, the cell is transfected with one or more nucleic acids, and the one or more nucleic acids encodes at least one of: p53, TERT, a cytokine, a secreted protein, a membrane-bound protein, an enzyme, a gene-editing protein, a chromatin-modifying protein, a DNA-binding protein, a transcription factor, a histone deacetylase, a pathogen-associated molecular pattern, and a tumor-associated antigen or a biologically active fragment, analogue, variant or family-member thereof. In another embodiment, the cell is transfected repeatedly, such as at least about 2 times during about 10 consecutive days, or at least about 3 times during about 7 consecutive days, or at least about 4 times during about 6 consecutive days.

Reprogramming can be performed by transfecting cells with one or more nucleic acids encoding one or more reprogramming factors, and culturing the cells in a medium that supports the reprogrammed cells. Examples of reprogramming factors include, but are not limited to: Oct4 protein, Sox2 protein, Klf4 protein, c-Myc protein, 1-Myc protein, TERT protein, Nanog protein, Lin28 protein, Utf1 protein, Aicda protein, miR200 micro-RNA, miR302 micro-RNA, miR367 micro-RNA, miR369 micro-RNA and biologically active fragments, analogues, variants and family-members thereof. Certain embodiments are therefore directed to a method for reprogramming a cell. In one embodiment, the cell is reprogrammed by transfecting the cell with one or more nucleic acids encoding one or more reprogramming factors. In one embodiment, the one or more nucleic acids includes an RNA molecule that encodes Oct4 protein. In another embodiment, the one or more nucleic acids also includes one or more RNA molecules that encodes Sox2 protein, Klf4 protein, and c-Myc protein. In yet another embodiment, the one or more nucleic acids also includes an RNA molecule that encodes Lin28 protein. In one embodiment, the cell is a human skin cell, and the human skin cell is reprogrammed to a pluripotent stem cell. In another embodiment, the cell is a human skin cell, and the human skin cell is reprogrammed to a glucose-responsive insulin-producing cell. Examples of other cells that can be reprogrammed and other cells to which a cell can be reprogrammed include, but are not limited to: skin cells, pluripotent stem cells, mesenchymal stem cells, β-cells, retinal pigmented epithelial cells, hematopoietic cells, cardiac cells, airway epithelial cells, neural stem cells, neurons, glial cells, bone cells, blood cells, and dental pulp stem cells. In one embodiment, the cell is cultured in a medium that supports the reprogrammed cell. In one embodiment, the medium also supports the cell.

Importantly, infecting skin cells with viruses encoding Oct4, Sox2, Klf4, and c-Myc, combined with culturing the cells in a medium that supports the growth of cardiomyocytes, has been reported to cause reprogramming of the skin cells to cardiomyocytes, without first reprogramming the skin cells to pluripotent stem cells (See Efs et al Nat Cell Biol. 2011; 13:215-22, the contents of which are hereby incorporated by reference). In certain situations, for example when generating a personalized therapeutic, direct reprogramming (reprogramming one somatic cell to another somatic cell without first reprogramming the somatic cell to a pluripotent stem cell, also known as "transdifferentiation") may be desirable, in part because culturing pluripotent stem cells can be time-consuming and expensive, the additional handling involved in establishing and characterizing a stable pluripotent stem cell line can carry an increased risk of contamination, and the additional time in culture associated with first producing pluripotent stem cells can carry an increased risk of genomic instability and the acquisition of mutations, including point mutations, copy-number variations, and karyotypic abnormalities. Certain embodiments are therefore directed to a method for reprogramming a somatic cell, wherein the cell is reprogrammed to a somatic cell, and wherein a characterized pluripotent stem-cell line is not produced.

Previously reported methods for reprogramming cells by transfecting them with RNA encoding reprogramming factors require the use of feeders. In many situations, the use of feeders may not be desirable, in part because feeders may be derived from animal or allogeneic sources, and may thus carry risks of immunogenicity and contamination with pathogens. It has now been discovered that the medium of the present invention can enable RNA reprogramming without feeders. It has been further discovered that reprogramming cells according to the methods of the present invention, wherein the cells are not contacted with feeders, can be rapid, efficient, and reliable. Certain embodiments are therefore directed to a method for reprogramming a cell, wherein the cell is not contacted with feeders.

It has now been discovered that reprogramming efficiency can correlate with starting cell density when cells are reprogrammed according to the methods of the present invention. Certain embodiments are therefore directed to a method for reprogramming cells, wherein the cells are plated at a density of between about 100 cells/cm$^2$ and about 100,000 cells/cm$^2$. In one embodiment, the cells are plated at a density of between about 100 cells/cm$^2$ and about 10,000 cells/cm$^2$ or between about 2000 cells/cm$^2$ and about 20,000 cells/cm$^2$, or between about 1000 cells/cm$^2$ and about 2000 cells/cm$^2$.

It has been further discovered that, in certain situations, fewer total transfections may be required to reprogram a cell according to the methods of the present invention than according to other methods. Certain embodiments are therefore directed to a method for reprogramming a cell, wherein between about 2 and about 12 transfections are performed during about 20 consecutive days, or between about 4 and about 10 transfections are performed during about 15 consecutive days, or between about 4 and about 8 transfections are performed during about 10 consecutive days. It is recognized that when nucleic acids are added to a medium in which a cell is cultured, the cell may likely come into contact with and/or internalize more than one nucleic acid molecule either simultaneously or at different times. A cell can therefore be contacted with a nucleic acid more than once, e.g. repeatedly, even when nucleic acids are added only once to a medium in which the cell is cultured.

Feeders can promote adhesion of cells to a surface by secreting molecules such as collagen that bind to the surface ("cell-adhesion molecules"). Proteins, including integrins, on the surface of cells can bind to these cell-adhesion molecules, which can result in the cells adhering to the surface. It has now been discovered that cells can be reprogrammed, including without feeders, by coating a surface with one or more cell-adhesion molecules. It has been further discovered that the cell-adhesion molecules fibronectin and vitronectin are particularly well suited for this purpose. Certain embodiments are therefore directed to a method for transfecting, reprogramming, and/or gene-editing a cell, wherein the cell is contacted with a surface that is contacted with one or more cell-adhesion molecules. In one embodiment, the one or more cell-adhesion molecules includes at least one of: poly-L-lysine, poly-L-ornithine, RGD peptide, fibronectin, vitronectin, collagen, and laminin or a biologically active fragment, analogue, variant or family-member thereof. In another embodiment, the one or more cell-adhesion molecules is fibronectin or a biologically active fragment thereof. In yet another embodiment, the fibronectin is recombinant. In still another embodiment, the one or more cell-adhesion molecules is a mixture of fibronectin and vitronectin or biologically active fragments thereof. In another embodiment, the fibronectin and vitronectin are each present at a concentration of about 100 ng/cm$^2$ on the surface and/or at a concentration of about 1 ug/mL in a solution used to coat the surface. In a still another embodiment, both the fibronectin and vitronectin are recombinant. Contacting of the surface with the one or more cell-adhesion molecules can be performed as an independent step, and/or by including the one or more cell-adhesion molecules in the medium.

Of note, nucleic acids can contain one or more non-canonical, or "modified", residues (e.g. a residue other than adenine, guanine, thymine, uracil, and cytosine or the standard nucleoside, nucleotide, deoxynucleoside or deoxynucleotide derivatives thereof). Of particular note, pseudouridine-5'-triphosphate can be substituted for uridine-5'-triphosphate in an in vitro-transcription reaction to yield synthetic RNA, wherein up to 100% of the uridine residues of the synthetic RNA may be replaced with pseudouridine residues. In vitro-transcription can yield RNA with residual immunogenicity, even when pseudouridine and 5-methylcytidine are completely substituted for uridine and cytidine, respectively (See Angel Reprogramming Human Somatic Cells to Pluripotency Using RNA [Doctoral Thesis]. Cambridge, Mass.: MIT; 2011, the contents of which are hereby incorporated by reference). For this reason, it is common to add an immunosuppressant to the transfection medium when transfecting cells with RNA. In certain situations, adding an immunosuppressant to the transfection medium may not be desirable, in part because the recombinant immunosuppressant most commonly used for this purpose, B18R, can be expensive and difficult to manufacture. It has now been discovered that cells can be transfected and/or reprogrammed according to the methods of the present invention, without using B18R or any other immunosuppressant. It has been further discovered that reprogramming cells according to the methods of the present invention without using immunosuppressants can be rapid, efficient, and reliable. Certain embodiments are therefore directed to a method for transfecting a cell, wherein the transfection medium does not contain an immunosuppressant. Other embodiments are directed to a method for reprogramming a cell, wherein the transfection medium does not contain an immunosuppressant. In certain situations, for example when using a high cell density, it may be beneficial to add an immunosuppressant to the transfection medium. Certain embodiments are therefore directed to a method for transfecting a cell, wherein the transfection medium contains an immunosuppressant. Other embodiments are directed to a method for reprogramming a cell, wherein the transfection medium contains an immunosuppressant. In one embodiment, the immunosuppressant is B18R or a biologically active fragment, analogue, variant or family-member thereof or dexamethasone or a derivative thereof. In one embodiment, cells are plated at a density of less than about 20,000 cells/cm$^2$, and the transfection medium does not contain an immunosuppressant. In another embodiment, the transfection medium does not contain an immunosuppressant, and the nucleic-acid dose is chosen to prevent excessive toxicity. In still another embodiment, the nucleic-acid dose is less than 2 μg/well of a 6-well plate, such as about 0.25 μg/well of a 6-well plate or about 1 ug/well of a 6-well plate.

Reprogrammed cells produced according to certain embodiments of the present invention are suitable for therapeutic applications, including transplantation into patients, as they do not contain exogenous DNA sequences, and they are not exposed to animal-derived or human-derived products, which may be undefined, and which may contain toxic and/or pathogenic contaminants. Furthermore, the high speed, efficiency, and reliability of certain embodiments of the present invention may reduce the risk of acquisition and accumulation of mutations and other chromosomal abnormalities. Certain embodiments of the present invention can thus be used to generate cells that have a safety profile adequate for use in therapeutic applications. For example, reprogramming cells using RNA and the medium of the present invention, wherein the medium does not contain animal or human-derived components, can yield cells that have not been exposed to allogeneic material. Certain embodiments are therefore directed to a reprogrammed cell that has a desirable safety profile. In one embodiment, the reprogrammed cell has a normal karyotype. In another embodiment, the reprogrammed cell has fewer than about 5 copy-number variations (CNVs) relative to the patient genome, such as fewer than about 3 copy-number variations relative to the patient genome, or no copy-number variations relative to the patient genome. In yet another embodiment, the reprogrammed cell has a normal karyotype and fewer than about 100 single nucleotide variants in coding regions relative to the patient genome, or fewer than about 50 single nucleotide variants in coding regions relative to the patient genome, or fewer than about 10 single nucleotide variants in coding regions relative to the patient genome.

Endotoxins and nucleases can co-purify and/or become associated with other proteins, such as serum albumin. Recombinant proteins, in particular, can often have high levels of associated endotoxins and nucleases, due in part to the lysis of cells that can take place during their production. Endotoxins and nucleases can be reduced, removed, replaced or otherwise inactivated by many of the methods of the present invention, including, for example, by acetylation, by addition of a stabilizer such as sodium octanoate, followed by heat treatment, by the addition of nuclease inhibitors to the albumin solution and/or medium, by crystallization, by contacting with one or more ion-exchange resins, by contacting with charcoal, by preparative electrophoresis or by affinity chromatography. It has now been discovered that partially or completely reducing, removing, replacing or otherwise inactivating endotoxins and/or nucleases from a medium and/or from one or more components of a medium can increase the efficiency with which cells can be transfected and reprogrammed. Certain embodiments are therefore directed to a method for transfecting a cell with one or more nucleic acids, wherein the transfection medium is treated to partially or completely reduce, remove, replace or otherwise inactivate one or more endotoxins and/or nucleases. Other embodiments are directed to a medium that causes minimal degradation of nucleic acids. In one embodiment, the medium contains less than about 1 EU/mL, or less than about 0.1 EU/mL, or less than about 0.01 EU/mL.

In certain situations, protein-based lipid carriers such as serum albumin can be replaced with non-protein-based lipid carriers such as methyl-beta-cyclodextrin. The medium of the present invention can also be used without a lipid carrier, for example, when transfection is performed using a method that may not require or may not benefit from the presence of a lipid carrier, for example, using one or more polymer-based transfection reagents or peptide-based transfection reagents.

Many protein-associated molecules, such as metals, can be highly toxic to cells. This toxicity can cause decreased viability in culture, as well as the acquisition of mutations. Certain embodiments thus have the additional benefit of producing cells that are free from toxic molecules.

The associated-molecule component of a protein can be measured by suspending the protein in solution and measuring the conductivity of the solution. Certain embodiments are therefore directed to a medium that contains a protein, wherein about a 10% solution of the protein in water has a conductivity of less than about 500 mho/cm. In one embodiment, the solution has a conductivity of less than about 50 mho/cm.

A low-oxygen environment can be beneficial for the culture of many types of cells. Certain embodiments are therefore directed to a method for culturing, transfecting, reprogramming, and/or gene-editing cells, wherein the cells are cultured, transfected, reprogrammed, and/or gene-edited in a low-oxygen environment. In one embodiment, the low-oxygen environment contains between about 2% and about 10% oxygen, or between about 4% and about 6% oxygen.

The amount of nucleic acid delivered to cells can be increased to increase the desired effect of the nucleic acid. However, increasing the amount of nucleic acid delivered to cells beyond a certain point can cause a decrease in the viability of the cells, due in part to toxicity of the transfection reagent. It has now been discovered that when a nucleic acid is delivered to a population of cells in a fixed volume (for example, cells in a region of tissue or cells grown in a cell-culture vessel), the amount of nucleic acid delivered to each cell can depend on the total amount of nucleic acid delivered to the population of cells and to the density of the cells, with a higher cell density resulting in less nucleic acid being delivered to each cell. In certain embodiments, a cell is transfected with one or more nucleic acids more than once. Under certain conditions, for example when the cells are proliferating, the cell density may change from one transfection to the next. Certain embodiments are therefore directed to a method for transfecting a cell with a nucleic acid, wherein the cell is transfected more than once, and wherein the amount of nucleic acid delivered to the cell is different for two of the transfections. In one embodiment, the cell proliferates between two of the transfections, and the amount of nucleic acid delivered to the cell is greater for the second of the two transfections than for the first of the two transfections. In another embodiment, the cell is transfected more than twice, and the amount of nucleic acid delivered to the cell is greater for the second of three transfections than for the first of the same three transfections, and the amount of nucleic acid delivered to the cells is greater for the third of the same three transfections than for the second of the same three transfections. In yet another embodiment, the cell is transfected more than once, and the maximum amount of nucleic acid delivered to the cell during each transfection is sufficiently low to yield at least about 80% viability for at least two consecutive transfections.

It has now been discovered that modulating the amount of nucleic acid delivered to a population of proliferating cells in a series of transfections can result in both an increased effect of the nucleic acid and increased viability of the cells. It has been further discovered that, in certain situations, when cells are contacted with one or more nucleic acids encoding one or more reprogramming factors in a series of transfections, the efficiency of reprogramming can be increased when the amount of nucleic acid delivered in later transfections is greater than the amount of nucleic acid delivered in earlier transfections, for at least part of the series of transfections. Certain embodiments are therefore directed to a method for reprogramming a cell, wherein one or more nucleic acids is repeatedly delivered to the cell in a series of transfections, and the amount of the nucleic acid delivered to the cell is greater for at least one later transfection than for at least one earlier transfection. In one embodiment, the cell is transfected between about 2 and about 10 times, or between about 3 and about 8 times, or between about 4 and about 6 times. In another embodiment, the one or more nucleic acids includes at least one RNA molecule, the cell is transfected between about 2 and about 10 times, and the amount of nucleic acid delivered to the cell in each transfection is the same as or greater than the amount of nucleic acid delivered to the cell in the most recent previous transfection. In yet another embodiment, the amount of nucleic acid delivered to the cell in the first transfection is between about 20 ng/cm$^2$ and about 250 ng/cm$^2$, or between 100 ng/cm$^2$ and 600 ng/cm$^2$. In yet another embodiment, the cell is transfected about 5 times at intervals of between about 12 and about 48 hours, and the amount of nucleic acid delivered to the cell is about 25 ng/cm$^2$ for the first transfection, about 50 ng/cm$^2$ for the second transfection, about 100 ng/cm$^2$ for the third transfection, about 200 ng/cm$^2$ for the fourth transfection, and about 400 ng/cm$^2$ for the fifth transfection. In yet another embodiment, the cell is further transfected at least once after the fifth transfection, and the amount of nucleic acid delivered to the cell is about 400 ng/cm$^2$.

Certain embodiments are directed to a method for transfecting a cell with a nucleic acid, wherein the amount of nucleic acid is determined by measuring the cell density, and choosing the amount of nucleic acid to transfect based on the measurement of cell density. In one embodiment, the cell is present in an in vitro culture, and the cell density is measured by optical means. In another embodiment, the cell is transfected repeatedly, the cell density increases between two transfections, and the amount of nucleic acid transfected is greater for the second of the two transfections than for the first of the two transfections.

It has now been discovered that, in certain situations, the transfection efficiency and viability of cells cultured in the medium of the present invention can be improved by conditioning the medium. Certain embodiments are therefore directed to a method for conditioning a medium. Other embodiments are directed to a medium that is conditioned. In one embodiment, the feeders are fibroblasts, and the medium is conditioned for approximately 24 hours. Other embodiments are directed to a method for transfecting a cell, wherein the transfection medium is conditioned. Other embodiments are directed to a method for reprogramming and/or gene-editing a cell, wherein the medium is conditioned. In one embodiment, the feeders are mitotically inactivated, for example, by exposure to a chemical such as mitomycin-C or by exposure to gamma radiation. In certain embodiments, it may be beneficial to use only autologous materials, in part to, for example and not wishing to be bound by theory, avoid the risk of disease transmission from the feeders to the cell. Certain embodiments are therefore directed to a method for transfecting a cell, wherein the transfection medium is conditioned, and wherein the feeders are derived from the same individual as the cell being transfected. Other embodiments are directed to a method for reprogramming and/or gene-editing a cell, wherein the medium is conditioned, and wherein the feeders are derived from the same individual as the cell being reprogrammed and/or gene-edited.

Several molecules can be added to media by conditioning. Certain embodiments are therefore directed to a medium that is supplemented with one or more molecules that are present in a conditioned medium. In one embodiment, the medium is supplemented with Wnt1, Wnt2, Wnt3, Wnt3a or a biologically active fragment, analogue, variant, agonist, or family-member thereof. In another embodiment, the medium is supplemented with TGF-β or a biologically active fragment, analogue, variant, agonist, or family-member thereof. In yet another embodiment, a cell is reprogrammed according to the method of the present invention, wherein the medium is not supplemented with TGF-β for between about 1 and about 5 days, and is then supplemented with TGF-β for at least about 2 days. In yet another embodiment, the medium is supplemented with IL-6, IL-6R or a biologically active fragment, analogue, variant, agonist, or family-member thereof. In yet another embodiment, the medium is supplemented with a sphingolipid or a fatty acid. In still another embodiment, the sphingolipid is lysophosphatidic acid, lysosphingomyelin, sphingosine-1-phosphate or a biologically active analogue, variant or derivative thereof.

In addition to mitotically inactivating cells, under certain conditions, irradiation can change the gene expression of cells, causing cells to produce less of certain proteins and more of certain other proteins that non-irradiated cells, for example, members of the Wnt family of proteins. In addition, certain members of the Wnt family of proteins can promote the growth and transformation of cells. It has now been discovered that, in certain situations, the efficiency of RNA reprogramming can be greatly increased by contacting the cell with a medium that is conditioned using irradiated feeders instead of mitomycin-c-treated feeders. It has been further discovered that the increase in reprogramming efficiency observed when using irradiated feeders is caused in part by Wnt proteins that are secreted by the feeders. Certain embodiments are therefore directed to a method for reprogramming a cell, wherein the cell is contacted with Wnt1, Wnt2, Wnt3, Wnt3a or a biologically active fragment, analogue, variant, family-member or agonist thereof, including agonists of downstream targets of Wnt proteins, and/or agents that mimic one or more of the biological effects of Wnt proteins, for example, 2-amino-4-[3,4-(methylenedioxy)benzylamino]-6-(3-methoxyphenyl)pyrimidine.

It has now been discovered that the medium of the present invention can be used to maintain cells, including fibroblasts and human pluripotent stem cells, in culture (i.e. as a "maintenance medium").

Certain embodiments are therefore directed to a medium that is used as a maintenance medium. In one embodiment, the medium does not contain any human-derived components. In another embodiment, the medium is chemically defined.

Because of the low efficiency of many DNA-based reprogramming methods, these methods may be difficult or impossible to use with cells derived from patient samples, which may contain only a small number of cells. In contrast, the high efficiency of certain embodiments of the present invention can allow reliable reprogramming from small numbers of cells, including from single cells. Certain embodiments can thus be used to reprogram cells from a biopsy sample, including without first establishing a large culture. Reprogramming cells directly from a biopsy may be desirable in certain situations, for example when generating a personalized therapeutic, in part because establishing a large culture of primary cells can be time-consuming, the additional handling involved in establishing a large culture can carry an increased risk of contamination, and the additional time in culture can carry an increased risk of genomic instability and the acquisition of mutations, including point mutations, copy-number variations, and karyotypic abnormalities. Certain embodiments are therefore directed to a method for reprogramming a cell by first harvesting the cell from a patient or from a biopsy sample, and then reprogramming the cell. In one embodiment, the cell is reprogrammed without first establishing a large culture, preferably a first transfection is performed before the culture is passaged more than twice. In another embodiment, the cell is harvested from a patient, and a first transfection is performed after no more than about 14 days from the time the cell is first plated. In yet another embodiment, the cell is harvested from a biopsy sample, and a first transfection is performed after no more than about 7 days from the time the cell is first plated. In yet another embodiment, the biopsy is a full-thickness dermal punch biopsy, the cell is harvested from the biopsy sample by treatment with one or more enzymes, the cell is plated on a surface that is coated with one or more cell-adhesion molecules and/or the cell is plated in a medium that contains a cell-adhesion molecule, the cell is transfected with one or more nucleic acids comprising at least one RNA molecule, and a first transfection is performed after no more than about 14 days from the time the cell is first plated. In still another embodiment, the enzyme is collagenase. In yet another embodiment, the collagenase is animal-component free. In another embodiment, the collagenase is present at a concentration of between about 0.1 mg/mL and about 10 mg/mL, or between about 0.5 mg/mL and about 5 mg/mL. In yet another embodiment, the cell is harvested from blood. In yet another embodiment, the cell is plated in a medium containing one or more proteins that is derived from the patient's blood. In still another embodiment, the cell is plated in DMEM/F12+2 mM L-alanyl-L-glutamine+between about 5% and about 25% patient-derived serum, or between about 10% and about 20% patient-derived serum, or about 20% patient-derived serum.

It has now been discovered that, in certain situations, transfecting cells with a mixture of RNA encoding Oct4, Sox2, Klf4, and c-Myc using the medium of the present invention can cause the rate of proliferation of the cells to increase. When the amount of RNA delivered to the cells is too low to ensure that all of the cells are transfected, only a fraction of the cells may show an increased proliferation rate. In certain situations, such as when generating a personalized therapeutic, increasing the proliferation rate of cells may be desirable, in part because doing so can reduce the time necessary to generate the therapeutic, and therefore can reduce the cost of the therapeutic. Certain embodiments are therefore directed to a method for transfecting a cell with a mixture of RNA encoding Oct4, Sox2, Klf4, and c-Myc, wherein the cell exhibits an increased proliferation rate. In one embodiment, cells showing an increased proliferation rate are isolated from the culture. In another embodiment, cells showing an increased proliferation rate are expanded and cultured in a medium that supports the growth of one or more cell types, and are reprogrammed to a cell of one of the one or more cell types.

Many diseases are associated with one or more mutations. Mutations can be corrected by contacting a cell with a nucleic acid that encodes a protein that, either alone or in combination with other molecules, corrects the mutation (an example of gene-editing). Examples of such proteins include: zinc finger nucleases and TALENs. Certain embodiments are therefore directed to a method for transfecting a cell with a nucleic acid, wherein the nucleic acid encodes a protein that, either alone or in combination with other molecules, creates a single-strand or double-strand break in a DNA molecule. In a one embodiment, the protein is a zinc finger nuclease or a TALEN. In another embodiment, the nucleic acid is an RNA molecule. In yet another embodiment, the single-strand or double-strand break is within about 5,000,000 bases of the transcription start site of a gene selected from the group: CCR5, CXCR4, GAD1, GAD2, CFTR, HBA1, HBA2, HBB, HBD, FANCA, XPA, XPB, XPC, ERCC2, POLH, HTT, DMD, SOD1, APOE, PRNP, BRCA1, and BRCA2 or an analogue, variant or family-member thereof. In yet another embodiment, the cell is transfected with a nucleic acid that acts as a repair template by either causing the insertion of a DNA sequence in the region of the single-strand or double-strand break or by causing the DNA sequence in the region of the single-strand or double-strand break to otherwise change. In yet another embodiment, the cell is reprogrammed, and subsequently, the cell is gene-edited. In yet another embodiment, the cell is gene-edited, and subsequently, the cell is reprogrammed. In yet another embodiment, the gene-editing and reprogramming are performed within about 7 days of each other. In yet another embodiment, the gene-editing and reprogramming occur simultaneously or on the same day. In yet another embodiment, the cell is a skin cell, the skin cell is gene-edited to disrupt the CCR5 gene, the skin cell is reprogrammed to a hematopoietic stem cell, thus producing a therapeutic for HIV/AIDS, and the therapeutic is introduced into a patient with HIV/AIDS. In yet another embodiment, the skin cell is derived from the same patient into whom the therapeutic is introduced.

Genes that can be edited according to the methods of the present invention to produce therapeutics of the present invention include genes that can be edited to restore normal function, as well as genes that can be edited to reduce or eliminate function. Such genes include, but are not limited to beta globin (HBB), mutations in which can cause sickle cell disease (SCD) and β-thalassemia, breast cancer 1, early onset (BRCA1) and breast cancer 2, early onset (BRCA2), mutations in which can increase susceptibility to breast cancer, C—C chemokine receptor type 5 (CCR5) and C—X—C chemokine receptor type 4 (CXCR4), mutations in which can confer resistance to HIV infection, cystic fibrosis transmembrane conductance regulator (CFTR), mutations in which can cause cystic fibrosis, dystrophin (DMD), mutations in which can cause muscular dystrophy, including Duchenne muscular dystrophy and Becker's muscular dystrophy, glutamate decarboxylase 1 and glutamate decarboxylase 2 (GAD1, GAD2), mutations in which can prevent autoimmune destruction of β-cells, hemoglobin alpha 1, hemoglobin alpha 2, and hemoglobin delta (HBA1, HBA2, and HBD), mutations in which can cause thalassemia, Huntington (HTT), mutations in which can cause Huntington's disease, superoxide dismutase 1 (SOD1), mutations in which can cause amyotrophic lateral sclerosis (ALS), XPA, XPB, XPC, XPD (ERCC6) and polymerase (DNA directed), eta (POLH), mutations in which can cause xeroderma pigmentosum, leucine-rich repeat kinase 2 (LRRK2), mutations in which can cause Parkinson's disease, and Fanconi anemia, complementation groups A, B, C, D1, D2, E, F, G, I, J, L, M, N, P (FANCA, FANCB, FANCC, FANCD1, FANCD2, FANCE, FANCF, FANCG, FANCI, FANCJ, FANCL, FANCM, FANCN, FANCP), and RAD51 homolog C (*S. cerevisiae*) (RAD51C), mutations in which can cause Fanconi anemia.

Certain embodiments are directed to a therapeutic comprising a nucleic acid that encodes one or more gene-editing proteins. Other embodiments are directed to a therapeutic comprising one or more cells that are transfected, reprogrammed, and/or gene-edited according to the methods of the present invention. In one embodiment, a cell is transfected, reprogrammed, and/or gene-edited, and the transfected, reprogrammed, and/or gene-edited cell is introduced into a patient. In another embodiment, the cell is harvested from the same patient into whom the transfected, reprogrammed and/or gene-edited cell is introduced. Examples of diseases that can be treated with therapeutics of the present invention include, but are not limited to Alzheimer's disease, spinal cord injury, amyotrophic lateral sclerosis, cystic fibrosis, heart disease, including ischemic and dilated cardiomyopathy, macular degeneration, Parkinson's disease, Huntington's disease, diabetes, sickle-cell anemia, thalassemia, Fanconi anemia, xeroderma pigmentosum, muscular dystrophy, severe combined immunodeficiency, hereditary sensory neuropathy, cancer, and HIV/AIDS. In certain embodiments, the therapeutic comprises a cosmetic. In one embodiment, a cell is harvested from a patient, the cell is reprogrammed and expanded to a large number of adipose cells, thus producing a cosmetic, and the cosmetic is introduced into the patient. In still another embodiment, the cosmetic is used for tissue reconstruction.

While detailed examples are provided herein for the production of specific types of cells and for the production of therapeutics comprising specific types of cells, it is recognized that the methods of the present invention can be used to produce many other types of cells, and to produce therapeutics comprising one or more of many other types of cells, for example, by reprogramming a cell according to the methods of the present invention, and culturing the cell under conditions that mimic one or more aspects of development by providing conditions that resemble the conditions present in the cellular microenvironment during development.

Certain embodiments are directed to a library of cells with a variety of human leukocyte antigen (HLA) types ("HLA-matched libraries"). An HLA-matched library may be beneficial in part because it can provide for the rapid production and/or distribution of therapeutics without the patient having to wait for a therapeutic to be produced from the patient's cells. Such a library may be particularly beneficial for the treatment of heart disease and diseases of the blood and/or immune system for which patients may benefit from the immediate availability of a therapeutic.

Certain embodiments are directed to a cell that is used for tissue/organ modeling and/or disease modeling. In one embodiment, a skin cell is reprogrammed and expanded to a large number of cardiac cells, and the cardiac cells are used for screening bioactive molecules for cardiotoxicity (an example of safety testing). In another embodiment, a skin cell from a patient with Alzheimer's disease is reprogrammed and expanded to a large number of cortical neurons, and the cortical neurons are used for screening bioactive molecules for reducing the accumulation of insoluble plaques (an example of efficacy testing). Certain embodiments of the present invention are therefore useful for safety testing and/or efficacy testing.

Certain embodiments are directed to a method for encapsulating cells and/or seeding cells in a scaffold, and to cells that are encapsulated and/or cells that are seeded in a scaffold. In certain situations, encapsulating cells may be beneficial, in part because encapsulated cells may be less immunogenic than non-encapsulated cells. In one embodiment, a cell is reprogrammed to a glucose-responsive insulin-producing cell, the glucose-responsive insulin-producing cell is encapsulated in a material such as alginate, and the encapsulated glucose-responsive insulin-producing cell is introduced into a patient with type 1 diabetes. In another embodiment, the introducing is by intraperitoneal injection or intraportal injection. In certain situations, seeding cells in a scaffold may be beneficial, in part because a scaffold can provide mechanical stability. In one embodiment, a cell is reprogrammed and expanded into a large number of fibroblasts and keratinocytes, the fibroblasts and keratinocytes are seeded in a scaffold comprising collagen, and the seeded scaffold is applied to a wound, forming a synthetic skin graft. In another embodiment, a cell is reprogrammed, the reprogrammed cell is mixed with a scaffold in liquid or slurry form, the mixture is introduced into the patient, and the stiffness of the scaffold increases upon or after introduction.

Certain embodiments are directed to a method for purifying cells. Transfecting, reprogramming, and gene-editing can often produce populations of cells that include cells with the desired phenotype and cells with one or more undesired phenotypes. Certain embodiments are therefore directed to a method for purifying transfected, reprogrammed, and/or gene-edited cells. In one embodiment, the cells are purified using a density gradient. In another embodiment, the cells are purified by contacting the cells with one or more antibodies that allows the separation of cells having one or more desired phenotypes from cells having one or more undesired phenotypes. In another embodiment, the antibody is bound to a substrate, preferably a magnetic bead. In yet another embodiment, the antibody is bound to a fluorescent molecule, and the separation is performed by fluorescence activated cell sorting (FACS) or other similar means. In another embodiment, cells with an undesired phenotype are prevented from proliferating, preferably by contacting the cells with one or more molecules that prevents the cells from dividing, preferably mitomycin-c, 5-aza-deoxycytidine, fluorouracil or a biologically active analogue or derivative thereof. Other embodiments are directed to a therapeutic comprising cells that are purified to enrich the fraction of cells having one or more desired phenotypes.

Certain embodiments are directed to a method for producing animal models, including models of mutations and diseases. In one embodiment, an animal skin cell is gene-edited and reprogrammed to a pluripotent stem cell. In another embodiment, about 1-100 reprogrammed and gene-edited cells are injected into a blastocyst, and the blastocyst is implanted into the uterine horn of an animal. In one embodiment, the animal is selected from the group: a cat, a dog, a mouse, a pig, a horse, a cow, a chicken, a sheep, a goat, a fish, a primate, and a rat. In another embodiment, the animal is a rat.

Certain non-canonical nucleotides, when incorporated into synthetic RNA molecules, can reduce the toxicity of the synthetic RNA molecules, in part by interfering with binding of proteins that detect exogenous nucleic acids, for example, protein kinase R, Rig-1 and the oligoadenylate synthetase family of proteins. Non-canonical nucleotides that have been reported to reduce the toxicity of synthetic RNA molecules when incorporated therein include: pseudouridine, 5-methyluridine, 2-thiouridine, 5-methylcytidine, N6-methyladenosine, and certain combinations thereof. However, the chemical characteristics of non-canonical nucleotides that can enable them to lower the toxicity of synthetic RNA molecules have, until this point, remained unknown. Furthermore, incorporation of large amounts of most non-canonical nucleotides, for example, 5-methyluridine, 2-thiouridine, 5-methylcytidine, and N6-methyladenosine, can reduce the efficiency with which synthetic RNA molecules can be translated into protein, limiting the utility of synthetic RNA molecules containing these nucleotides in applications that require protein expression. In addition, while pseudouridine can be completely substituted for uridine in synthetic RNA molecules without reducing the efficiency with which the synthetic RNA molecules can be translated into protein, in certain situations, for example, when performing frequent, repeated transfections, synthetic RNA molecules containing only adenosine, guanosine, cytidine, and pseudouridine can exhibit excessive toxicity.

It has now been discovered that synthetic RNA molecules containing one or more non-canonical nucleotides that include one or more substitutions at the 2C and/or 4C and/or 5C positions in the case of a pyrimidine or the 6C and/or 7N and/or 8C positions in the case of a purine can be less toxic than synthetic RNA molecules containing only canonical nucleotides, due in part to the ability of substitutions at these positions to interfere with recognition of synthetic RNA molecules by proteins that detect exogenous nucleic acids, and furthermore, that substitutions at these positions can have minimal impact on the efficiency with which the synthetic RNA molecules can be translated into protein, due in part to the lack of interference of substitutions at these positions with base-pairing and base-stacking interactions.

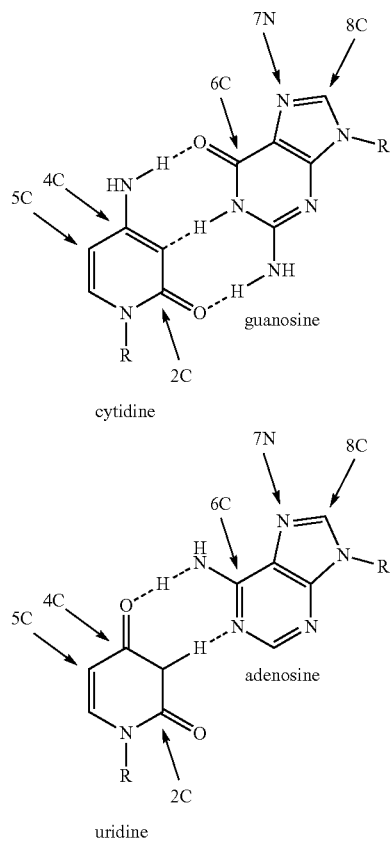

Examples of non-canonical nucleotides that include one or more substitutions at the 2C and/or 4C and/or 5C positions in the case of a pyrimidine or the 6C and/or 7N and/or 8C positions in the case of a purine include, but are not limited to: 2-thiouridine, 5-azauridine, pseudouridine, 4-thiouridine, 5-methyluridine, 5-aminouridine, 5-hydroxyuridine, 5-methyl-5-azauridine, 5-amino-5-azauridine, 5-hydroxy-5-azauridine, 5-methylpseudouridine, 5-aminopseudouridine, 5-hydroxypseudouridine, 4-thio-5-azauridine, 4-thiopseudouridine, 4-thio-5-methyluridine, 4-thio-5-aminouridine, 4-thio-5-hydroxyuridine, 4-thio-5-methyl-5-azauridine, 4-thio-5-amino-5-azauridine, 4-thio-5-hydroxy-5-azauridine, 4-thio-5-methylpseudouridine, 4-thio-5-aminopseudouridine, 4-thio-5-hydroxypseudouridine, 2-thiocytidine, 5-azacytidine, pseudoisocytidine, N4-methylcytidine, N4-aminocytidine, N4-hydroxycytidine, 5-methylcytidine, 5-aminocytidine, 5-hydroxycytidine, 5-methyl-5-azacytidine, 5-amino-5-azacytidine, 5-hydroxy-5-azacytidine, 5-methylpseudoisocytidine, 5-aminopseudoisocytidine, 5-hydroxypseudoisocytidine, N4-methyl-5-azacytidine, N4-methylpseudoisocytidine, 2-thio-5-azacytidine, 2-thiopseudoisocytidine, 2-thio-N4-methylcytidine, 2-thio-N4-aminocytidine, 2-thio-N4-hydroxycytidine, 2-thio-5-methylcytidine, 2-thio-5-aminocytidine, 2-thio-5-hydroxycytidine, 2-thio-5-methyl-5-azacytidine, 2-thio-5-amino-5-azacytidine, 2-thio-5-hydroxy-5-azacytidine, 2-thio-5-methylpseudoisocytidine, 2-thio-5-aminopseudoisocytidine, 2-thio-5-hydroxypseudoisocytidine, 2-thio-N4-methyl-5-azacytidine, 2-thio-N4-methylpseudoisocytidine, N4-methyl-5-methylcytidine, N4-methyl-5-aminocytidine, N4-methyl-5-hydroxycytidine, N4-methyl-5-methyl-5-azacytidine, N4-methyl-5-amino-5- azacytidine, N4-methyl-5-hydroxy-5-azacytidine, N4-methyl-5-methylpseudoisocytidine, N4-methyl-5-aminopseudoisocytidine, N4-methyl-5-hydroxypseudoisocytidine, N4-amino-5-azacytidine, N4-aminopseudoisocytidine, N4-amino-5-methylcytidine, N4-amino-5-aminocytidine, N4-amino-5-hydroxycytidine, N4-amino-5-methyl-5-azacytidine, N4-amino-5-amino-5-azacytidine, N4-amino-5-hydroxy-5-azacytidine, N4-amino-5-methylpseudoisocytidine, N4-amino-5-aminopseudoisocytidine, N4-amino-5-hydroxypseudoisocytidine, N4-hydroxy-5-azacytidine, N4-hydroxypseudoisocytidine, N4-hydroxy-5-methylcytidine, N4-hydroxy-5-aminocytidine, N4-hydroxy-5-hydroxycytidine, N4-hydroxy-5-methyl-5-azacytidine, N4-hydroxy-5-amino-5-azacytidine, N4-hydroxy-5-hydroxy-5-azacytidine, N4-hydroxy-5-methylpseudoisocytidine, N4-hydroxy-5-aminopseudoisocytidine, N4-hydroxy-5-hydroxypseudoisocytidine, 2-thio-N4-methyl-5-methylcytidine, 2-thio-N4-methyl-5-aminocytidine, 2-thio-N4-methyl-5-hydroxycytidine, 2-thio-N4-methyl-5-methyl-5-azacytidine, 2-thio-N4-methyl-5-amino-5-azacytidine, 2-thio-N4-methyl-5-hydroxy-5-azacytidine, 2-thio-N4-methyl-5-methylpseudoisocytidine, 2-thio-N4-methyl-5-aminopseudoisocytidine, 2-thio-N4-methyl-5-hydroxypseudoisocytidine, 2-thio-N4-amino-5-azacytidine, 2-thio-N4-aminopseudoisocytidine, 2-thio-N4-amino-5-methylcytidine, 2-thio-N4-amino-5-aminocytidine, 2-thio-N4-amino-5-hydroxycytidine, 2-thio-N4-amino-5-methyl-5-azacytidine, 2-thio-N4-amino-5-amino-5-azacytidine, 2-thio-N4-amino-5-hydroxy-5-azacytidine, 2-thio-N4-amino-5-methylpseudoisocytidine, 2-thio-N4-amino-5-aminopseudoisocytidine, 2-thio-N4-amino-5-hydroxypseudoisocytidine, 2-thio-N4-hydroxy-5-azacytidine, 2-thio-N4-hydroxypseudoisocytidine, 2-thio-N4-hydroxy-5-methylcytidine, N4-hydroxy-5-aminocytidine, 2-thio-N4-hydroxy-5-hydroxycytidine, 2-thio-N4-hydroxy-5-methyl-5-azacytidine, 2-thio-N4-hydroxy-5-amino-5-azacytidine, 2-thio-N4-hydroxy-5-hydroxy-5-azacytidine, 2-thio-N4-hydroxy-5-methylpseudoisocytidine, 2-thio-N4-hydroxy-5-aminopseudoisocytidine, 2-thio-N4-hydroxy-5-hydroxypseudoisocytidine, N6-methyladenosine, N6-aminoadenosine, N6-hydroxyadenosine, 7-deazaadenosine, 8-azaadenosine, N6-methyl-7-deazaadenosine, N6-methyl-8-azaadenosine, 7-deaza-8-azaadenosine, N6-methyl-7-deaza-8-azaadenosine, N6-amino-7-deazaadenosine, N6-amino-8-azaadenosine, N6-amino-7-deaza-8-azaadenosine, N6-hydroxyadenosine, N6-hydroxy-7-deazaadenosine, N6-hydroxy-8-azaadenosine, N6-hydroxy-7-deaza-8-azaadenosine, 6-thioguanosine, 7-deazaguanosine, 8-azaguanosine, 6-thio-7-deazaguanosine, 6-thio-8-azaguanosine, 7-deaza-8-azaguanosine, and 6-thio-7-deaza-8-azaguanosine. Note that alternative naming schemes exist for certain non-canonical nucleotides. For example, in certain situations, 5-methylpseudouridine can be referred to as "3-methylpseudouridine" or "N3-methylpseudouridine".

Nucleotides that contain the prefix "amino" can refer to any nucleotide that contains a nitrogen atom bound to the atom at the stated position of the nucleotide, for example, 5-aminocytidine can refer to 5-aminocytidine, 5-methylaminocytidine, and 5-nitrocytidine. Similarly, nucleotides that contain the prefix "methyl" can refer to any nucleotide that contains a carbon atom bound to the atom at the stated position of the nucleotide, for example, 5-methylcytidine can refer to 5-methylcytidine, 5-ethylcytidine, and 5-hydroxymethylcytidine, nucleotides that contain the prefix "thio" can refer to any nucleotide that contains a sulfur atom bound to the atom at the given position of the nucleotide, and nucleotides that contain the prefix "hydroxy" can refer to any nucleotide that contains an oxygen atom bound to the atom at the given position of the nucleotide.

Certain embodiments are therefore directed to a synthetic RNA molecule, wherein the synthetic RNA molecule contains one or more nucleotides that includes one or more substitutions at the 2C and/or 4C and/or 5C positions in the case of a pyrimidine or the 6C and/or 7N and/or 8C positions in the case of a purine. Other embodiments are directed to a therapeutic, wherein the therapeutic contains one or more synthetic RNA molecules, and wherein the one or more synthetic RNA molecules contains one or more nucleotides that includes one or more substitutions at the 2C and/or 4C and/or 5C positions in the case of a pyrimidine or the 6C and/or 7N and/or 8C positions in the case of a purine. In one embodiment, the therapeutic comprises a transfection reagent. In another embodiment, the transfection reagent comprises a cationic lipid, liposome or micelle. In still another embodiment, the liposome or micelle comprises folate and the therapeutic composition has anti-cancer activity. In another embodiment, the one or more nucleotides includes at least one of pseudouridine, 2-thiouridine, 4-thiouridine, 5-azauridine, 5-hydroxyuridine, 5-methyluridine, 5-aminouridine, 2-thiopseudouridine, 4-thiopseudouridine, 5-hydroxypseudouridine, 5-methylpseudouridine, 5-aminopseudouridine, pseudoisocytidine, N4-methylcytidine, 2-thiocytidine, 5-azacytidine, 5-hydroxycytidine, 5-aminocytidine, 5-methylcytidine, N4-methylpseudoisocytidine, 2-thiopseudoisocytidine, 5-hydroxypseudoisocytidine, 5-aminopseudoisocytidine, 5-methylpseudoisocytidine, 7-deazaadenosine, 7-deazaguanosine, 6-thioguanosine, and 6-thio-7-deazaguanosine. In another embodiment, the one or more nucleotides includes at least one of pseudouridine, 2-thiouridine, 4-thiouridine, 5-azauridine, 5-hydroxyuridine, 5-methyluridine, 5-aminouridine, 2-thiopseudouridine, 4-thiopseudouridine, 5-hydroxypseudouridine, 5-methylpseudouridine, and 5-aminopseudouridine and at least one of pseudoisocytidine, N4-methylcytidine, 2-thiocytidine, 5-azacytidine, 5-hydroxycytidine, 5-aminocytidine, 5-methylcytidine, N4-methylpseudoisocytidine, 2-thiopseudoisocytidine, 5-hydroxypseudoisocytidine, 5-aminopseudoisocytidine, and 5-methylpseudoisocytidine. In still another embodiment, the one or more nucleotides include at least one of pseudouridine, 2-thiouridine, 4-thiouridine, 5-azauridine, 5-hydroxyuridine, 5-methyluridine, 5-aminouridine, 2-thiopseudouridine, 4-thiopseudouridine, 5-hydroxypseudouridine, and 5-methylpseudouridine, 5-aminopseudouridine and at least one of pseudoisocytidine, N4-methylcytidine, 2-thiocytidine, 5-azacytidine, 5-hydroxycytidine, 5-aminocytidine, 5-methylcytidine, N4-methylpseudoisocytidine, 2-thiopseudoisocytidine, 5-hydroxypseudoisocytidine, 5-aminopseudoisocytidine, and 5-methylpseudoisocytidine and at least one of 7-deazaguanosine, 6-thioguanosine, and 6-thio-7-deazaguanosine. In yet another embodiment, the one or more nucleotides includes: 5-methylcytidine and 7-deazaguanosine. In another embodiment, the one or more nucleotides also includes pseudouridine or 4-thiouridine or 5-methyluridine or 5-aminouridine or 4-thiopseudouridine or 5-methylpseudouridine or 5-aminopseudouridine. In a still another embodiment, the one or more nucleotides also includes 7-deazaadenosine. In another embodiment, the one or more nucleotides includes: pseudoisocytidine and 7-deazaguanosine and 4-thiouridine. In yet another embodiment, the one or more nucleotides includes: pseudoisocytidine or 7-deazaguanosine and pseudouridine. In still another embodiment, the one or more nucleotides includes: 5-methyluridine and 5-methylcytidine and 7-deazaguanosine. In a further embodiment, the one or more nucleotides includes: pseudouridine or 5-methylpseudouridine and 5-methylcytidine and 7-deazaguanosine. In another embodiment, the one or more nucleotides includes: pseudoisocytidine and 7-deazaguanosine and pseudouridine.

Certain non-canonical nucleotides can be incorporated more efficiently than other non-canonical nucleotides into synthetic RNA molecules by RNA polymerases that are commonly used for in vitro transcription, due in part to the tendency of these certain non-canonical nucleotides to participate in standard base-pairing interactions and base-stacking interactions, and to interact with the RNA polymerase in a manner similar to that in which the corresponding canonical nucleotide interacts with the RNA polymerase. As a result, certain nucleotide mixtures containing one or more non-canonical nucleotides can be beneficial in part because in vitro-transcription reactions containing these nucleotide mixtures can yield a large quantity of synthetic RNA. Certain embodiments are therefore directed to a nucleotide mixture containing one or more nucleotides that includes one or more substitutions at the 2C and/or 4C and/or 5C positions in the case of a pyrimidine or the 6C and/or 7N and/or 8C positions in the case of a purine. Nucleotide mixtures include, but are not limited to (numbers preceding each nucleotide indicate an exemplary fraction of the non-canonical nucleotide triphosphate in an in vitro-transcription reaction, for example, 0.2 pseudoisocytidine refers to a reaction containing adenosine-5'-triphosphate, guanosine-5'-triphosphate, uridine-5'-triphosphate, cytidine-5 '-triphosphate, and pseudoisocytidine-5'-triphosphate, wherein pseudoisocytidine-5'-triphosphate is present in the reaction at an amount approximately equal to 0.2 times the total amount of pseudoisocytidine-5'-triphosphate+cytidine-5'-triphosphate that is present in the reaction, with amounts measured either on a molar or mass basis, and wherein more than one number preceding a nucleoside indicates a range of exemplary fractions): 1.0 pseudouridine, 0.1-0.8 2-thiouridine, 0.1-0.8 5-methyluridine, 0.2-1.0 5-hydroxyuridine, 0.1-1.0 5-aminouridine, 0.1-1.0 4-thiouridine, 0.1-1.0 2-thiopseudouridine, 0.1-1.0 4-thiopseudouridine, 0.1-1.0 5-hydroxypseudouridine, 0.2-1 5-methylpseudouridine, 0.1-1.0 5-aminopseudouridine, 0.2-1.0 2-thiocytidine, 0.1-0.8 pseudoisocytidine, 0.2-1.0 5-methylcytidine, 0.2-1.0 5-hydroxycytidine, 0.1-1.0 5-aminocytidine, 0.2-1.0 N4-methylcytidine, 0.2-1.0 5-methylpseudoisocytidine, 0.2-1.0 5-hydroxypseudoisocytidine, 0.2-1.0 5-aminopseudoisocytidine, 0.2-1.0 N4-methylpseudoisocytidine, 0.2-1.0 2-thiopseudoisocytidine, 0.2-1.0 7-deazaguanosine, 0.2-1.0 6-thioguanosine, 0.2-1.0 6-thio-7-deazaguanosine, 0.2-1.0 8-azaguanosine, 0.2-1.0 7-deaza-8-azaguanosine, 0.2-1.0 6-thio-8-azaguanosine, 0.1-0.5 7-deazaadenosine, and 0.1-0.5 N6-methyladenosine.

It has now been discovered that combining certain non-canonical nucleotides can be beneficial in part because the contribution of non-canonical nucleotides to lowering the toxicity of synthetic RNA molecules can be additive. Certain embodiments are therefore directed to a nucleotide mixture, wherein the nucleotide mixture contains more than one of the non-canonical nucleotides listed above, for example, the nucleotide mixture contains both pseudoisocytidine and 7-deazaguanosine or the nucleotide mixture contains both N4-methylcytidine and 7-deazaguanosine, etc. In one embodiment, the nucleotide mixture contains more than one of the non-canonical nucleotides listed above, and each of the non-canonical nucleotides is present in the mixture at the fraction listed above, for example, the nucleotide mixture contains 0.1-0.8 pseudoisocytidine and 0.2-1.0 7-deazaguanosine or the nucleotide mixture contains 0.2-1.0 N4-methylcytidine and 0.2-1.0 7-deazaguanosine, etc.

In certain situations, for example, when it may not be necessary or desirable to maximize the yield of an in vitro-transcription reaction, nucleotide fractions other than those given above may be used. The exemplary fractions and ranges of fractions listed above relate to nucleotide-triphosphate solutions of typical purity (greater than 90% purity). Larger fractions of these and other nucleotides can be used by using nucleotide-triphosphate solutions of greater purity, for example, greater than about 95% purity or greater than about 98% purity or greater than about 99% purity or greater than about 99.5% purity, which can be achieved, for example, by purifying the nucleotide triphosphate solution using existing chemical-purification technologies such as high-pressure liquid chromatography (HPLC) or by other means. In one embodiment, nucleotides with multiple isomers are purified to enrich the desired isomer.

Other embodiments are directed to a method for inducing a cell to express a protein of interest by contacting the cell with a synthetic RNA molecule that contains one or more non-canonical nucleotides that includes one or more substitutions at the 2C and/or 4C and/or 5C positions in the case of a pyrimidine or the 6C and/or 7N and/or 8C positions in the case of a purine. Still other embodiments are directed to a method for transfecting, reprogramming, and/or gene-editing a cell by contacting the cell with a synthetic RNA molecule that contains one or more non-canonical nucleotides that includes one or more substitutions at the 2C and/or 4C and/or 5C positions in the case of a pyrimidine or the 6C and/or 7N and/or 8C positions in the case of a purine. In one embodiment, the synthetic RNA molecule is produced by in vitro transcription. In one embodiment, the synthetic RNA molecule encodes one or more reprogramming factors. In another embodiment, the one or more reprogramming factors includes Oct4 protein. In another embodiment, the cell is also contacted with a synthetic RNA molecule that encodes Sox2 protein. In yet another embodiment, the cell is also contacted with a synthetic RNA molecule that encodes Klf4 protein. In yet another embodiment, the cell is also contacted with a synthetic RNA molecule that encodes c-Myc protein. In yet another embodiment, the cell is also contacted with a synthetic RNA molecule that encodes Lin28 protein.

Enzymes such as T7 RNA polymerase may preferentially incorporate canonical nucleotides in an in vitro-transcription reaction containing both canonical and non-canonical nucleotides. As a result, an in vitro-transcription reaction containing a certain fraction of a non-canonical nucleotide may yield RNA containing a different, often lower, fraction of the non-canonical nucleotide than the fraction at which the non-canonical nucleotide was present in the reaction. In certain embodiments, references to nucleotide incorporation fractions (for example, "a synthetic RNA molecule containing 50% pseudoisocytidine" or "0.1-0.8 pseudoisocytidine") therefore can refer both to RNA molecules containing the stated fraction of the nucleotide, and to RNA molecules synthesized in a reaction containing the stated fraction of the nucleotide (or nucleotide derivative, for example, nucleotide-triphosphate), even though such a reaction may yield RNA containing a different fraction of the nucleotide than the fraction at which the non-canonical nucleotide was present in the reaction.

Different nucleotide sequences can encode the same protein by utilizing alternative codons. In certain embodiments, references to nucleotide incorporation fractions therefore can refer both to RNA molecules containing the stated fraction of the nucleotide, and to RNA molecules encoding the same protein as a different RNA molecule, wherein the different RNA molecule contains the stated fraction of the nucleotide.

Certain embodiments are directed to a kit containing one or more materials needed to practice the present invention. In one embodiment, the kit contains synthetic RNA molecules. In one embodiment, the kit contains synthetic RNA molecules that encode one or more reprogramming factors and/or gene-editing proteins. In another embodiment, the synthetic RNA molecules contain one or more non-canonical nucleotides that include one or more substitutions at the 2C and/or 4C and/or 5C positions in the case of a pyrimidine or the 6C and/or 7N and/or 8C positions in the case of a purine. In another embodiment, the kit contains one or more of: a transfection medium, a transfection reagent, a complexation medium, and a coating solution. In one embodiment, the coating solution contains fibronectin and/or vitronectin, preferably recombinant fibronectin and/or recombinant vitronectin. In one embodiment, one or more of the components of the kit are present as a plurality of aliquots. In one embodiment, the kit contains aliquots of nucleic acid transfection-reagent complexes. In another embodiment, the kit contains aliquots of nucleic acid transfection-reagent complexes that are provided in a solid form, for example, as frozen or freeze-dried pellets. In yet another embodiment, the kit contains aliquots of medium, wherein each aliquot contains transfection reagent-nucleic acid complexes that are stabilized either by chemical treatment or by freezing.

Transfection, in general, and reprogramming, in particular, can be difficult and time-consuming techniques that can be repetitive and prone to error. However, these techniques are often performed manually due to the lack of automated transfection equipment. Certain embodiments are therefore directed to a system that can transfect, reprogram, and/or gene-edit cells in an automated or semi-automated manner.

Referring now to FIG. 9A through FIG. 11, certain embodiments are directed to a system (1) capable of transfecting cells in a multi-well plate (2). In one embodiment, the plate is loaded into a tray (3) that slides out from the system. In another embodiment, the system is capable of storing multiple plates (12). In yet another embodiment, the system comprises a means (4) to store a transfection medium. In one embodiment, the system comprises a means to store the medium at a defined temperature, preferably between 2 C and 6 C. In one embodiment, the system comprises a means (5) to store liquid, waste, and/or cells removed from the wells. In another embodiment, the system comprises a connection to supply power (6). In yet another embodiment, the system comprises a port (33) to communicate with a computer (34). In one embodiment, the port is a USB port. In one embodiment, the system comprises an outtake fan (7). In another embodiment, the system comprises a connection to supply a vacuum (8).

Cell viability can benefit from controlling the environment around the cells. Certain embodiments are therefore directed to a system comprising a means for incubating cells at a specified or desired temperature. In one embodiment, the cells are incubated at one or more temperatures that are between 35 C and 39 C. In one embodiment, the cells are incubated at a temperature of about 37 C. Other embodiments are directed to a system comprising a means for controlling the atmosphere in which cells are incubated. In one embodiment, the system comprises a means for regulating the carbon dioxide concentration of the atmosphere. In one embodiment, the carbon dioxide concentration is between 3% and 7%, preferably about 5%. In another embodiment, the system comprises a means for regulating the oxygen concentration of the atmosphere. In one embodiment, the system regulates the oxygen concentration by introducing nitrogen. In still another embodiment, the oxygen concentration is between about 3% and about 7%, such as about 5%. In one embodiment, the system comprises a means for controlling both the oxygen and carbon dioxide concentrations of the atmosphere in which the cells are incubated. In another embodiment, the system comprises a connection to supply carbon dioxide (9). In yet another embodiment, the system comprises a connection to supply nitrogen (10). In yet another embodiment, the system comprises a connection to supply oxygen (11).

Certain embodiments are directed to a system comprising a means for dispensing nucleic acid transfection-reagent complexes and/or media (24). In one embodiment, the system comprises one or more front-loaded pipettes that can dispense complexes and/or media. Examples of other means for dispensing complexes include, but are not limited to: a back-loaded pipette, a peristaltic pump, a microfluidic device, an electrospray nozzle, a piezoelectric ejector, and an acoustic droplet ejector. Certain embodiments are directed to a system comprising a means for generating nucleic acid transfection-reagent complexes (13). In one embodiment, the system comprises a means for combining one or more transfection reagents (14) and one or more nucleic acids (15). In one embodiment, the means for combining comprises one or more front-loaded pipettes. Examples of other means that can be used for combining include, but are not limited to: a back-loaded pipette, a peristaltic pump, a microfluidic device, an electrospray nozzle, a piezoelectric ejector, and an acoustic droplet ejector. In one embodiment, the system comprises one or more removable tips. In another embodiment, the one or more removable tips can be sterilized. In another embodiment the one or more removable tips are disposable. In yet another embodiment, the one or more removable tips are made of plastic or glass. In still another embodiment, the plastic is polypropylene. In one embodiment, the system comprises a means for incubating one or more nucleic acids with one or more transfection reagents in one or more complexation media (16). In another embodiment, the system comprises a means for storing one or more nucleic acids, one or more transfection reagents, and one or more complexation media. In one embodiment, the complexation occurs at room temperature. In one embodiment, the system comprises a means for warming the medium prior to contacting the cells with the medium, for example to between about 20° C. and about 39° C., or to between about 30° C. and about 39° C. In one embodiment, the medium is warmed using a heating element (25). In one embodiment, the system comprises a means for storing and/or dispensing multiple culture media.

Certain embodiments are directed to a method for storing nucleic acid transfection-reagent complexes. In one embodiment, one or more nucleic acids and one or more transfection reagents are combined with one or more complexation media and are cooled to generate a nucleic acid transfection-reagent pellet. In one embodiment, the cooling is performed by contacting with liquid nitrogen. Other cooling methods include, but are not limited to, contacting with: a Peltier cooler, cooled liquid propane, cooled liquid ethane, and a cooled polished metal surface. In one embodiment, the method is substantially free of RNase. Certain embodiments are directed to a method for transfecting cells using a nucleic acid transfection-reagent pellet. In one embodiment, the pellet is warmed prior to being added to the transfection medium. In one embodiment, the pellet is warmed by placing the pellet in a small volume of warm transfection medium that is then contacted with the cells to be transfected. In another embodiment, the pellet is added directly to the transfection medium. Certain embodiments are directed to a system that can perform transfection using nucleic acid transfection-reagent pellets. In one embodiment, the system comprises a means for storing the pellets (17) within a defined temperature range. In one embodiment, the temperature range is between about −90° C. and about 0° C., preferably between about −30° C. and about −4° C. In one embodiment, the system comprises a means for dispensing pellets. In one embodiment, the pellets are dispensed using a plunger (19). In another embodiment, the pellets are dispensed using a rotating disk (20) that contains an opening (21) through which the pellets are dispensed. In one embodiment, the apparatus comprises a means for warming the pellet prior to adding the pellet to the transfection medium. In one embodiment, the pellet is warmed by placing the pellet in a small container (22) containing warm transfection medium that is then contacted with the cells to be transfected. In another embodiment, the apparatus contains a means for dispensing the pellet directly into the transfection medium. In yet another embodiment, the pellets are stored in a cartridge (16). In one embodiment, the system comprises a means for replacing cartridges (36).

During cell culture it may be beneficial to replace, either in whole or in part, the culture medium or to supplement the culture medium with an additional amount of medium or other supplement in order to add nutrients and/or to reduce, remove, or otherwise inactivate cellular waste or other undesirable components that may be present in the medium, including residual complexes. Certain embodiments are therefore directed to a system comprising a means (23) for removing, in whole or in part, the culture medium from the cells. In one embodiment, the system comprises an aspirator.

Certain embodiments are directed to a system comprising a means for removing the lid of a well plate. In one embodiment, the system comprises a means for removing the lid of a well plate (26) using suction (27). Other means for removing the lid of a well plate include, but are not limited to: an adhesive, an articulated appendage (28), a clamp, a magnet, and an electromagnet. In certain embodiments, the system comprises a means for imaging the cells (29). In one embodiment, the cell density is determined by measuring the optical density of the vessel containing the cells. In another embodiment, the cell density is determined by imaging the cells.

Certain embodiments are directed to a system that is used in operable combination with other equipment, for example, equipment for culturing, imaging, or otherwise manipulating cells. In one embodiment, the system (1) is loaded using a robotic arm (30). In another embodiment, a robotic arm is used to transfer plates to and/or from an incubator (31). In yet another embodiment, a plate imager (32) is used to image the cells. In yet another embodiment, the system is controlled using a computer (34). In one embodiment, the system is used for transfecting, reprogramming, and/or gene-editing cells.

The present invention therefore has the aim of providing products for both research and therapeutic use.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

EXAMPLES

Example 1 RNA Synthesis

Figure 1:
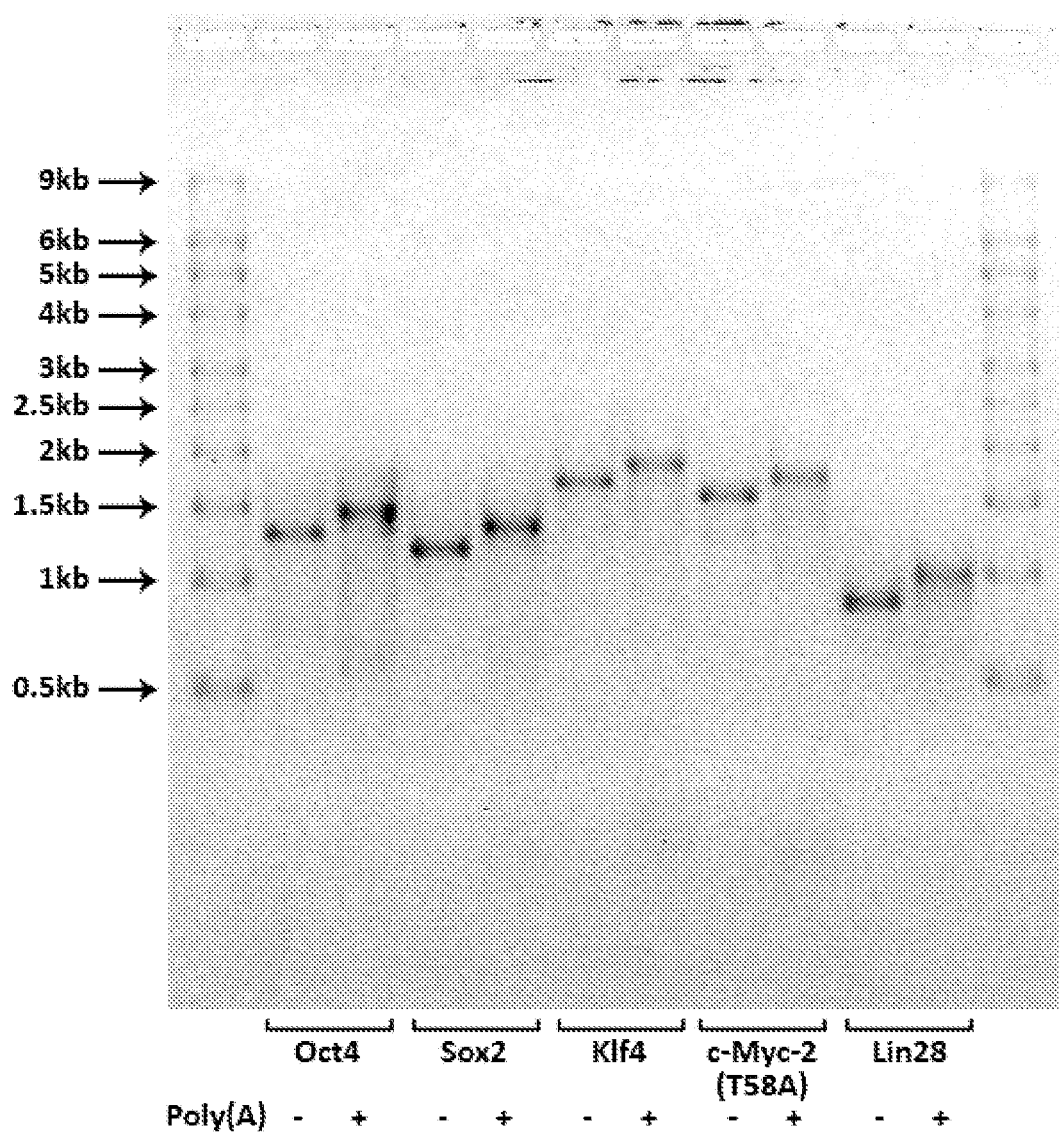

RNA encoding the human proteins Oct4, Sox2, Klf4, c-Myc-2 (T58A), and Lin28 and comprising various combinations of canonical and non-canonical nucleotides, was synthesized from DNA templates (Table 1). Samples of the RNA were analyzed by agarose gel electrophoresis to assess the quality of the RNA (FIG. 1). The RNA was then diluted to between 100 ng/µL and 500 ng/µL. For certain experiments, an RNase inhibitor (Superase•In™, Life Technologies Corporation) was added at a concentration of 1 µL/100 µg of RNA. RNA solutions were stored at 4 C. For certain experiments involving RNA mixtures, RNA encoding Oct4, Sox2, Klf4, c-Myc-2 (T58A), and Lin28 was mixed at a molar ratio of 3:1:1:1:1.

TABLE 1

| Template | Nucleotides | Reaction Volume/ µL | ivT Yield/ µg |
|---|---|---|---|
| Oct4 | A, G, psU, 5mC | 210 | 1976.0 |
| Sox2 | A, G, psU, 5mC | 70 | 841.7 |
| Klf4 | A, G, psU, 5mC | 70 | 950.0 |
| c-Myc-2 (T58A) | A, G, psU, 5mC | 70 | 535.8 |
| Lin28 | A, G, psU, 5mC | 70 | 551.0 |
| Oct4 | A, G, psU, 5mC | 105 | 1181.8 |
| Sox2 | A, G, psU, 5mC | 35 | 533.9 |
| Klf4 | A, G, psU, 5mC | 35 | 552.9 |
| c-Myc-2 (T58A) | A, G, psU, 5mC | 35 | 471.2 |
| Lin28 | A, G, psU, 5mC | 35 | 440.8 |
| Oct4 | A, G, psU, 5mC | 105 | 1155.2 |
| Sox2 | A, G, psU, 5mC | 35 | 526.3 |
| Klf4 | A, G, psU, 5mC | 35 | 494.0 |
| c-Myc-2 (T58A) | A, G, psU, 5mC | 35 | 446.5 |
| Lin28 | A, G, psU, 5mC | 35 | 389.5 |
| Sox2 | A, G, psU, 5mC | 20 | 143.8 |
| Sox2 | A, G, U, psisoC | 20 | 114.1 |
| Sox2 | A, G, 0.25 2sU, psisoC | 20 | 78.0 |
| Sox2 | A, G, 0.25 2sU, 0.25 psisoC | 20 | 140.1 |
| Sox2 | A, G, 5mU, psisoC | 20 | 30.6 |
| Sox2 | A, G, 0.5 5mU, psisoC | 20 | 65.9 |
| Oct4 | A, G, U, psisoC | 30 | 191.6 |
| Sox2 | A, G, U, psisoC | 10 | 50.7 |
| Klf4 | A, G, U, psisoC | 10 | 74.5 |
| c-Myc-2 (T58A) | A, G, U, psisoC | 10 | 87.2 |
| Lin28 | A, G, U, psisoC | 10 | 86.8 |
| Oct4 | A, G, 0.25 5mU, psisoC | 30 | 195.8 |
| Sox2 | A, G, 0.25 5mU, psisoC | 10 | 36.2 |
| Klf4 | A, G, 0.25 5mU, psisoC | 10 | 33.6 |
| c-Myc-2 (T58A) | A, G, 0.25 5mU, psisoC | 10 | 63.0 |
| Lin28 | A, G, 0.25 5mU, psisoC | 10 | 77.2 |
| Oct4 | A, G, U, C | 30 | 165.2 |
| Sox2 | A, G, U, C | 10 | 94.7 |
| Klf4 | A, G, U, C | 10 | 91.4 |
| c-Myc-2 (T58A) | A, G, U, C | 10 | 84.9 |
| Lin28 | A, G, U, C | 10 | 104.4 |
| Oct4 | A, G, U, 0.25 psisoC | 30 | 161.2 |
| Sox2 | A, G, U, 0.25 psisoC | 10 | 83.8 |
| Klf4 | A, G, U, 0.25 psisoC | 10 | 85.1 |
| c-Myc-2 (T58A) | A, G, U, 0.25 psisoC | 10 | 89.3 |
| Lin28 | A, G, U, 0.25 psisoC | 10 | 94.9 |
| Oct4 | A, G, U, 0.5 psisoC | 30 | 150.8 |

TABLE 1-continued

| Template | Nucleotides | Reaction Volume/ μL | ivT Yield/ μg |
|---|---|---|---|
| Sox2 | A, G, U, 0.5 psisoC | 10 | 79.3 |
| Klf4 | A, G, U, 0.5 psisoC | 10 | 83.8 |
| c-Myc-2 (T58A) | A, G, U, 0.5 psisoC | 10 | 94.7 |
| Lin28 | A, G, U, 0.5 psisoC | 10 | 78.6 |
| Oct4 | 0.25 7dA, G, U, C | 10 | 29.7 |
| Oct4 | 0.5 7dA, G, U, C | 10 | 44.7 |
| Oct4 | A, 0.25 7dG, U, C | 10 | 45.2 |
| Oct4 | A, 0.5 7dG, U, C | 10 | 31.7 |
| Oct4 | 0.25 7dA, 0.25 7dG, U, C | 10 | 13.2 |
| Oct4 | 0.25 7dA, G, U, 0.25 psisoC | 10 | 47.6 |
| Oct4 | A, 0.25 7dG, U, 0.25 psisoC | 10 | 10.5 |
| Oct4 | A, 0.5 7dG, U, 0.25 psisoC | 30 | 125.3 |
| Sox2 | A, 0.5 7dG, U, 0.25 psisoC | 10 | 20.5 |
| Klf4 | A, 0.5 7dG, U, 0.25 psisoC | 10 | 18.4 |
| c-Myc-2 (T58A) | A, 0.5 7dG, U, 0.25 psisoC | 10 | 22.1 |
| Lin28 | A, 0.5 7dG, U, 0.25 psisoC | 10 | 39.7 |
| Oct4 | A, 0.5 7dG, U, 0.5 psisoC | 30 | 92.3 |
| Sox2 | A, 0.5 7dG, U, 0.5 psisoC | 10 | 20.1 |
| Klf4 | A, 0.5 7dG, U, 0.5 psisoC | 10 | 17.7 |
| c-Myc-2 (T58A) | A, 0.5 7dG, U, 0.5 psisoC | 10 | 95.4 |
| Lin28 | A, 0.5 7dG, U, 0.5 psisoC | 10 | 26.0 |
| Oct4 | 0.25 7dA, 7dG, U, 0.25 psisoC | 20 | 3.8 |
| Sox2 | 0.25 7dA, 7dG, U, 0.25 psisoC | 20 | 5.4 |
| Klf4 | 0.25 7dA, 7dG, U, 0.25 psisoC | 20 | 5.9 |
| c-Myc-2 (T58A) | 0.25 7dA, 7dG, U, 0.25 psisoC | 20 | 5.9 |
| Lin28 | 0.25 7dA, 7dG, U, 0.25 psisoC | 20 | 5.1 |
| Oct4 | 0.25 7dA, 7dG, U, 0.5 psisoC | 20 | 3.0 |
| Sox2 | 0.25 7dA, 7dG, U, 0.5 psisoC | 20 | 3.3 |
| Klf4 | 0.25 7dA, 7dG, U, 0.5 psisoC | 20 | 4.1 |
| c-Myc-2 (T58A) | 0.25 7dA, 7dG, U, 0.5 psisoC | 20 | 4.5 |
| Lin28 | 0.25 7dA, 7dG, U, 0.5 psisoC | 20 | 5.0 |
| Oct4 (2 h incubation) | A, 0.75 7dG, U, C | 10 | 40.8 |
| Oct4 (2 h incubation) | A, 7dG, U, C | 10 | 14.1 |
| Oct4 (20 h incubation) | A, 0.75 7dG, U, C | 10 | 42.9 |
| Oct4 (20 h incubation) | A, 7dG, U, C | 10 | 24.4 |
| Oct4 | A, G, U, 0.25 N4mC | 10 | 73.1 |
| Oct4 | A, G, U, 0.5 N4mC | 10 | 66.2 |
| Oct4 | A, G, U, 0.75 N4mC | 10 | 55.1 |
| Oct4 | A, G, U, N4mC | 10 | 32.7 |
| Oct4 | A, 0.75 7dG, U, C | 10 | 35.6 |

"A" refers to adenosine-5'-triphosphate, "G" refers to guanosine-5'-triphosphate, "U" refers to uridine-5'-triphosphate, "C" refers to cytidine-5'-triphosphate, "psU" refers to pseudouridine-5'-triphosphate, "5mC" refers to 5-methylcytidine-5'-triphosphate, "2sU" refers to 2-thiouridine-5'-triphosphate, "psisoC" refers to pseudoisocytidine-5'-triphosphate, "5mU" refers to 5-methyluridine-5'-triphosphate, "7dA" refers to 7-deazaadenosine-5'-triphosphate, "7dG" refers to 7-deazaguanosine-5'-triphosphate, and "N4mC" refers to N4-methylcytidine-5'-triphosphate.

Example 2 Transfection Medium Formulation

A medium was developed to support efficient transfection, reprogramming, and gene-editing of cells:
DMEM/F12+10 μg/mL insulin+5.5 μg/mL transferrin+6.7 ng/mL sodium selenite+20 ng/mL bFGF+5 mg/mL treated human serum albumin.

Variants of this medium were also developed to provide improved performance when used with specific transfection reagents, specific nucleic acids, and specific cell types: DMEM/F12+10 μg/mL insulin+5.5 μg/mL transferrin+6.7 ng/mL sodium selenite+4.5 μg/mL cholesterol+20 ng/mL bFGF+5 mg/mL treated human serum albumin, DMEM/F12+10 μg/mL insulin+5.5 μg/mL transferrin+6.7 ng/mL sodium selenite+1 μM hydrocortisone+20 ng/mL bFGF+5 mg/mL treated human serum albumin, and DMEM/F12+10 μg/mL insulin+5.5 μg/mL transferrin+6.7 ng/mL sodium selenite+4.5 μg/mL cholesterol+1 μM hydrocortisone+20 ng/mL bFGF+5 mg/mL treated human serum albumin.

Examples of additional components that were added to the cell-culture medium in certain experiments (listed with example concentrations) include: 15 mM HEPES, 2 mM L-alanyl-L-glutamine, 2 μg/mL ethanolamine, 10 μg/mL fatty acids, 10 μg/mL cod liver oil fatty acids (methyl esters), 25 μg/mL polyoxyethylenesorbitan monooleate, 2 μg/mL D-alpha-tocopherol acetate, 1-50 μg/mL L-ascorbic acid 2-phosphate sesquimagnesium salt hydrate, 200 ng/mL B18R, and 0.1% Pluronic F-68.

For certain experiments in which the medium was conditioned, the following variant was used:
DMEM/F12+15 mM HEPES+2 mM L-alanyl-L-glutamine+10 μg/mL insulin+5.5 μg/mL transferrin+6.7 ng/mL sodium selenite+2 μg/mL ethanolamine+4.5 μg/mL cholesterol+10 μg/mL cod liver oil fatty acids (methyl esters)+25 μg/mL polyoxyethylenesorbitan monooleate+2 μg/mL D-alpha-tocopherol acetate+1 μg/mL L-ascorbic acid 2-phosphate sesquimagnesium salt hydrate+0.1% Pluronic F-68+20 ng/mL bFGF+5 mg/mL treated human serum albumin.

For certain experiments in which the medium was not conditioned, the following variant was used.
DMEM/F12+15 mM HEPES+2 mM L-alanyl-L-glutamine+10 μg/mL insulin+5.5 μg/mL transferrin+6.7 ng/mL sodium selenite+2 μg/mL ethanolamine+4.5 μg/mL cholesterol+1 μM hydrocortisone+0-25 μg/mL polyoxyethylenesorbitan monooleate+2 μg/mL D-alpha-tocopherol acetate+50 μg/mL L-ascorbic acid 2-phosphate sesquimagnesium salt hydrate+20 ng/mL bFGF+5 mg/mL treated human serum albumin.

For the preparation of the these variants, the treated human serum albumin was treated by addition of 32 mM sodium octanoate, followed by heating at 60 C for 4 h, followed by treatment with ion-exchange resin (AG501-X8 (D)) for 6 h at room temperature, followed by treatment with dextran-coated activated charcoal (C6241, Sigma-Aldrich Co. LLC.) overnight at room temperature, followed by centrifugation, filtering, adjustment to a 10% solution with nuclease-free water, followed by addition to the other components of the medium. For certain experiments in which the medium was conditioned, the medium was conditioned for 24 h on irradiated human neonatal fibroblast feeders. The cells were plated on fibronectin-coated plates or fibronectin and vitronectin-coated plates, unless otherwise noted.

The formulation of the medium can be adjusted to meet the needs of the specific cell types being cultured. Furthermore, in certain situations, treated human serum albumin can be replaced with other treated albumin, for example, treated bovine serum albumin, other glutamine sources can be used instead of or in addition to L-alanyl-L-glutamine, for example, L-glutamine, other buffering systems can be used instead of or in addition to HEPES, for example, phosphate, bicarbonate, etc., selenium can be provided in other forms instead of or in addition to sodium selenite, for example, selenous acid, other antioxidants can be used instead of or in addition to L-ascorbic acid 2-phosphate sesquimagnesium salt hydrate and/or D-alpha-tocopherol acetate, for example, L-ascorbic acid, other surfactants can be used instead of or in addition to polyoxyethylenesorbitan monooleate and/or Pluronic F-68, for example, Pluronic F-127, other basal media can be used instead of or in addition to DMEM/F12, for example, MEM, DMEM, etc., and the components of the culture medium can be varied with time, for example, by using a medium without TGF-β from day 0 to day 5, and then using a medium containing 2 ng/mL TGF-β after day 5. In certain situations, other ingredients can be added, for example, fatty acids, lysophosphatidic acid, lysosphingomyelin, sphingosine-1-phosphate, other sphingolipids, members of the TGF-β/NODAL family of proteins, IL-6, members of the Wnt family of proteins, etc., at appropriate concentrations, and ingredients that are known to promote or inhibit the growth of specific cell types and/or agonists and/or antagonists of proteins or other molecules that are known to promote or inhibit the growth of specific cell types can be added to the medium at appropriate concentrations when it is used with those cell types, for example, sphingosine-1-phosphate and pluripotent stem cells. Ingredients can take the form of purified compounds, parts of well-defined mixtures, parts of complex or undefined mixtures, for example, animal or plant oils, and may be added by biological processes, for example, conditioning. The concentrations of the components can be varied from the listed values within ranges that will be obvious to persons skilled in the art.

Example 3 Transfection of Cells with Synthetic RNA

Figure 2A:
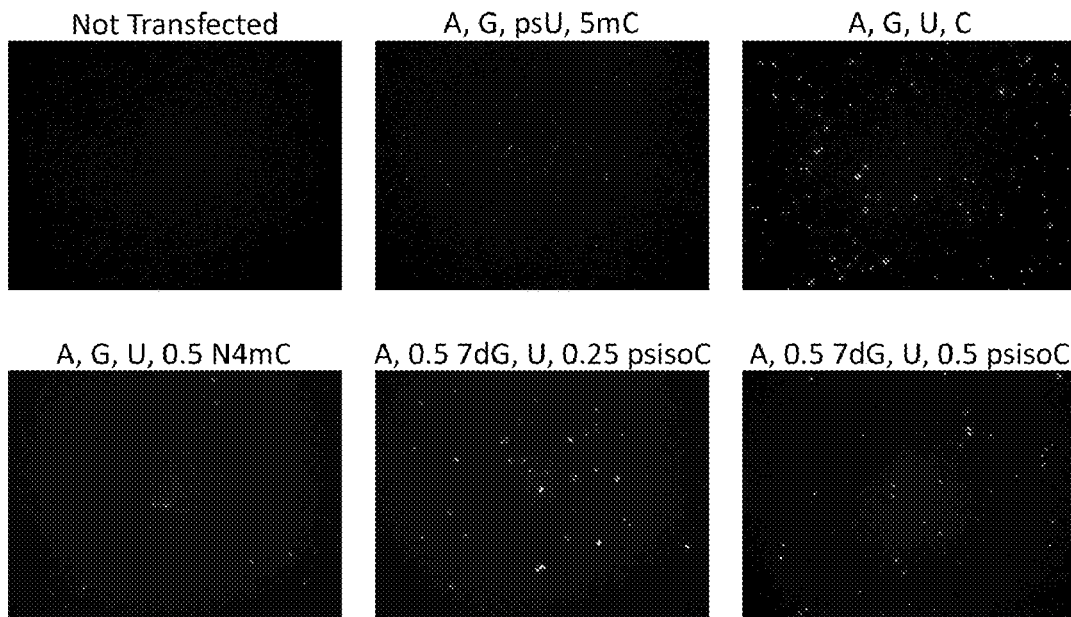
Figure 2B:
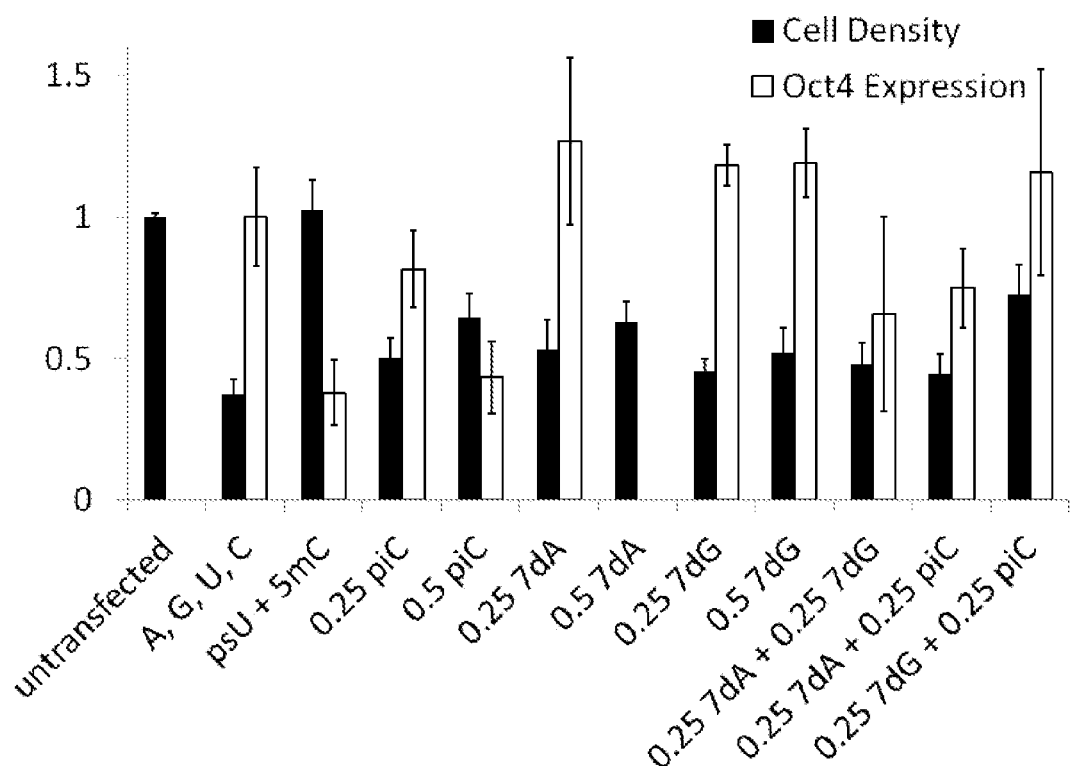

For transfection in 6-well plates, 2 μg RNA and 6 μL transfection reagent (Lipofectamine™ RNAiMAX, Life Technologies Corporation) were first diluted separately in complexation medium (Opti-MEM®, Life Technologies Corporation) to a total volume of 60 μL each. Diluted RNA and transfection reagent were then mixed and incubated for 15 min at room temperature, according to the transfection reagent-manufacturer's instructions. Complexes were then added to cells in culture. Between 30 μL and 240 μL of complexes were added to each well of a 6-well plate, which already contained 2 mL of transfection medium per well. Plates were then shaken gently to distribute the complexes throughout the well. Cells were incubated with complexes for 2 hours to overnight, before replacing the medium with fresh transfection medium (2 mL/well). Volumes were scaled for transfection in 24-well and 96-well plates. Cells were fixed and stained 20-24 h after transfection using an antibody against Oct4 (FIG. 2A). Nuclei were stained and counted to determine the relative toxicity of the RNA (FIG. 2B).

Example 4 Analysis of the Ability of Untreated Human Serum Albumin Preparations to Support Nucleic Acid Transfection and RNA Reprogramming Primary human neonatal fibroblasts were cultured in medium with or without 5 mg/mL HSA. Cohn Fraction V (A6784, Sigma-Aldrich Co. LLC.), and four different recombinant HSA preparations (A6608, A7736, A9731, and A9986, all from Sigma-Aldrich Co. LLC.) were screened. Cells were transfected according to Example 3, with RNA synthesized according to Example 1. While untransfected cells grew well in media containing any of the HSA preparations, in transfected wells, each of the HSA preparations yielded dramatically different cell morphologies and cell densities, and none resulted in morphological changes indicative of reprogramming.

Example 5 Production of Octanoate-Treated Human Serum Albumin

A 10% solution of HSA was pre-incubated with 22 mM sodium chloride and 16 mM sodium octanoate (Sigma-Aldrich Co. LLC), and was incubated at 37 C for 3 hours before assembly of the complete medium.

Example 6 Treatment of Human Serum Albumin Using Ion-Exchange Chromatography A 20% solution of recombinant HSA produced in *Pichia pastoris* (A7736, Sigma-Aldrich Co. LLC.) was prepared by dissolving 2 g of HSA in 10 mL of nuclease-free water with gentle agitation at room temperature. The HSA solution was then deionized by first adding 1 g of mixed-bed deionizing resin (AG 501-X8(D), Bio-Rad Laboratories, Inc.), and rocking for 1 h at room temperature. The HSA solution was then decanted into a tube containing 5 g of fresh resin, and was rocked for 4 h at room temperature. Finally, the deionized HSA solution was decanted, adjusted to a 10% total protein content with nuclease-free water, filter-sterilized using a 0.2 μm PES-membrane filter, and stored at 4 C.

Example 7 Analysis of Transfection Efficiency and Viability of Cells Cultured in Media Containing Octanoate-Treated Human Serum Albumin Primary human neonatal fibroblasts were cultured in media containing recombinant HSA treated according to Example 4 or containing treated blood-derived HSA (Bio-Pure HSA, Biological Industries). Cells were transfected daily, according to Example 3, with RNA synthesized according to Example 1, beginning on day 0. Pictures were taken on day 3. Several small areas of cells undergoing morphological changes resembling mesenchymal to epithelial transition were observed in the wells containing octanoate, indicating an increased transfection efficiency. Many large areas of morphological changes resembling mesenchymal to epithelial transition were observed in the samples containing the treated blood-derived HSA. In both cases, the morphological changes were characteristic of reprogramming.

Example 8 Reprogramming Human Fibroblasts Using Media Containing Octanoate-Treated Human Serum Albumin Primary human neonatal fibroblasts were plated in 6-well plates at a density of 5000 cells/well in fibroblast medium (DMEM+10% fetal bovine serum). After 6 hours, the medium was replaced with transfection medium containing octanoate-treated HSA. The cells were transfected daily, according to Example 3, with RNA synthesized according to Example 1, beginning on day 0. By day 5, the well contained several areas of cells exhibiting morphology consistent with reprogramming. This experiment did not include the use of feeders or immunosuppressants.

Example 9 Analysis of Transfection Efficiency and Viability of Cells Cultured in Media Containing Ion-Exchange-Resin-Treated Human Serum Albumin Primary human neonatal fibroblasts were transfected according to Example 3, with RNA synthesized according to Example 1, beginning on day 0. Pictures were taken on day 2. Cells in the well containing untreated HSA exhibited low viability compared to either the well containing treated blood-derived HSA or ion-exchange-resin-treated recombinant HSA.

Example 10 Reprogramming Human Fibroblasts Using Ion-Exchange-Resin-Treated Human Serum Albumin Primary human neonatal fibroblasts were plated in 6-well plates on feeders at a density of 10,000 cells/well in fibroblast medium (DMEM+10% fetal bovine serum). The cells were transfected daily according to Example 3, with RNA synthesized according to Example 1, beginning on day 0. A passage with a split ratio of 1:20 was performed on day 4. Pictures were taken on day 10. The well contained many large colonies of cells exhibiting morphology consistent with reprogramming. No colonies were observed in wells exposed to cell-culture media containing untreated HSA.

Example 11 Reprogramming Human Fibroblasts without Using Feeders or Immunosuppressants Primary human fibroblasts were plated in 6-well plates at a density of 20,000 cells/well in fibroblast medium (DMEM+10% fetal bovine serum). After 6 hours, the medium was replaced with transfection medium containing treated HSA and not containing immunosuppressants, and the cells were transfected daily according to Example 3, with RNA synthesized according to Example 1, except that the dose of RNA was reduced to 1 µg/well and a total of 5 transfections were performed. Pictures were taken on day 7. Small colonies of cells exhibiting morphology consistent with reprogramming became visible as early as day 5. On day 7, the medium was replaced with DMEM/F12+20% Knockout™ Serum Replacement (Life Technologies Corporation)+1× non-essential amino acids+2 mM L-glutamine, conditioned on irradiated mouse embryonic fibroblasts for 24 hours, and then supplemented with 20 ng/mL bFGF and 10 µM Y-27632. Large colonies with a reprogrammed morphology became visible as early as day 8. Colonies were picked on day 10, and plated in wells coated with basement membrane extract (Cultrex® Human BME Pathclear®, Trevigen Inc.) (FIG. 3A). Cells grew rapidly, and were passaged to establish lines. Established lines stained positive for the pluripotent stem-cell markers Oct4 and SSEA4 (FIG. 3B). The entire protocol was repeated, and similar results were obtained (FIG. 3C).

Example 12 Efficient, Rapid Derivation and Reprogramming of Cells from Human Skin Biopsy Tissue A full-thickness dermal punch biopsy was performed on a healthy, 31 year-old volunteer, according to an approved protocol. Briefly, an area of skin on the left, upper arm was anesthetized by topical application of 2.5% lidocaine. The field was disinfected with 70% isopropanol, and a full-thickness dermal biopsy was performed using a 1.5 mm-diameter punch (FIG. 4A). The tissue was rinsed in phosphate-buffered saline (PBS), and was placed in a 1.5 mL tube containing 250 µL of TrypLE™ Select CTS™ (Life Technologies Corporation), and incubated at 37 C for 30 min. The tissue was then transferred to a 1.5 mL tube containing 250 µL of DMEM/F12-CTS™ (Life Technologies Corporation)+5 mg/mL collagenase, and incubated at 37 C for 2 h (FIG. 4B). The epidermis was removed using forceps, and the tissue was mechanically dissociated. Cells were rinsed twice in DMEM/F12-CTS™ and were plated in fibronectin-coated wells of 24-well and 96-well plates. Phlebotomy was also performed on the same volunteer, and venous blood was collected in Vacutainer® SST™ tubes (Becton, Dickinson and Company). Serum was isolated according to the manufacturer's protocol. Isogenic plating medium was prepared by mixing DMEM/F12-CTS™+2 mM L-alanyl-L-glutamine (Sigma-Aldrich Co. LLC.)+20% human serum. Cells from the dermal tissue sample were plated either in transfection medium or in isogenic plating medium. After 2 days, the wells were rinsed, and the medium was replaced with transfection medium. Many cells with a fibroblast morphology attached and began to spread by day 2 (FIG. 4C). Cells were transfected according to Example 3, with RNA synthesized according to Example 1, beginning on day 2, with all volumes scaled to accommodate the smaller wells. By day 5, areas of cells with morphologies consistent with reprogramming were observed.

Example 13 Reprogramming Human Fibroblasts Using Synthetic RNA Containing Non-Canonical Nucleotides Primary human fibroblasts were plated in 6-well plates coated with recombinant human fibronectin and recombinant human vitronectin (each diluted in DMEM/F12 to a concentration of 1 µg/mL, 1 mL/well, incubated at room temperature for 1 h) at a density of 20,000 cells/well in transfection medium. The following day, the cells were transfected as in Example 3, with RNA synthesized according to Example 1, except that the dose of RNA was 0.5 µg/well on day 1, 0.5 µg/well on day 2, and 2 µg/well on day 3. Pictures were taken on day 4. Small colonies of cells exhibiting morphology consistent with reprogramming were visible on day 4.

Example 14 Reprogramming Human Fibroblasts with a Non-Conditioned Transfection Medium Primary human fibroblasts were plated in 6-well plates coated with recombinant human fibronectin and recombinant human vitronectin (each diluted in DMEM/F12 to a concentration of 1 µg/mL, 1 mL/well, incubated at room temperature for 1 h) at a density of 20,000 cells/well in transfection medium. The following day, the cells were transfected as in Example 3, with RNA synthesized according to Example 1, except that the dose of RNA was 0.5 µg/well on day 1, 0.5 µg/well on day 2, 4 g/well on day 3, 2 µg/well on day 4, and 4 µg/well on day 5. Small colonies of cells exhibiting morphology consistent with reprogramming became visible as early as day 5. On day 7, the medium was replaced with DMEM/F12+20% Knockout™ Serum Replacement (Life Technologies Corporation)+1× non-essential amino acids+2 mM L-glutamine, conditioned on irradiated mouse embryonic fibroblasts for 24 hours, and then supplemented with 20 ng/mL bFGF and 10 µM Y-27632. Large colonies with a reprogrammed morphology became visible as early as day 8. Colonies were picked on day 10, and plated in wells coated with basement membrane extract (Cultrex® Human BME Pathclear®, Trevigen Inc.). Cells grew rapidly, and were passaged to establish lines.

Example 15 Generation of Glucose-Responsive Insulin-Producing Cells

Cells are reprogrammed according to Example 11 or Example 12, and are then cultured in DMEM/F12+0.2% HSA+0.5×N2 supplement+0.5×B27 supplement+100 ng/mL activin A+1 µM wortmannin for 4 days, followed by 1:1 F12/IMDM+0.5% HSA+0.5% ITS supplement+0.5× B27 supplement+2 µM retinoic acid+20 ng/mL FGF7+50 ng/mL NOGGIN for 4 days, followed by DMEM+0.5% HSA+1% ITS supplement+1×N2 supplement+50 ng/mL EGF for 5 days, followed by DMEM/F12+1% ITS supplement+10 ng/mL bFGF+10 mM nicotinamide+50 ng/mL exendin-4+10 ng/mL BMP4 for 7-9 days to generate glucose-responsive insulin-producing cells. Alternatively, cells are reprogrammed according to Example 11 or Example 12, and are then cultured in 1:1 F12/IMDM+0.5% HSA+0.5% ITS supplement+0.5×B27 supplement+2 µM retinoic acid+ 20 ng/mL FGF7+50 ng/mL NOGGIN for 4 days, followed by DMEM+0.5% HSA+1% ITS supplement+1×N2 supplement+50 ng/mL EGF for 5 days, followed by DMEM/F12+ 1% ITS supplement+10 ng/mL bFGF+10 mM nicotinamide+50 ng/mL exendin-4+10 ng/mL BMP4 for 7-9 days to generate glucose-responsive insulin-producing cells, without generating definitive endoderm cells. Alternatively, cells are reprogrammed according to Example 11 or Example 12, and are then cultured in 1:1 F12/IMDM+0.5% HSA+0.5% ITS supplement+0.5×B27 supplement+2 µM retinoic acid+ 20 ng/mL FGF7+50 ng/mL NOGGIN for 4 days, followed by DMEM/F12+1% ITS supplement+10 ng/mL bFGF+10 mM nicotinamide+50 ng/mL exendin-4+10 ng/mL BMP4 for 7-9 days to generate glucose-responsive insulin-producing cells, without generating definitive endoderm cells, and without expanding progenitor cells. While endodermal cells or insulin-producing cells can be isolated from other cells present in the culture, this method generates a sufficiently high percentage of glucose-responsive insulin producing cells that such isolation is not generally required. The resulting cells can then be used in vitro or in vivo for screening bioactive molecules for the study of diabetes or for the development of therapeutics for diabetes.

Example 16 Generation of Glucose-Responsive Insulin-Producing Cells Using Recombinant Proteins Cells were reprogrammed according to Example 11, and were then cultured in DMEM/F12, 100 ng/ml activin A, 25 ng/ml Wnt3a, 0.01% recombinant HSA, 1×ITSE for 1 day, followed by DMEM/F12, 100 ng/ml activin A, 0.01% recombinant HSA, 1×ITSE for 2 days, followed by DMEM/ F12, 50 ng/ml FGF10, 0.25 µM KAAD-cyclopamine, 0.01% recombinant HSA, 1×ITSE for 3 days, followed by DMEM/ F12, 1% B27, 2 µM all-trans retinoic acid, 50 ng/ml FGF10, 0.25 µM KAAD-cyclopamine for 4 days, followed by DMEM/F12, 1% B27, 1 µM γ-secretase inhibitor DAPT, 50 ng/ml exendin-4, 10 nM betacellulin, 10 mM nicotinamide for 2 days, followed by DMEM/F12, 50 mg/L ascorbic-acid-2-phosphate, 1% B27, 1 µM γ-secretase inhibitor DAPT, 50 ng/ml exendin-4, 50 ng/ml IGF-1, 50 ng/ml HGF, 10 nM betacellulin, 10 mM nicotinamide for 6 days to generate glucose-responsive insulin-producing cells (FIG. 5A). The resulting cells can be used in vitro or in vivo for screening bioactive molecules for the study of diabetes or for the development of therapeutics for diabetes.

Example 17 Personalized Cell-Replacement Therapy for Type 1 Diabetes Comprising Reprogrammed Cells Patient skin cells are reprogrammed to glucose-responsive insulin-producing cells according to Example 12 and Example 14. Cells are then enzymatically released from the culture vessel, and between about $1 \times 10^6$ and about $1 \times 10^7$ cells are injected into the intraperitoneal space or into the portal vein. In the case of intraperitoneal injection, cells are pre-mixed with an extracellular matrix protein to prevent excessive migration. Cells engraft and begin producing insulin. Insulin/C-peptide levels are monitored, and additional injections are performed as necessary.

Example 18 Synthesis of RNA TALENs

RNA encoding 20 bp-matching TALENs was synthesized from DNA templates as in Example 1 (FIGS. 6A-C and FIG. 7) (Table 2). The resulting RNA was analyzed by agarose gel electrophoresis to assess the quality of the RNA. The RNA was then diluted to 200 ng/µL, and an RNase inhibitor (Superase•In™, Life Technologies Corporation) was added at a concentration of 1 µL/100 µg of RNA. RNA solutions were stored at 4 C. RNA encoding each half of the TALEN pair was mixed at a molar ratio of 1:1.

TABLE 2

| Template | Nucleotides | Reaction Volume/µL | ivT Yield/µL |
|---|---|---|---|
| XPA-L1 | A, G, psU, 5mC | 20 | 120.0 |
| XPA-L2 | A, G, psU, 5mC | 20 | 114.0 |
| XPA-R1 | A, G, psU, 5mC | 20 | 159.6 |
| CCR5-L1 | A, G, psU, 5mC | 20 | 170.4 |
| CCR5-L2 | A, G, psU, 5mC | 20 | 142.8 |
| CCR5-R1 | A, G, psU, 5mC | 20 | 132.0 |
| CCR5-R2 | A, G, psU, 5mC | 20 | 154.8 |
| CCR5-L1 | A, G, psU, 5mC | 10 | 56.6 |
| CCR5-L2 | A, G, psU, 5mC | 10 | 58.5 |
| CCR5-R1 | A, G, psU, 5mC | 10 | 56.8 |
| CCR5-R2 | A, G, psU, 5mC | 10 | 58.7 |

Example 19 Synthesis of RNA TALENs Targeting the CCR5 Gene

RNA encoding the TALENs L1: TCATTTTCCATA-CAGTCAGT, L2: TTTTCCATACAGTCAGTATC, R1: TGACTATCTTTAATGTCTGG, and R2: TATCTT-TAATGTCTGGAAAT was synthesized according to Example 18. These TALENs target 20-bp sites within the CCR5 gene on the sense (L1 and L2) or antisense strand (R1 and R2). The following TALEN pairs were prepared: L1 &R1, L1&R2, L2&R1, and L2&R2.

Example 20 Gene-Editing of the CCR5 Gene Using RNA TALENs and DNA-Free, Feeder-Free, Immunosuppressant-Free, Conditioning-Free Reprogramming of Human Fibroblasts Primary human fibroblasts were plated in 6-well plates coated with recombinant human fibronectin and recombinant human vitronectin (each diluted in DMEM/F12 to a concentration of 1 µg/mL, 1 mL/well, incubated at room temperature for 1 h) at a density of 10,000 cells/well in transfection medium. The following day, the cells were transfected as in Example 3, except that the dose of RNA was 0.5 µg/well, and the RNA was synthesized according to Example 19. Beginning the following day, the cells were reprogrammed according to Example 11. Large colonies of cells with a morphology characteristic of reprogramming became visible as in Example 11. Pictures were taken on day 9 (FIG. 8).

Example 21 Transfection of Cells with RNA TALENs and a DNA Repair Template 0.5 ug RNA+0.5 ug DNA containing the 1001 bp-region spanning from 500 bp upstream of the targeted double-strand break location to 500 bp downstream of the targeted double-strand break location and 6 μL transfection reagent (Lipofectamine™ 2000, Life Technologies Corporation) are first diluted separately in complexation medium (Opti-MEM®) to a total volume of 60 μL each. Diluted RNA+ DNA and transfection reagent are then mixed and incubated for 15 min at room temperature, according to the transfection reagent-manufacturer's instructions. Complexes are then added to cells in culture. Between 60 μL and 120 μL are added to each well of a 6-well plate, which already contains 2 mL of transfection medium per well. Plates are then shaken gently to distribute the complexes throughout the well. Cells are incubated with complexes for 2 hours to overnight, before replacing the medium with fresh transfection medium (2 mL/well).

Example 22 Gene Editing Using RNA TALENs and a DNA Repair Template and DNA-Free, Feeder-Free, Immunosuppressant-Free, Conditioning-Free Reprogramming of Human Fibroblasts Primary human fibroblasts are plated in 6-well plates at a density of 10,000 cells/well in fibroblast medium (DMEM+ 10% fetal bovine serum). After 6 hours, the medium is replaced with transfection medium containing treated HSA and not containing immunosuppressants, and the cells are transfected according to Example 21. Beginning the following day, the cells are reprogrammed according to Example 11 or Example 12, except that the initial plating and media change steps are omitted.

Example 23 Generation of Hematopoietic Cells

Cells were reprogrammed according to Example 11, and were then cultured in IMDM+0.5% HSA+1x ITS supplement+450 μM monothioglycerol+2 mM L-glutamine+1× non-essential amino acids+50 ng/mL BMP4+50 ng/mL VEGF+50 ng/mL bFGF for 6 days to generate hematopoietic cells (FIG. 5B). Alternatively, cells are reprogrammed according to Example 11 or Example 12 or Example 20 or Example 22, and are then cultured in IMDM+0.5% HSA+ 1×ITS supplement+450 μM monothioglycerol+2 mM L-glutamine+1× non-essential amino acids+50 ng/mL BMP4+50 ng/mL VEGF+50 ng/mL bFGF for 6 days, followed by IMDM+0.5% HSA+1×ITS supplement+0.1 mM 2-mercaptoethanol+5 U/mL heparin+10 ng/mL TPO+25 ng/mL SCF+ 25 ng/mL FLT3L+10 ng/mL IL-3+10 ng/mL IL-6 for 8 days to generate hematopoietic cells. Alternatively, cells are reprogrammed according to Example 11 or Example 12 or Example 20 or Example 22, and are then re-plated on collagen IV and cultured in IMDM+0.5% HSA+1×ITS supplement+450 μM monothioglycerol+2 mM L-glutamine+1× non-essential amino acids+50 ng/mL BMP4+50 ng/mL VEGF+50 ng/mL bFGF for 6 days, followed by IMDM+0.5% HSA+1×ITS supplement+0.1 mM 2-mercaptoethanol+5 U/mL heparin+10 ng/mL TPO+25 ng/mL SCF+ 25 ng/mL FLT3L+10 ng/mL IL-3+10 ng/mL IL-6 for 8 days to generate hematopoietic cells. Alternatively, cells are reprogrammed according to Example 11 or Example 12 or Example 20 or Example 22, and are then cultured in 1:1 F12/IMDM+0.5% HSA+1×ITS supplement+4.5 μg/mL cholesterol+10 μg/mL cod liver oil fatty acids+25 μg/mL polyoxyethylenesorbitan monooleate+2 μg/mL D-α-tocopherol acetate+450 μM monothioglycerol+2 mM L-glutamine+25 ng/mL BMP4+25 ng/mL VEGF+25 ng/mL bFGF+20 ng/mL SCF for 10 days to generate hematopoietic cells.

Example 24 Personalized Cell-Replacement Therapy for Blood Disease Comprising Reprogrammed Cells Patient skin cells are reprogrammed to hematopoietic cells according to Example 23. Cells are then released from the culture vessel, and between about $1 \times 10^6$ and about $1 \times 10^7$ cells/kg patient body weight are infused into a main vein over a period of several hours.

Example 25 Personalized Cell-Replacement Therapy for HIV/AIDS Comprising Gene-Edited and Reprogrammed Cells Patient skin cells are gene-edited and reprogrammed to hematopoietic cells according to Example 23. Cells are then enzymatically released from the culture vessel, and between about $1 \times 10^6$ and about $1 \times 10^7$ cells/kg patient body weight are infused into a main vein over a period of several hours. Hematopoietic stem cells home to the bone marrow cavity and engraft. Alternatively, patient skin cells are gene-edited and reprogrammed to hematopoietic cells according to Example 23, cells are then enzymatically released from the culture vessel, and CD34+/CD90+/Lin− or CD34+/CD49f+/ Lin− cells are isolated. Between about $1 \times 10^3$ and about $1 \times 10^5$ cells are infused into a main vein of the patient. Hematopoietic stem cells home to the bone marrow cavity and engraft.

Example 26 Cardiac Disease Models for Screening Bioactive Molecules

Cells were reprogrammed according to Example 11, and were then cultured in DMEM/F12+0.2% HSA+0.5×N2 supplement+0.5×B27 supplement+100 ng/mL activin A+1 μM wortmannin for 4 days, followed by 1:1 F12/IMDM+ 0.5% HSA+0.5% ITS supplement+0.5×B27 supplement+2 μM retinoic acid+20 ng/mL FGF7+50 ng/mL NOGGIN for 4 days, followed by DMEM/F12+1% ITS supplement+10 ng/mL bFGF+10 mM nicotinamide+50 ng/mL exendin-4+ 10 ng/mL BMP4 for 7-9 days to generate cardiac cells (FIG. 5C). Alternatively, cells are reprogrammed according to Example 12. While cardiac cells can be isolated from other cells present in the culture, this method generates a sufficiently high percentage of cardiac cells that such isolation is not generally required. The resulting cells can be used in vitro or in vivo for screening bioactive molecules for the study of heart disease or for the development of therapeutics for heart disease. The resulting cells can also be used for cardiotoxicity screening.

Example 27 Personalized Cell-Replacement Therapy for Ischemic Cardiomyopathy Comprising Reprogrammed Cells Patient skin cells are reprogrammed to cardiac cells according to Example 26. Cells are then enzymatically released from the culture vessel, and between about $1 \times 10^6$ and about $1 \times 10^7$ cells are injected into the pericardium or between about $1 \times 10^3$ and about $1 \times 10^5$ cells are injected into one or more coronary arteries. Cells engraft, and additional injections are performed as necessary.

Example 28 Retinal Disease Models for Screening Bioactive Molecules

Cells are reprogrammed according to Example 11 or Example 12, and are then cultured in DMEM/F12+0.2% HSA+0.5×N2 supplement+0.5×B27 supplement 7 days to generate retinal cells. The resulting cells can be used in vitro or in vivo for screening bioactive molecules for the study of retinal disease or for the development of therapeutics for retinal disease.

Example 29 Personalized Cell-Replacement Therapy for Macular Degeneration Comprising Reprogrammed Cells Patient skin cells are reprogrammed to retinal cells according to Example 28. Cells are then enzymatically released from the culture vessel, and between about $1\times10^4$ and about $1\times10^5$ cells are injected into or below the retina. Cells engraft, and additional injections are performed as necessary.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

---

What is claimed is:

1. A method for altering a target DNA sequence in a cell, comprising:
   (a) providing a human somatic cell comprising a target DNA sequence;
   (b) culturing the cell; and
   (c) transfecting the cell with a plurality of synthetic RNA molecules, wherein the synthetic RNA molecules include:
   i. a first synthetic RNA molecule encoding a first fusion protein comprising a DNA-binding domain and a catalytic domain of a nuclease; and
   ii. a second synthetic RNA molecule encoding a second fusion protein comprising a DNA-binding domain and a catalytic domain of a nuclease;
   wherein:
   the first fusion protein and the second fusion protein are independently a transcription activator-like effector nuclease (TALEN); and the transfecting results in the cell expressing the first fusion protein and the second fusion protein to result in a single-strand break or a double-strand break.

2. The method of claim 1, further comprising contacting the cell with at least one of poly-L-lysine, poly-L-ornithine, RGD peptide, fibronectin, vitronectin, collagen, and laminin.

3. The method of claim 1, further comprising contacting the cell with a medium.

4. A method for altering a target DNA sequence in a cell, comprising:
(a) providing a human somatic cell comprising a target DNA sequence,
(b) culturing the cell;
(c) transfecting the cell with a plurality of synthetic RNA molecules, wherein the synthetic RNA molecules include:
  i. a first synthetic RNA molecule encoding a first fusion protein comprising a DNA-binding domain and a catalytic domain of a nuclease; and
  ii. a second synthetic RNA molecule encoding a second fusion protein comprising a DNA-binding domain and a catalytic domain of a nuclease;
  wherein the first fusion protein and the second fusion protein are independently a transcription activator-like effector nuclease (TALEN); and wherein the transfecting results in the cell expressing the first fusion protein and the second fusion protein to result in a single-strand break or a double-strand break in the target DNA sequence; and
(d) transfecting the cell with a DNA repair template comprising a sequence for insertion and one or more regions of homology to the DNA of the cell, wherein the one or more regions of homology comprise regions upstream and/or downstream of the single-strand break or the double-strand break, to result in insertion of the sequence in the region of the single-strand break or the double-strand break.

5. The method of claim 4, further comprising contacting the cell with at least one of poly-L-lysine, poly-L-ornithine, RGD peptide, fibronectin, vitronectin, collagen, and laminin.

6. The method of claim 4, further comprising contacting the cell with a medium.

7. The method of claim 1, wherein the human somatic cell is a skin cell or a hematopoietic cell.

8. The method of claim 7, wherein the hematopoietic cell is a hematopoietic stem cell or a white blood cell.

9. The method of claim 7, wherein the skin cell is obtained from a biopsy, including a dermal punch biopsy.

10. The method of claim 7, wherein the skin cell is a fibroblast, a keratinocyte, a melanocyte, an adipocyte, a mesenchymal stem cell, an adipose stem cell, or a blood cell.

11. The method of claim 1, wherein the plurality of synthetic RNA molecules are complexed with a transfection reagent.

12. The method of claim 11, wherein the transfection reagent is lipid-based, polymer-based, or peptide-based.

13. The method of claim 12, wherein the transfection reagent comprises a charged polymer or a cell-penetrating peptide.

14. The method of claim 12, wherein the transfection reagent comprises a cationic lipid, a, liposome, or a micelle.

15. The method of claim 3, wherein the medium is substantially free of immunosuppressants.

16. The method of claim 1, wherein the first synthetic RNA molecule, the second synthetic RNA molecule, or both the first synthetic RNA molecule and the second synthetic RNA molecule comprise at least one non-canonical nucleotide selected from the group consisting of: a 5-methyluridine residue, a pseudouridine residue, a 5-methylpseudouridine residue, a 5-hydroxyuridine residue, a 5-hydroxypseudouridine residue, and a 5-methylcytidine residue.

17. The method of claim 1, wherein the first synthetic RNA molecule, the second synthetic RNA molecule, or both the first synthetic RNA molecule and the second synthetic RNA molecule further comprise one or more of a 5'-cap, a 5'-cap 1 structure, and a 3'-poly(A) tail.

18. The method of claim 4, wherein the human somatic cell is a skin cell or a hematopoietic cell.

19. The method of claim 18, wherein the hematopoietic cell is a hematopoietic stem cell or a white blood cell.

20. The method of claim 18, wherein the skin cell is obtained from a biopsy, including a dermal punch biopsy.

21. The method of claim 18, wherein the skin cell is a fibroblast, a keratinocyte, a melanocyte, an adipocyte, a mesenchymal stem cell, an adipose stem cell, or a blood cell.

22. The method of claim 4, wherein the plurality of synthetic RNA molecules are complexed with a transfection reagent.

23. The method of claim 22, wherein the transfection reagent is lipid-based, polymer-based, or peptide-based.

24. The method of claim 23, wherein the transfection reagent comprises a charged polymer or a cell-penetrating peptide.

25. The method of claim 23, wherein the transfection reagent comprises a cationic lipid, a, liposome, or a micelle.

26. The method of claim 6, wherein the medium is substantially free of immunosuppressants.

27. The method of claim 4, wherein the first synthetic RNA molecule, the second synthetic RNA molecule, or both the first synthetic RNA molecule and the second synthetic RNA molecule comprise at least one non-canonical nucleotide selected from the group consisting of: a 5-methyluridine residue, a pseudouridine residue, a 5-methylpseudouridine residue, a 5-hydroxyuridine residue, a 5-hydroxypseudouridine residue, and a 5-methylcytidine residue.

28. The method of claim 4, wherein the first synthetic RNA molecule, the second synthetic RNA molecule, or both the first synthetic RNA molecule and the second synthetic RNA molecule further comprise one or more of a 5'-cap, a 5'-cap 1 structure, and a 3'-poly(A) tail.

29. The method of claim 4, wherein the DNA repair template comprises one or more regions of homology to the DNA of the cell upstream or downstream of the single-strand break or the double-strand break.

30. The method of claim 29, wherein the DNA repair template comprises one or more regions of homology to the DNA of the cell upstream of the single-strand break or the double-strand break.

31. The method of claim 29, wherein the DNA repair template comprises one or more regions of homology to the DNA of the cell downstream of the single-strand break or the double-strand break.

32. The method of claim 4, wherein the DNA repair template comprises one or more regions of homology to the DNA of the cell upstream and downstream of the single-strand break or the double-strand break.

* * * * *

SEQUENCE LISTING

```
<160> NUMBER OF SEQ ID NOS: 26

<210> SEQ ID NO 1
<211> LENGTH: 360
<212> TYPE: PRT
<213> ORGANISM: Homo sapiens

<400> SEQUENCE: 1

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
    130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
    210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255
```

Leu Gln Gln Ile Ser His Ile Ala Gln Gln Leu Gly Leu Glu Lys Asp
                260                 265                 270

Val Val Arg Val Trp Phe Cys Asn Arg Arg Gln Lys Gly Lys Arg Ser
            275                 280                 285

Ser Ser Asp Tyr Ala Gln Arg Glu Asp Phe Glu Ala Ala Gly Ser Pro
        290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
        355                 360

<210> SEQ ID NO 2
<211> LENGTH: 317
<212> TYPE: PRT
<213> ORGANISM: Homo sapiens

<400> SEQUENCE: 2

Met Tyr Asn Met Met Glu Thr Glu Leu Lys Pro Pro Gly Pro Gln Gln
1               5                   10                  15

Thr Ser Gly Gly Gly Gly Asn Ser Thr Ala Ala Ala Ala Gly Gly
                20                  25                  30

Asn Gln Lys Asn Ser Pro Asp Arg Val Lys Arg Pro Met Asn Ala Phe
            35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
        130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
        195                 200                 205

Ser Met Thr Ser Ser Gln Thr Tyr Met Asn Gly Ser Pro Thr Tyr Ser
    210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Ser Pro Pro Val Val Thr
                245                 250                 255

Ser Ser Ser His Ser Arg Ala Pro Cys Gln Ala Gly Asp Leu Arg Asp

-continued

```
                    260                 265                 270
Met Ile Ser Met Tyr Leu Pro Gly Ala Glu Val Pro Glu Pro Ala Ala
                275                 280                 285

Pro Ser Arg Leu His Met Ser Gln His Tyr Gln Ser Gly Pro Val Pro
            290                 295                 300

Gly Thr Ala Ile Asn Gly Thr Leu Pro Leu Ser His Met
305                 310                 315

<210> SEQ ID NO 3
<211> LENGTH: 479
<212> TYPE: PRT
<213> ORGANISM: Homo sapiens

<400> SEQUENCE: 3

Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
                20                  25                  30

Thr Leu Arg Gln Ala Gly Ala Pro Asn Asn Arg Trp Arg Glu Glu Leu
            35                  40                  45

Ser His Met Lys Arg Leu Pro Pro Val Leu Pro Gly Arg Pro Tyr Asp
        50                  55                  60

Leu Ala Ala Ala Thr Val Ala Thr Asp Leu Glu Ser Gly Gly Ala Gly
65                  70                  75                  80

Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
            100                 105                 110

Leu Thr His Pro Pro Glu Ser Val Ala Ala Thr Val Ser Ser Ser Ala
        115                 120                 125

Ser Ala Ser Ser Ser Ser Ser Pro Ser Ser Gly Pro Ala Ser Ala
    130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Gly Leu Leu Tyr Gly Arg Glu
                165                 170                 175

Ser Ala Pro Pro Pro Thr Ala Pro Phe Asn Leu Ala Asp Ile Asn Asp
            180                 185                 190

Val Ser Pro Ser Gly Gly Phe Val Ala Glu Leu Leu Arg Pro Glu Leu
        195                 200                 205

Asp Pro Val Tyr Ile Pro Pro Gln Gln Pro Gln Pro Pro Gly Gly Gly
    210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                245                 250                 255

Gly Ser His Pro Val Val Val Ala Pro Tyr Asn Gly Gly Pro Pro Arg
            260                 265                 270

Thr Cys Pro Lys Ile Lys Gln Glu Ala Val Ser Ser Cys Thr His Leu
        275                 280                 285

Gly Ala Gly Pro Pro Leu Ser Asn Gly His Arg Pro Ala Ala His Asp
    290                 295                 300

Phe Pro Leu Gly Arg Gln Leu Pro Ser Arg Thr Thr Pro Thr Leu Gly
305                 310                 315                 320
```

-continued

```
Leu Glu Glu Val Leu Ser Ser Arg Asp Cys His Pro Ala Leu Pro Leu
                325                 330                 335

Pro Pro Gly Phe His Pro His Pro Gly Pro Asn Tyr Pro Ser Phe Leu
            340                 345                 350

Pro Asp Gln Met Gln Pro Gln Val Pro Pro Leu His Tyr Gln Glu Leu
        355                 360                 365

Met Pro Pro Gly Ser Cys Met Pro Glu Glu Pro Lys Pro Lys Arg Gly
    370                 375                 380

Arg Arg Ser Trp Pro Arg Lys Arg Thr Ala Thr His Thr Cys Asp Tyr
385                 390                 395                 400

Ala Gly Cys Gly Lys Thr Tyr Thr Lys Ser Ser His Leu Lys Ala His
                405                 410                 415

Leu Arg Thr His Thr Gly Glu Lys Pro Tyr His Cys Asp Trp Asp Gly
            420                 425                 430

Cys Gly Trp Lys Phe Ala Arg Ser Asp Glu Leu Thr Arg His Tyr Arg
        435                 440                 445

Lys His Thr Gly His Arg Pro Phe Gln Cys Gln Lys Cys Asp Arg Ala
    450                 455                 460

Phe Ser Arg Ser Asp His Leu Ala Leu His Met Lys Arg His Phe
465                 470                 475

<210> SEQ ID NO 4
<211> LENGTH: 454
<212> TYPE: PRT
<213> ORGANISM: Homo sapiens

<400> SEQUENCE: 4

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
        195                 200                 205

Val Phe Pro Tyr Pro Leu Asn Asp Ser Ser Ser Pro Lys Ser Cys Ala
    210                 215                 220
```

-continued

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
            245                 250                 255

Glu Glu Thr Pro Pro Thr Thr Ser Ser Asp Ser Glu Glu Glu Gln Glu
        260                 265                 270

Asp Glu Glu Glu Ile Asp Val Val Ser Val Glu Lys Arg Gln Ala Pro
    275                 280                 285

Gly Lys Arg Ser Glu Ser Gly Ser Pro Ser Ala Gly Gly His Ser Lys
290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
            325                 330                 335

Ala Lys Arg Val Lys Leu Asp Ser Val Arg Val Leu Arg Gln Ile Ser
        340                 345                 350

Asn Asn Arg Lys Cys Thr Ser Pro Arg Ser Ser Asp Thr Glu Glu Asn
    355                 360                 365

Val Lys Arg Arg Thr His Asn Val Leu Glu Arg Gln Arg Arg Asn Glu
370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
            405                 410                 415

Tyr Ile Leu Ser Val Gln Ala Glu Glu Gln Lys Leu Ile Ser Glu Glu
        420                 425                 430

Asp Leu Leu Arg Lys Arg Arg Glu Gln Leu Lys His Lys Leu Glu Gln
    435                 440                 445

Leu Arg Asn Ser Cys Ala
    450

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aagctttaat acgactcact atagggacat tt                                     32

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aagctttaat acgactcact atagggacat tt                                     32

<210> SEQ ID NO 7
<211> LENGTH: 9
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 7 gggacattt					9

<210> SEQ ID NO 8
<211> LENGTH: 3428
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (636)..(641)
<223> OTHER INFORMATION: This region may encompass "AACATC," "AACGGA,"
      "CATGAC" or "AACAAC"
<220> FEATURE:
<221> NAME/KEY: modified_base
<222> LOCATION: (738)..(743)
<223> OTHER INFORMATION: This region may encompass "AACATC," "AACGGA,"
      "CATGAC" or "AACAAC"
<220> FEATURE:
<221> NAME/KEY: modified_base
<222> LOCATION: (840)..(845)
<223> OTHER INFORMATION: This region may encompass "AACATC," "AACGGA,"
      "CATGAC" or "AACAAC"
<220> FEATURE:
<221> NAME/KEY: modified_base
<222> LOCATION: (942)..(947)
<223> OTHER INFORMATION: This region may encompass "AACATC," "AACGGA,"
      "CATGAC" or "AACAAC"
<220> FEATURE:
<221> NAME/KEY: modified_base
<222> LOCATION: (1044)..(1049)
<223> OTHER INFORMATION: This region may encompass "AACATC," "AACGGA,"
      "CATGAC" or "AACAAC"
<220> FEATURE:
<221> NAME/KEY: modified_base
<222> LOCATION: (1146)..(1151)
<223> OTHER INFORMATION: This region may encompass "AACATC," "AACGGA,"
      "CATGAC" or "AACAAC"
<220> FEATURE:
<221> NAME/KEY: modified_base
<222> LOCATION: (1248)..(1253)
<223> OTHER INFORMATION: This region may encompass "AACATC," "AACGGA,"
      "CATGAC" or "AACAAC"
<220> FEATURE:
<221> NAME/KEY: modified_base
<222> LOCATION: (1350)..(1355)
<223> OTHER INFORMATION: This region may encompass "AACATC," "AACGGA,"
      "CATGAC" or "AACAAC"
<220> FEATURE:
<221> NAME/KEY: modified_base
<222> LOCATION: (1452)..(1457)
<223> OTHER INFORMATION: This region may encompass "AACATC," "AACGGA,"
      "CATGAC" or "AACAAC"
<220> FEATURE:
<221> NAME/KEY: modified_base
<222> LOCATION: (1554)..(1559)
<223> OTHER INFORMATION: This region may encompass "AACATC," "AACGGA,"
      "CATGAC" or "AACAAC"
<220> FEATURE:
<221> NAME/KEY: modified_base
<222> LOCATION: (1656)..(1661)
<223> OTHER INFORMATION: This region may encompass "AACATC," "AACGGA,"
      "CATGAC" or "AACAAC"
<220> FEATURE:
<221> NAME/KEY: modified_base
<222> LOCATION: (1758)..(1763)
<223> OTHER INFORMATION: This region may encompass "AACATC," "AACGGA,"
      "CATGAC" or "AACAAC"
<220> FEATURE:
<221> NAME/KEY: modified_base
<222> LOCATION: (1860)..(1865)
<223> OTHER INFORMATION: This region may encompass "AACATC," "AACGGA,"
      "CATGAC" or "AACAAC"

```
<220> FEATURE:
<221> NAME/KEY: modified_base
<222> LOCATION: (1962)..(1967)
<223> OTHER INFORMATION: This region may encompass "AACATC," "AACGGA,"
      "CATGAC" or "AACAAC"
<220> FEATURE:
<221> NAME/KEY: modified_base
<222> LOCATION: (2064)..(2069)
<223> OTHER INFORMATION: This region may encompass "AACATC," "AACGGA,"
      "CATGAC" or "AACAAC"
<220> FEATURE:
<221> NAME/KEY: modified_base
<222> LOCATION: (2166)..(2171)
<223> OTHER INFORMATION: This region may encompass "AACATC," "AACGGA,"
      "CATGAC" or "AACAAC"
<220> FEATURE:
<221> NAME/KEY: modified_base
<222> LOCATION: (2268)..(2273)
<223> OTHER INFORMATION: This region may encompass "AACATC," "AACGGA,"
      "CATGAC" or "AACAAC"
<220> FEATURE:
<221> NAME/KEY: modified_base
<222> LOCATION: (2370)..(2375)
<223> OTHER INFORMATION: This region may encompass "AACATC," "AACGGA,"
      "CATGAC" or "AACAAC"
<220> FEATURE:
<221> NAME/KEY: modified_base
<222> LOCATION: (2472)..(2477)
<223> OTHER INFORMATION: This region may encompass "AACATC," "AACGGA,"
      "CATGAC" or "AACAAC"

<400> SEQUENCE: 8
taatacgact cactataggg acatttgctt ctgacacaac tgtgttcact agcaacctca      60
aacagctagc caccatggac tataaggacc acgacggaga ctacaaggat catgatattg     120
attacaaaga cgatgacgat aagatggccc caaagaagaa gcggaaggtc ggtatccacg     180
gagtcccagc agccgtagat ttgagaactt tgggatattc acagcagcag caggaaaaga     240
tcaagcccaa agtgaggtcg acagtcgcgc agcatcacga agcgctggtg ggtcatgggt     300
ttacacatgc ccacatcgta gccttgtcgc agcaccctgc agcccttggc acggtcgccg     360
tcaagtacca ggacatgatt gcggcgttgc cggaagccac acatgaggcg atcgtcggtg     420
tgggaaaaca gtggagcgga gcccgagcgc ttgaggccct gttgacggtc gcggagagc      480 tgagagggcc tccccttcag ctggacacgg ccagttgct gaagatcgcg aagcggggag      540
gagtcacggc ggtcgaggcg gtgcacgcgt ggcgcaatgc gctcacggga gcaccctca      600 acctgacccc agagcaggtc gtggcaattg cgagcnnnnn nggggaaag caggcactcg     660 aaaccgtcca gaggttgctg cctgtgctgt gccaagcgca cggacttacg ccagagcagg     720
tcgtggcaat tgcgagcnnn nnnggggaa agcaggcact cgaaaccgtc cagaggttgc     780
tgcctgtgct gtgccaagcg cacggactaa ccccagagca ggtcgtggca attgcgagcn     840 nnnnggggg aaagcaggca ctcgaaaccg tccagaggtt gctgcctgtg ctgtgccaag     900
cgcacgggtt gaccccagag caggtcgtgg caattgcgag cnnnnnnggg ggaaagcagg     960
cactcgaaac cgtccagagg ttgctgcctg tgctgtgcca agcgcacggc ctgacccag     1020 agcaggtcgt ggcaattgcg agcnnnnnng ggggaaagca ggcactcgaa accgtccaga    1080
ggttgctgcc tgtgctgtgc caagcgcacg gactgacacc agagcaggtc gtggcaattg    1140
cgagcnnnnn nggggaaag caggcactcg aaaccgtcca gaggttgctg cctgtgctgt    1200
gccaagcgca cggacttaca cccgaacaag tcgtggcaat tgcgagcnnn nnnggggaa    1260 agcaggcact cgaaaccgtc cagaggttgc tgcctgtgct gtgccaagcg cacggactta    1320
cgccagagca ggtcgtggca attgcgagcn nnnnnggggg aaagcaggca ctcgaaaccg    1380
```

```
tccagaggtt gctgcctgtg ctgtgccaag cgcacggact aaccccagag caggtcgtgg      1440
caattgcgag cnnnnnnggg ggaaagcagg cactcgaaac cgtccagagg ttgctgcctg      1500
tgctgtgcca agcgcacggg ttgaccccag agcaggtcgt ggcaattgcg agcnnnnnng      1560
ggggaaagca ggcactcgaa accgtccaga ggttgctgcc tgtgctgtgc caagcgcacg      1620
gcctgacccc agagcaggtc gtggcaattg cgagcnnnnn nggggaaaag caggcactcg      1680
aaaccgtcca gaggttgctg cctgtgctgt gccaagcgca cggactgaca ccagagcagg      1740
tcgtggcaat tgcgagcnnn nnnggggggaa agcaggcact cgaaaccgtc cagaggttgc      1800
tgcctgtgct gtgccaagcg cacggcctca ccccagagca ggtcgtggca attgcgagcn      1860
nnnnnggggg aaagcaggca ctcgaaaccg tccagaggtt gctgcctgtg ctgtgccaag      1920
cgcacggact acgccagag caggtcgtgg caattgcgag cnnnnnnggg ggaaagcagg       1980
cactcgaaac cgtccagagg ttgctgcctg tgctgtgcca agcgcacgga ctaacccag       2040 agcaggtcgt ggcaattgcg agcnnnnnng ggggaaagca ggcactcgaa accgtccaga      2100
ggttgctgcc tgtgctgtgc caagcgcacg ggttgacccc agagcaggtc gtggcaattg      2160
cgagcnnnnn nggggaaaag caggcactcg aaaccgtcca gaggttgctg cctgtgctgt      2220
gccaagcgca cggcctgacc ccagagcagg tcgtggcaat tgcgagcnnn nnggggggaa      2280
agcaggcact cgaaaccgtc cagaggttgc tgcctgtgct gtgccaagcg cacggactga      2340
caccagagca ggtcgtggca attgcgagcn nnnnggggg aaagcaggca ctcgaaaccg       2400
tccagaggtt gctgcctgtg ctgtgccaag cgcacggact cacgcctgag caggtagtgg      2460
ctattgcatc cnnnnnnggg ggcagacccg cactggagtc aatcgtggcc cagctttcga     2520
ggccggaccc cgcgctggcc gcactcacta atgatcatct tgtagcgctg gcctgcctcg      2580
gcggacgacc cgccttggat gcggtgaaga aggggctccc gcacgcgcct gcattgatta     2640
agcggaccaa cagaaggatt cccgagagga catcacatcg agtggcaggt tcccaactcg      2700
tgaagagtga acttgaggag aaaaagtcgg agctgcggca caaattgaaa tacgtaccgc      2760
atgaatacat cgaacttatc gaaattgcta ggaactcgac tcaagacaga atccttgaga      2820
tgaaggtaat ggagttcttt atgaaggttt atggataccg agggaagcat ctcggtggat      2880
cacgaaaacc cgacggagca atctatacgg tggggagccc gattgattac ggagtgatcg      2940
tcgacacgaa agcctacagc ggtgggtaca atcttcccat cgggcaggca gatgagatgc      3000
aacgttatgt cgaagaaaat cagaccagga acaaacacat caatccaaat gagtggtgga      3060
aagtgtatcc ttcatcagtg accgagttta agttttgtt tgtctctggg catttcaaag      3120
gcaactataa ggcccagctc acacggttga atcacattac gaactgcaat ggtgcggttt      3180
tgtccgtaga ggaactgctc attggtggag aaatgatcaa agcgggaact ctgacactgg      3240
aagaagtcag acgcaagttt aacaatggcg agatcaattt ccgctcataa accggtgctc      3300
gctttcttgc tgtccaattt ctattaaagg ttcctttgtt ccctaagtcc aactactaaa      3360
ctgggggata ttatgaaggg ccttgagcat ctggattctg cctaataaaa aacatttatt      3420
ttcattgc                                                              3428
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tcattttcca tacagtcagt                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ttttccatac agtcagtatc                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tgactatctt taatgtctgg                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tatctttaat gtctggaaat                                              20

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
caaacagcta gccaccatg                                               19

<210> SEQ ID NO 14
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
acctgacaga gaccaaaaag gatccaaaaa ggtctcgact cacgcc                 46

<210> SEQ ID NO 15
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
accggtgctc gc                                                          12

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cattgcgaat tc                                                          12

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
caaacagcta gccaccatg                                                   19

<210> SEQ ID NO 18
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18 acctgac                                                                 7

<210> SEQ ID NO 19
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19 actcacgcc                                                               9

<210> SEQ ID NO 20
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
accggtgctc gc                                                          12

<210> SEQ ID NO 21
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

```
cattgcgaat tc                                                          12

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
caaacagcta gccaccatg                                                   19

<210> SEQ ID NO 23
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23 acctgac                                                                 7

<210> SEQ ID NO 24
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24 actcacgcc                                                               9

<210> SEQ ID NO 25
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
accggtgctc gc                                                          12

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cattgcgaat tcaaaaaaaa aaa                                              23
```